(12) United States Patent
Nasir

(10) Patent No.: US 8,778,248 B2
(45) Date of Patent: Jul. 15, 2014

(54) METHOD OF MANUFACTURING AN AIRWAY DEVICE

(76) Inventor: Muhammed Aslam Nasir, Bedfordshire (GB)

( * ) Notice: Subject to any disclaimer, the term of this patent is extended or adjusted under 35 U.S.C. 154(b) by 0 days.

(21) Appl. No.: 13/403,806

(22) Filed: Feb. 23, 2012

(65) Prior Publication Data

US 2012/0241084 A1   Sep. 27, 2012

Related U.S. Application Data

(60) Division of application No. 10/983,199, filed on Nov. 5, 2004, now Pat. No. 8,215,307, which is a continuation-in-part of application No. PCT/GB03/03577, filed on Aug. 14, 2003.

(30) Foreign Application Priority Data

| Aug. 14, 2002 | (GB) | .................................... 0218868.8 |
| May 7, 2004 | (EP) | .................................... 000180757 |
| Jun. 24, 2004 | (EP) | .................................... 000197124 |
| Aug. 13, 2004 | (GB) | ................. PCT/GB2004/003481 |

(51) Int. Cl.
*B29C 45/16* (2006.01)

(52) U.S. Cl.
USPC ...................... 264/250; 264/328.1; 264/328.8

(58) Field of Classification Search
None
See application file for complete search history.

(56) References Cited

U.S. PATENT DOCUMENTS

| 2,099,127 | A | 11/1937 | Leech ....................... 128/207.15 |
| 3,616,799 | A | 11/1971 | Sparks .......................... 128/351 |
| 3,734,100 | A | 5/1973 | Walker et al. ................. 128/351 |
| 3,968,800 | A | 7/1976 | Vilasi ............................ 128/343 |
| 3,995,643 | A | 12/1976 | Merav .......................... 128/351 |
| 4,509,514 | A | 4/1985 | Brain ........................ 128/207.15 |
| 4,919,126 | A | 4/1990 | Baildon .................... 128/207.14 |
| 4,995,388 | A | 2/1991 | Brain ........................ 128/207.15 |
| 5,054,483 | A | 10/1991 | Marten et al. ............ 128/207.14 |
| 5,174,283 | A | 12/1992 | Parker ....................... 128/200.26 |
| 5,241,956 | A | 9/1993 | Brain ........................ 128/207.15 |
| 5,249,571 | A | 10/1993 | Brain ........................ 128/207.14 |

(Continued)

FOREIGN PATENT DOCUMENTS

| AU | B-52036/90 | 9/1990 | ............ A61M 16/04 |
| AU | B-45803/93 | 2/1994 | ............ A61M 16/04 |

(Continued)

OTHER PUBLICATIONS

UK Search and Examination Report issued in corresponding application No. GB1110775.2, dated Oct. 18, 2011 (8 pgs).

(Continued)

*Primary Examiner* — Edmund H. Lee
(74) *Attorney, Agent, or Firm* — Hayes Soloway P.C.

(57) ABSTRACT

An airway device for human or animal use comprising an airway tube having a distal end and a proximal end, the distal and of which is surrounded by a laryngeal cuff, adapted to fit anatomically over the laryngeal structure of a patient, wherein the device optionally further comprises a buccal cavity stabilizer located on or around the airway tube between the laryngeal cuff and the proximal end of the tube, said buccal cavity stabilizer being adapted to nest with the anterior aspect of the patient's tongue, the size, shape and configuration of the buccal stabilizer being adapted to prevent rotational or side-to-side movement of the airway device in use.

2 Claims, 46 Drawing Sheets

DEVICE IN SITU

(56) References Cited

U.S. PATENT DOCUMENTS

| | | | |
|---|---|---|---|
| 5,282,464 A | 2/1994 | Brain | 128/207.15 |
| 5,285,778 A | 2/1994 | Mackin | 128/207.15 |
| 5,297,547 A | 3/1994 | Brain | 128/207.15 |
| 5,303,697 A | 4/1994 | Brain | 128/200.26 |
| 5,305,743 A | 4/1994 | Brain | 128/207.15 |
| 5,322,062 A | 6/1994 | Servas | 128/207.14 |
| 5,355,879 A | 10/1994 | Brain | 128/207.15 |
| 5,391,248 A * | 2/1995 | Brain | 156/242 |
| 5,477,851 A | 12/1995 | Callaghan et al. | 128/207.15 |
| 5,584,290 A | 12/1996 | Brain | 128/207.15 |
| 5,623,921 A | 4/1997 | Kinsinger et al. | 128/200.26 |
| 5,632,271 A | 5/1997 | Brain | 128/207.15 |
| 5,655,519 A | 8/1997 | Alfery | 128/200.26 |
| 5,682,880 A | 11/1997 | Brain | 128/207.15 |
| 5,711,293 A | 1/1998 | Brain | 128/200.24 |
| 5,791,341 A | 8/1998 | Bullard | 128/207.15 |
| 5,865,176 A | 2/1999 | O'Neil | 128/207.15 |
| 5,878,745 A | 3/1999 | Brain | 128/207.15 |
| 5,881,726 A | 3/1999 | Neame | 128/207.15 |
| 5,896,858 A | 4/1999 | Brain | 128/207.15 |
| 5,915,383 A | 6/1999 | Pagan | 128/207.15 |
| 5,921,988 A | 7/1999 | Legrand | 606/87 |
| 5,937,859 A | 8/1999 | Augustine et al. | 128/207.15 |
| 5,937,860 A * | 8/1999 | Cook | 128/207.15 |
| 5,964,217 A | 10/1999 | Christopher | 128/200.26 |
| 5,976,072 A | 11/1999 | Greenberg | 600/120 |
| 5,979,445 A | 11/1999 | Neame et al. | 128/207.15 |
| 5,988,167 A | 11/1999 | Kamen | 128/207.15 |
| 6,003,514 A | 12/1999 | Pagan | 128/207.15 |
| 6,055,984 A | 5/2000 | Brain | 128/207.14 |
| 6,070,581 A | 6/2000 | Augustine et al. | 128/207.15 |
| 6,079,409 A | 6/2000 | Brain | 128/200.26 |
| D429,811 S | 8/2000 | Bermudez | D24/110.5 |
| 6,095,144 A | 8/2000 | Pagan | 128/207.15 |
| 6,152,136 A | 11/2000 | Pagan | 128/207.15 |
| 6,216,696 B1 | 4/2001 | van den Berg | 128/207.14 |
| 6,280,675 B1 | 8/2001 | Legrand | 264/262 |
| 6,311,688 B1 | 11/2001 | Augustine et al. | 128/200.26 |
| 6,318,367 B1 | 11/2001 | Mongeon | 128/207.15 |
| 6,422,239 B1 * | 7/2002 | Cook | 128/207.15 |
| 6,439,232 B1 | 8/2002 | Brain | 128/207.15 |
| 6,474,332 B2 | 11/2002 | Arndt | 128/200.26 |
| 6,536,437 B1 | 3/2003 | Dragisic | 128/207.18 |
| 6,604,525 B2 | 8/2003 | Pagan | 128/207.15 |
| 6,631,720 B1 | 10/2003 | Brain | 128/207.14 |
| 6,679,263 B2 | 1/2004 | Luchetti et al. | 128/207.15 |
| 6,698,430 B2 | 3/2004 | Van Landuyt | 128/207.15 |
| 6,705,318 B1 | 3/2004 | Brain | 128/207.14 |
| 6,705,321 B2 * | 3/2004 | Cook | 128/207.15 |
| 6,792,948 B2 | 9/2004 | Brain | 128/207.14 |
| 6,799,574 B1 | 10/2004 | Collins | 128/207.15 |
| 6,877,512 B2 | 4/2005 | Imai et al. | 128/207.15 |
| 6,918,388 B2 | 7/2005 | Brain | 128/200.26 |
| 6,918,391 B1 | 7/2005 | Moore | 128/842 |
| 6,971,382 B1 | 12/2005 | Corso | 128/200.26 |
| 7,004,169 B2 | 2/2006 | Brain | 128/207.14 |
| D518,572 S | 4/2006 | Nasir | D24/110.5 |
| D518,890 S | 4/2006 | Nasir | D24/110.5 |
| 7,040,312 B2 | 5/2006 | Alfery et al. | 128/200.26 |
| 7,047,973 B2 | 5/2006 | Chang | 128/207.15 |
| 7,096,868 B2 | 8/2006 | Tateo et al. | 128/207.15 |
| 7,134,431 B2 | 11/2006 | Brain | 128/200.26 |
| 7,140,368 B1 | 11/2006 | Collins | 128/207.14 |
| 7,263,998 B2 | 9/2007 | Miller | 128/207.15 |
| RE39,938 E | 12/2007 | Brain | 128/207.15 |
| 7,305,985 B2 | 12/2007 | Brain | 128/200.26 |
| 7,357,845 B2 * | 4/2008 | Cook | 156/242 |
| 7,506,648 B2 | 3/2009 | Brain | 128/207.15 |
| D611,138 S | 3/2010 | Nasir | D24/110.5 |
| D615,188 S | 5/2010 | Nasir | D24/110.5 |
| D618,788 S | 6/2010 | Dubach | D24/110.5 |
| 7,762,261 B1 | 7/2010 | Fortuna | 128/207.14 |
| 7,806,119 B2 | 10/2010 | Nasir | 128/205.25 |
| 7,896,007 B2 | 3/2011 | Brain | 128/207.15 |
| 8,001,964 B2 | 8/2011 | McDonald et al. | 128/200.26 |
| 2001/0015207 A1 | 8/2001 | Pagan | 128/207.15 |
| 2001/0025641 A1 * | 10/2001 | Doane et al. | 128/207.15 |
| 2002/0010417 A1 | 1/2002 | Bertram | 604/96.01 |
| 2002/0010617 A1 | 1/2002 | Hamaguchi et al. | 705/10 |
| 2002/0078961 A1 | 6/2002 | Collins | 128/207.15 |
| 2002/0112728 A1 | 8/2002 | Landuyt | 128/207.15 |
| 2002/0170556 A1 | 11/2002 | Gaitini | 128/200.14 |
| 2003/0037790 A1 | 2/2003 | Brain | 128/207.14 |
| 2003/0066532 A1 | 4/2003 | Gobel | 128/207.15 |
| 2003/0101998 A1 | 6/2003 | Zocca et al. | 128/207.15 |
| 2003/0136413 A1 | 7/2003 | Brain et al. | 128/207.15 |
| 2003/0172925 A1 | 9/2003 | Zocca et al. | 128/202.22 |
| 2003/0172933 A1 | 9/2003 | Nimmo | 128/207.14 |
| 2004/0020488 A1 | 2/2004 | Kniewasser | 128/204.18 |
| 2004/0020491 A1 | 2/2004 | Fortuna | 128/207.15 |
| 2005/0016529 A1 * | 1/2005 | Cook | 128/200.24 |
| 2005/0051173 A1 | 3/2005 | Brain | 128/207.14 |
| 2005/0051175 A1 | 3/2005 | Brain | 128/207.14 |
| 2005/0066975 A1 | 3/2005 | Brain | 128/207.15 |
| 2005/0081861 A1 | 4/2005 | Nasir | 128/207.14 |
| 2005/0103345 A1 | 5/2005 | Brain | 128/207.15 |
| 2005/0104255 A1 * | 5/2005 | Mejlhede et al. | 264/328.1 |
| 2006/0081245 A1 | 4/2006 | Gould | 128/200.26 |
| 2006/0207601 A1 | 9/2006 | Nasir | 128/207.14 |
| 2008/0142017 A1 | 6/2008 | Brain | 128/207.15 |
| 2008/0308109 A1 | 12/2008 | Brain | 128/207.14 |
| 2010/0126512 A1 | 5/2010 | Nasir | 128/207.14 |
| 2010/0242957 A1 | 9/2010 | Fortuna | 128/202.22 |

FOREIGN PATENT DOCUMENTS

| | | | |
|---|---|---|---|
| AU | 200076743 | 5/2001 | A61M 16/04 |
| CA | 1 324 551 | 11/1993 | A61M 16/04 |
| CA | 2 191 749 | 12/1995 | A61M 16/01 |
| CA | 2 346 248 | 4/2000 | A61M 16/04 |
| CN | 1 166 138 | 11/1997 | A61M 16/00 |
| CN | 1 236 326 | 11/1999 | A61M 16/04 |
| CN | 1 351 509 | 5/2002 | A61M 16/04 |
| DE | 42 33 933 | 4/1993 | H02N 2/00 |
| DE | 43 30 032 | 4/1994 | H02N 2/00 |
| DE | 195 00 550 | 7/1996 | A61M 16/04 |
| DE | 299 02 267 | 7/1999 | A61M 16/06 |
| DE | 201 00 176 | 5/2001 | A61M 16/01 |
| DE | 202 06 692 | 8/2002 | A61M 16/00 |
| EP | 0 277 797 | 8/1988 | A61M 16/04 |
| EP | 0 389 272 | 9/1990 | A61M 16/04 |
| EP | 0 448 878 | 10/1991 | A61M 16/04 |
| EP | 0 586 717 | 3/1994 | A61M 16/04 |
| EP | 0 794 807 | 9/1997 | A61M 16/00 |
| EP | 0 834 331 | 8/1998 | A61M 16/04 |
| EP | 0 857 492 | 8/1998 | A61M 16/04 |
| EP | 0 875 260 | 11/1998 | A61M 16/04 |
| EP | 0 884 061 | 12/1998 | A61M 16/04 |
| EP | 0 911 049 | 4/1999 | A61M 16/04 |
| EP | 0 935 971 | 8/1999 | A61M 16/04 |
| EP | 1 125 595 | 8/2001 | A61M 16/04 |
| EP | 000067210-0001 | 8/2003 | |
| EP | 000067210-0002 | 8/2003 | |
| EP | 000197124-0001 | 6/2004 | |
| EP | 000197124-0002 | 6/2004 | |
| EP | 000197124-0003 | 6/2004 | |
| EP | 000197124-0004 | 6/2004 | |
| EP | 000197124-0005 | 6/2004 | |
| EP | 000197124-0006 | 6/2004 | |
| EP | 000180757-0001 | 7/2004 | |
| EP | 1504870 | * 2/2005 | |
| EP | 1 579 885 | 9/2005 | A61M 16/04 |
| EP | 000482195-0002 | 2/2006 | |
| EP | 000482195-0006 | 2/2006 | |
| EP | 1 875 937 | 1/2008 | A61M 16/04 |
| ES | 1 046 206 | 1/2000 | A61M 25/00 |
| FR | 2 094 264 | 1/1972 | C07C 31/00 |
| FR | 2 690 018 | 10/1993 | H02N 2/00 |
| FR | 2 760 186 | 9/1998 | A61F 2/30 |
| FR | 2 807 307 | 10/2001 | A47J 37/06 |
| FR | 2 827 482 | 1/2003 | A24B 1/10 |
| FR | 2 851 107 | 8/2004 | H04M 11/06 |
| GB | 1 402 255 | 8/1975 | A61M 25/00 |
| GB | 2 113 348 | 8/1983 | B06B 1/16 |

(56) References Cited

FOREIGN PATENT DOCUMENTS

| | | | |
|---|---|---|---|
| GB | 2 128 561 | 5/1984 | B60R 19/54 |
| GB | 2 168 256 | 6/1986 | A61M 16/04 |
| GB | 2 249 959 | 5/1992 | A61M 16/04 |
| GB | 2 267 034 | 11/1993 | A61M 25/02 |
| GB | 2 285 765 | 7/1995 | A61M 16/04 |
| GB | 2 317 342 | 3/1998 | A61M 16/04 |
| GB | 2 319 182 | 5/1998 | A61M 16/04 |
| GB | 2323292 | 9/1998 | A61M 16/04 |
| GB | 2 326 009 | 12/1998 | A61M 16/04 |
| GB | 2 330 312 | 4/1999 | A61M 16/04 |
| GB | 2 337 020 | 11/1999 | B29D 31/00 |
| GB | 2 359 996 | 9/2001 | A61M 16/04 |
| GB | 2 364 644 | 2/2002 | A61M 16/04 |
| GB | 2 373 188 | 9/2002 | A61M 16/04 |
| GB | 2 393 399 | 3/2004 | A61M 16/04 |
| GB | 2 404 863 | 2/2005 | A61M 16/04 |
| GB | 2 413 963 | 11/2005 | A61M 16/04 |
| GB | 2465453 | 5/2010 | A61M 16/04 |
| IE | 922073 | 12/1993 | A61M 16/00 |
| IT | 1224077 | 9/1990 | |
| JP | 3-236858 | 10/1991 | A61M 16/04 |
| JP | 6-277286 | 10/1994 | A61M 16/04 |
| JP | 2706567 | 1/1998 | A61B 1/00 |
| JP | 2007-509154 | 4/2007 | A61M 16/04 |
| TW | 224047 | 11/2004 | B29C 45/76 |
| WO | WO 94/17848 | 8/1994 | A61M 16/04 |
| WO | WO 95/09665 | 4/1995 | A61M 16/04 |
| WO | WO 97/12640 | 4/1997 | A61M 16/00 |
| WO | WO 98/06276 | 2/1998 | A23L 1/30 |
| WO | WO 98/24498 | 6/1998 | A61M 16/04 |
| WO | WO 98/50096 | 11/1998 | A61M 16/00 |
| WO | WO 99/24101 | 5/1999 | A61M 16/00 |
| WO | WO 00/30706 | 6/1999 | A61M 16/04 |
| WO | WO 99/44665 | 9/1999 | A61M 16/04 |
| WO | WO 00/09189 | 2/2000 | A61M 16/04 |
| WO | WO 00/61213 | 10/2000 | A61M 16/04 |
| WO | WO 01/13980 | 3/2001 | A61M 16/04 |
| WO | WO 0197890 | 12/2001 | A61M 16/00 |
| WO | WO 02/32490 | 4/2002 | A61M 16/04 |
| WO | WO 03/020340 | 3/2003 | A61M 16/04 |
| WO | WO 03018094 | 3/2003 | A61M 16/04 |
| WO | WO 2004/016308 | 2/2004 | A61M 16/04 |
| WO | WO2004/089453 | * 10/2004 | |
| WO | WO 2005/016427 | 2/2005 | A61M 16/04 |
| WO | WO 2005/041864 | 5/2005 | |

OTHER PUBLICATIONS

International Search Report and Written Opinion issued in corresponding application No. PCT/GB2011/051203, dated Jul. 12, 2011 (14 pgs).
US Official Action dated Feb. 14, 2013, issued in U.S. Appl. No. 29/407,461 (21 pgs).
International Search Report and Written Opinion issued in corresponding application No. PCT/GB2011/051203, dated Dec. 7, 2011 (15 pgs).
Combined Search and Examination Report issued in corresponding application No. GB1110775.2, dated Oct. 18, 2011 (8 pgs).
Combined Search and Examination Report issued in corresponding application No. GB0718849.3, dated Oct. 29, 2007 (4 pgs).
Combined Search and Examination Report issued in corresponding application No. GB0502519.2, dated Sep. 13, 2005 (6 pgs).
Extended European Search Report and Written Opinion issued in corresponding EPO applcation No. 07019251.3, dated Feb. 1, 2008 (8 pgs).
First Office Action issued in corresponding Chinese application No. 200480023382.4, dated Aug. 22, 2008 (15 pgs).
International Search Report and Written Opinion issued in corresponding PCT application No. PCT /GB2009/051574, dated Jun. 7, 2010 (28 pgs).
Combined Search and Examination Report issued in corresponding application No. GB1019839.8, dated Dec. 1, 2010 (2 pgs).
Combined Search and Examination Report issued in corresponding application No. GB 0418050.1, dated Nov. 29, 2004 (7 pgs).
Examination Report issued in corresponding application No. 09 756 353.0-1257, dated Aug. 17, 2012 (5 pgs).
Further examination as result of telephone conversation with examiner issued in corresponding EPO application No. 03 787 902.0 (1 pg).
Letter from IP Australia regarding third party application for re-examination dated Sep. 21, 2011 involving corresponding application No. 2008207412 (2 pgs).
Invitation to Pay Additional Fees with International Search Report issued in corresponding application No. PCT/GB2004/003481, dated Nov. 12, 2004 (8 pgs).
Notice for Reasons for Rejection issued in corresponding Japanese application No. 2006/523053, dated Nov. 8, 2010, with English translation (4 pgs).
International Search Authority issued in corresponding PCT application PCT/GB03/03577 dated, Dec. 9, 2003 (5 pgs).
International Search Report issued in corresponding PCT application PCT/GB03/03577 dated Aug. 14, 2003 (9 pgs).
"The Development of the Laryngeal Mask—a Brief History of the Invention, Early Clinical Studies and Experimental Work from Which the Laryngeal Mask Evolved" A.I.J. Brain, European Journal of Anesthesiology, 1991, Supplement 4, pp. 5-17.
PCT International Search Report, dated Jan. 14, 2009 (20 pgs).
Japanese Office Action (no translation) issued in related application No. 2012-38633, dated Apr. 23, 2013 (2 pgs).
Notice of Allowance issued in related application serial No. 29/407,461, dated Jun. 12, 2013 (26 pgs).
Office Action issued in Application No. 29/353,658 dated Aug. 19, 2011 (10 pgs).
International Search Report and Written Opinion issued in Applicant's corresponding UK Patent Application Serial No. GB0817776.8.
Notice of Allowance issued in related application No. 29/449,900, dated Jul. 24, 2013 (11 pgs).

* cited by examiner

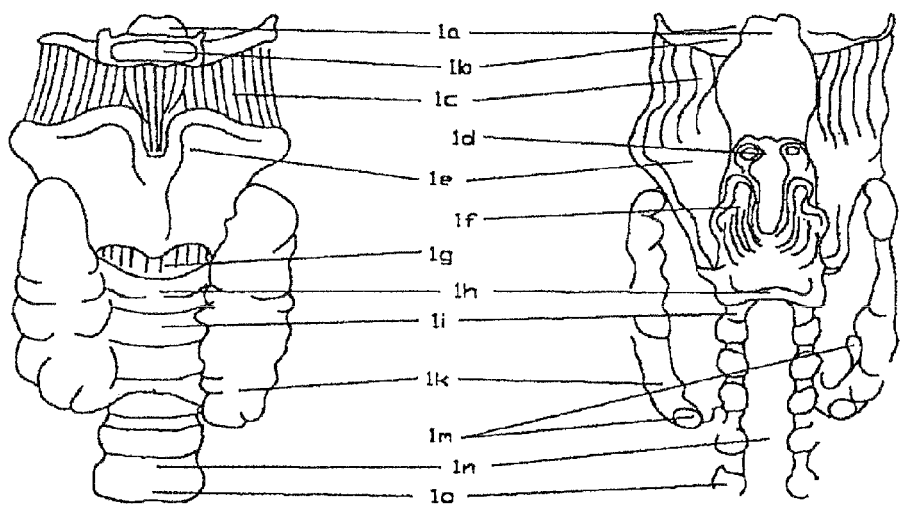
Fig. 1(a) Anterior View    Fig. 1(b) Posterior View
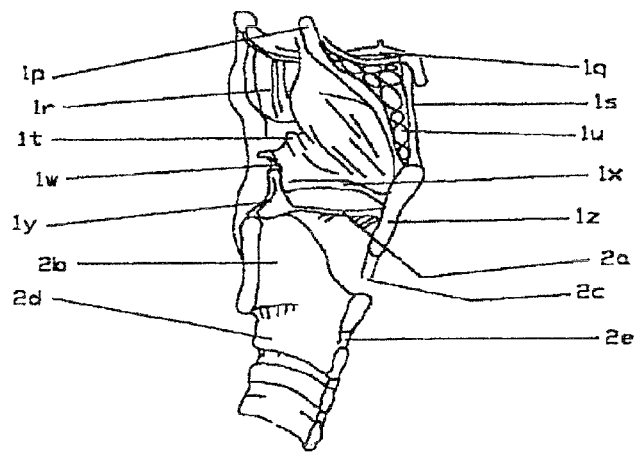
Fig. 1(c) Sagittal Section

FRONTAL VIEW OF NLA

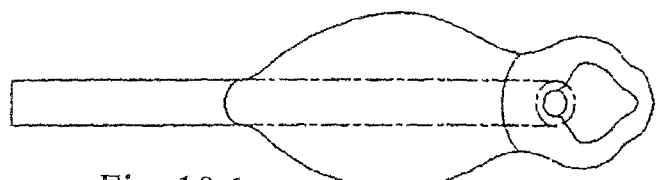
Fig. 10.1
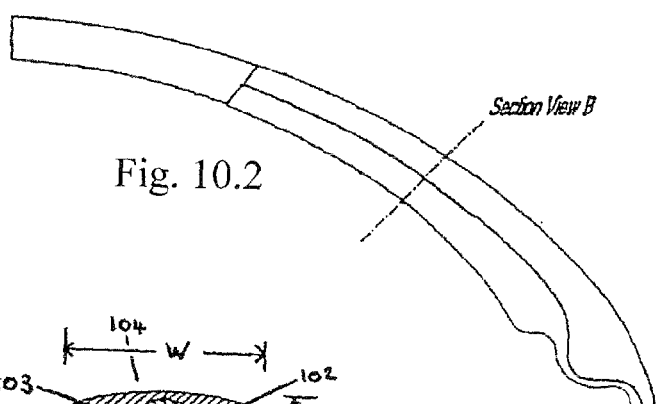
Fig. 10.2
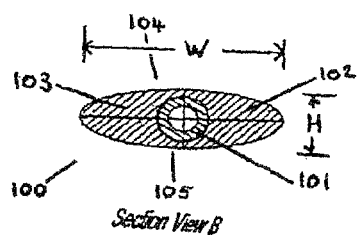
Fig. 10.3
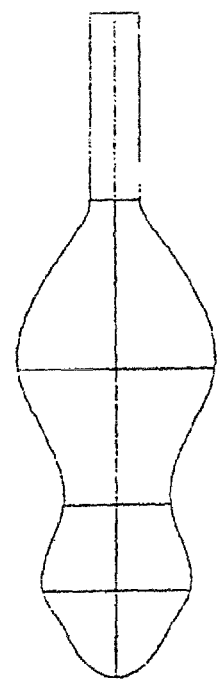
Developed view C
(Folded Flat)
Fig. 10.5
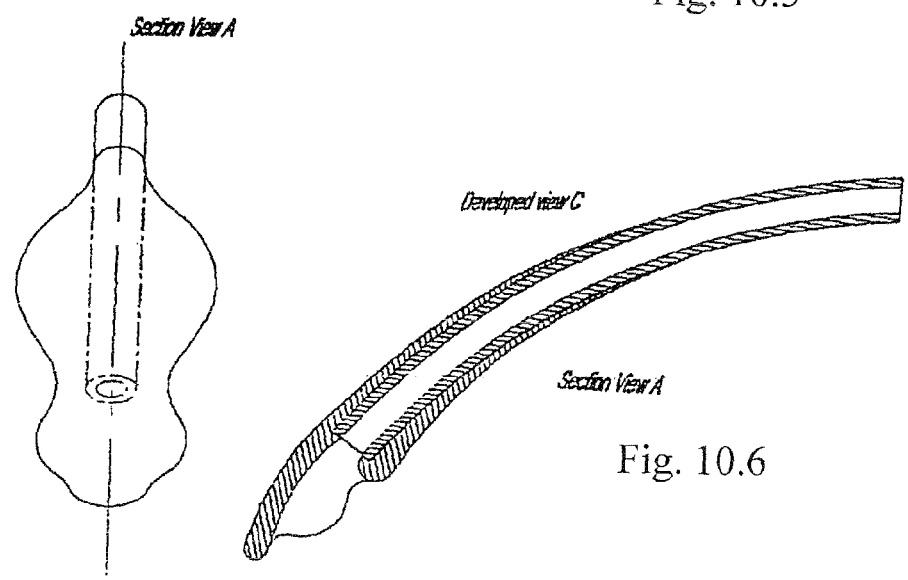
Fig. 10.4
Fig. 10.6

FRONTAL VIEW

FRONTAL VIEW

LATERAL VIEW

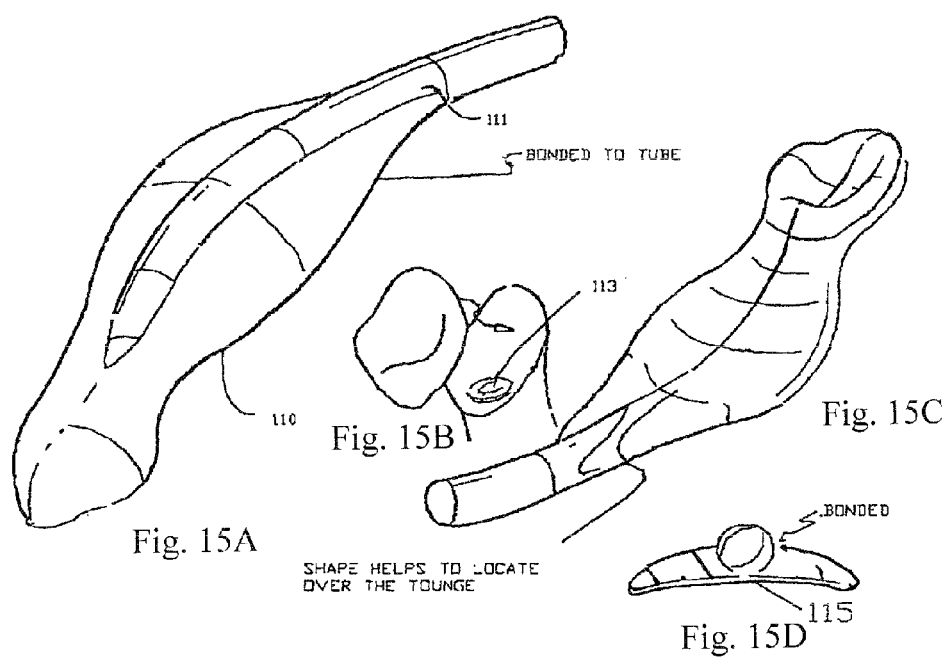

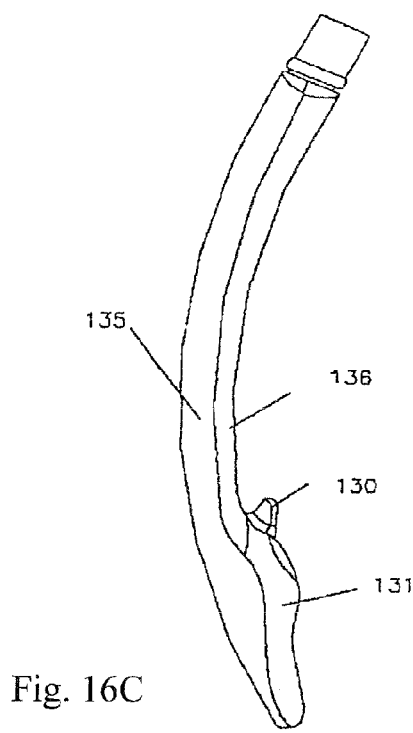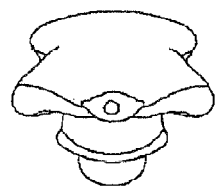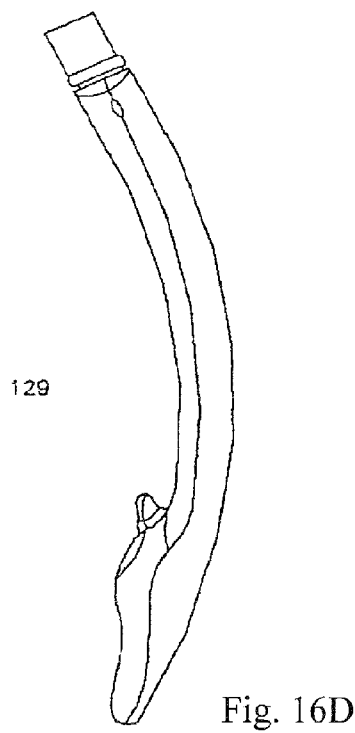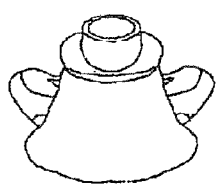
Fig. 16C
Fig. 16E
Fig. 16D
Fig. 16F

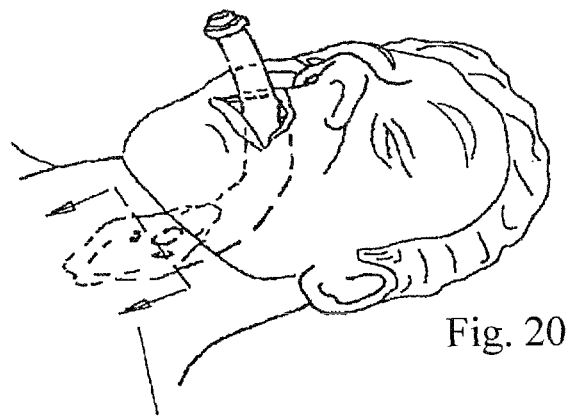
DEVICE IN SITU
Fig. 20
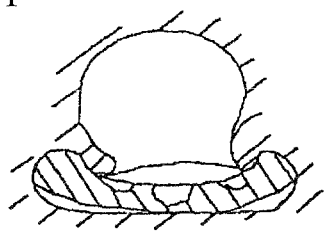
Fig. 21   SECTION VIEW IN DIRECTION SHOWN

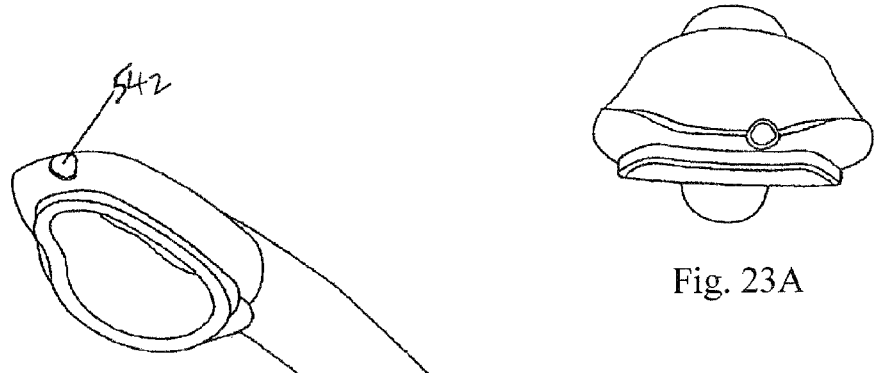
Fig. 23A
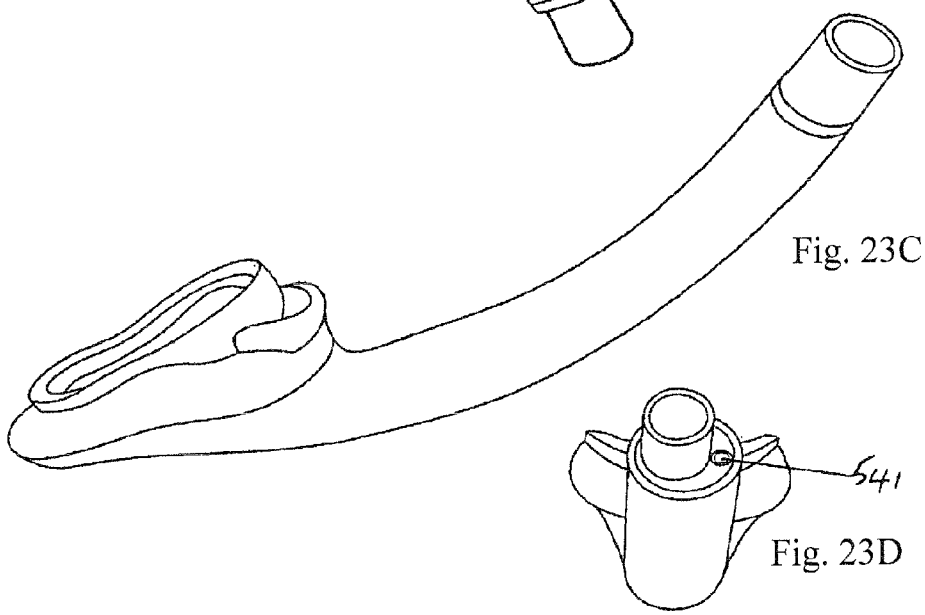
Fig. 23B
Fig. 23C
Fig. 23D

Fig. 25A
Fig. 25B
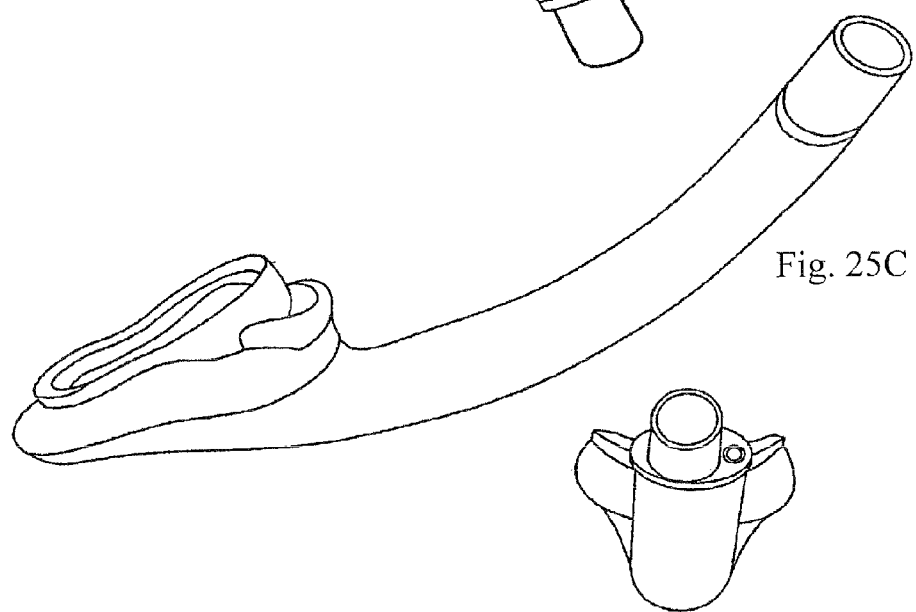
Fig. 25C
Fig. 25D

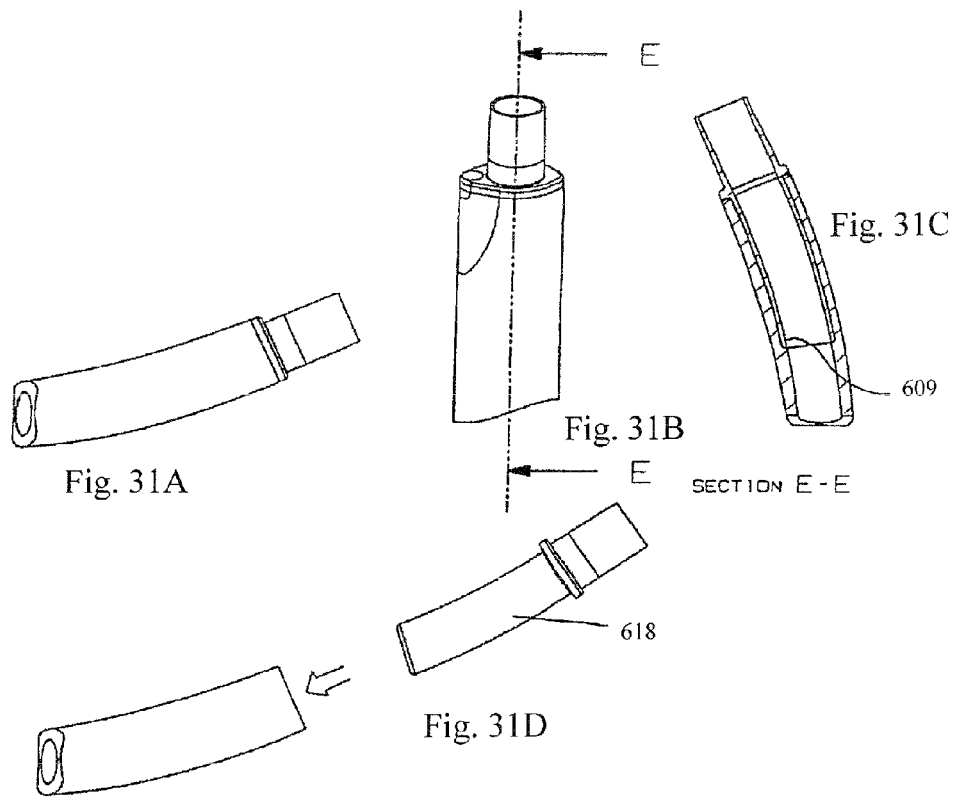
Fig. 31A   Fig. 31B   Fig. 31C   SECTION E-E   Fig. 31D
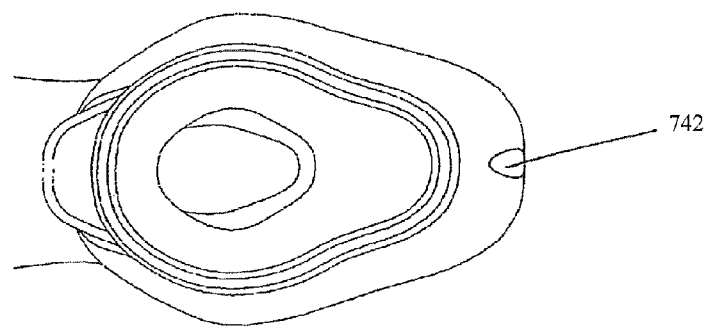
Fig. 32

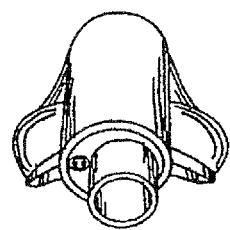
Fig. 46
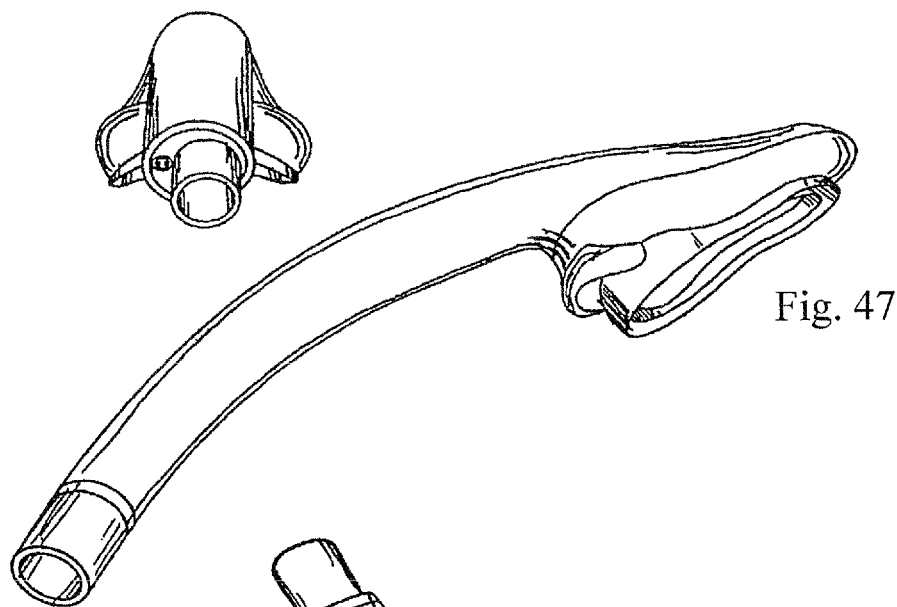
Fig. 47
Fig. 48
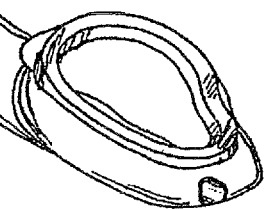
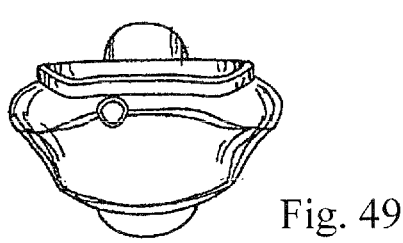
Fig. 49

Fig. 60
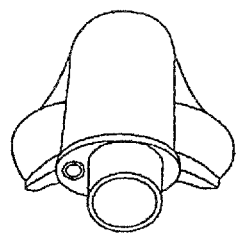
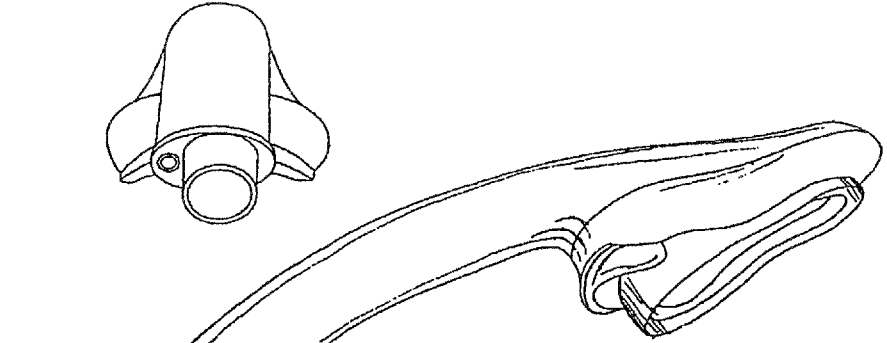
Fig. 61
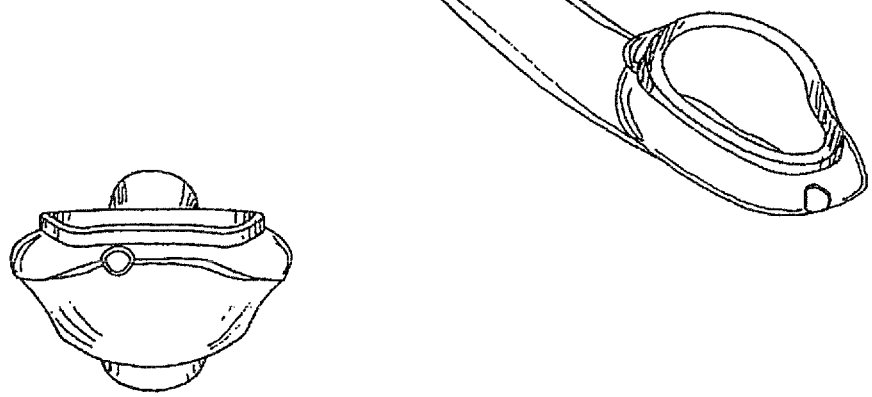
Fig. 62
Fig. 63

METHOD OF MANUFACTURING AN AIRWAY DEVICE

CROSS REFERENCE TO RELATED APPLICATIONS

This application is a divisional of U.S. patent application Ser. No. 10/983,199, filed Nov. 5, 2004 now U.S. Pat. No. 8,215,307, which is a continuation-in-part of PCT International Patent Application Serial No. PCT/GB2003/003577, filed Aug. 14, 2003, designating the United States. Priority is also claimed from PCT International Patent Application Serial No. PCT/GB2004/003481, filed Aug. 13, 2004 and European Utility Design Application Serial Nos. 000180757, filed May 7, 2004 and 000197124, filed Jun. 24, 2004.

FIELD OF THE INVENTION

This invention relates to an anatomically oriented, simple but versatile, improved airway device. It is particularly applicable, but in no way limited, to devices used in the administration of anaesthetics to a patient breathing spontaneously during a surgical procedure. The present invention relates in particular to a laryngeal airway device. More specifically, the present invention relates to reduced cost, disposable laryngeal airway device, and to methods of fabricating such airway device.

BACKGROUND TO THE INVENTION

Examples of devices currently used in spontaneously breathing anaesthetized patients, during recovering after anaesthetics, weaning of a certain group of patients in intensive care, or during resuscitation to provide a clear and hands-free airway are:—
a) Guedel airway with various types of face masks.
b) Cuffed Oro-pharyngeal airway.
c) Laryngeal Mask Airway (LMA), reinforced LMA, intubating LMA and a modified Intavent LMA for ENT and dental anaesthesia.
d) Airway Management device.
e) Combi-tube.
f) Self-retaining nasopharyngeal airway.
g) Cuffed or non-cuffed Endotracheal tubes, R.A.E. endotracheal tube.
h) Supraglottic oropharyngeal airway.
i) Tracheostomy and mini-trache tubes.
j) etc etc All of the above mentioned devices carry significant and varying degrees of co-morbidity involving not only unacceptable concurrent physiological changes but also temporary and/or permanent anatomical/structural damage. Many cases of mortality caused directly or indirectly as a result of the use of such devices have also been reported.

Probably the most successful design variant is the inflatable laryngeal airway device, variants of which have been used to administer anaesthetic gases since 1988.

A brief history of the development of such airway device is described in a review by A I J Brain in the European Journal of Anaesthesiology 1991, Supplement 4, pages 5 to 17 inclusive. The entire text of this review is hereby incorporated by reference and is intended to form an integral part of this disclosure.

If the respiratory tree is seen as a tube terminating at the glottis, and the objective is to make a simple connection between this tube and an artificial tube for supplying gas under low pressure to the bronchial tree, it would seem logical to form a direct end-to-end junction between the two tubes. The face mask forms an end-to-end junction indeed, but with the wrong orifice, while the endotracheal tube meets the correct orifice but goes too far by penetrating into the lumen, so that the junction is effected within it, instead of at its rim. The undesirable aspects of intubation of the trachea result from the fact that, to effect a seal, pressure is applied to an epithelial surface whose important and highly specialized functions are thus compromised and that by penetration of the vocal cords, effective coughing is rendered impossible, upper-airway architecture is distorted and unwanted reflex response are not only provoked by laryngoscopy needed prior to intubation but also by presence of endotracheal tube in the trachea. Such laryngeal masks have been used in anaesthetic practice since 1988 and many reports of co-morbidity and/or mortality directly or indirectly related to their use have been reported. Complications and/or morbidity are caused by hyperinflation and extraluminal pressure impact onto the soft tissue and cartilagenous structures in contact with the hyper-inflated cuff.

Several attempts have been made to improve this type of airway device but they still suffer from a number of serious inherent drawbacks. Firstly, they require inflation of the cuff to be effective and furthermore anaesthetic gas (nitrous oxide) can diffuse into the cuff, expanding the air in the cuff, thus increasing the cuffs extraluminal pressure significantly, and as a result, put considerable pressure on the sensitive tissues of Laryngopharynx. Secondly, these masks have a tendency to move from side to side or rotate about their longitudinal axis as a force is applied to the proximinal end of the tube, attached to the anaesthetic equipment. It will be appreciated that if such a device is to lie perfectly symmetrically in use then the airway tube will be aligned with the patient's nose. However, any rotational or sideways movement of the airway tube will have the potential to affect the seal that the airway device makes around the laryngeal inlet.

Several types of airway device have been described in the patent literature. For example, U.S. Pat. No. 5,976,072 (Johns Hopkins University) describes a fiberoptic endotracheal intubation device. However, this relies on an inflatable oro-pharyngeal cuff that suffers from the disadvantages referred to above.

U.S. Pat. No. 5,865,176 (O'Neil) and GB2,319,182 (VBM Medizintechnik GmbH) describe airway devices having a double inflatable cuff arrangement, a first inflatable cuff for providing a seal in the patient's pharynx and a second inflatable cuff for providing a seal in the patient's oesophagus. This arrangement compounds the problem of tissue damage as set out above.

In a contrasting arrangement, GB2,373,188 (Smiths Group plc) describes an inflatable laryngeal mask with a tear-shaped blocker plate designed to prevent the mask blocking the epiglottis during insertion. This only goes to emphasise the potential downsides of a tubular inflatable mask of this type.

Finally, in WO00/61213 (Brain) there is described a disposable laryngeal mask airway device with an inflatable cuff. However, not only does this suffer from all the disadvantages of an inflatable cuff device, but it is formed from multiple components, adding to the cost and complexity of manufacture.

Collectively, these represent the closest prior art known to the applicant.

It is an object of the present invention to overcome or mitigate some or all of these problems.

It is a further object of the present invention to provide an airway device that is both simple and effective to use and cost-effective to manufacture.

Where a single use item is concerned, cost of manufacture, and minimising this cost, is important. A further objective of the present invention is therefore to provide cost-effective methods for manufacturing airway devices that enable the unit cost per item to be minimised.

It is also an object of this invention to satisfy the requirements of clinical situations where a buccal cavity stabiliser would not enhance, but impede the operation. For example in many ophthalmalogical, and maxillofacial or dental surgery situations the use of a reinforced tube is preferable, as the tube can flexibly moved to one side to continue to provide an airway for the patient, whilst not interfering with the operation.

In summary, where it might be advantageous to have an airway device with a buccal cavity stabiliser in some applications, we have discovered that there are several applications where this is disadvantageous. In fact there are several applications where it is just not practical to have a buccal cavity stabiliser.

SUMMARY OF THE INVENTION

A first aspect of the present invention provides an airway device as described in the accompanying claims.

Accordingly, according to a first embodiment, there is provided an airway device for human or animal use comprising an airway tube having a distal end and a proximal end, the distal end of which is surrounded by a laryngeal cuff, characterised in that the laryngeal cuff is adapted to form an anatomical fit over the laryngeal inlet of a patient, and to cover and form a substantially gas-tight seal with the laryngeal inlet of the patient, the device further comprising a buccal cavity stabiliser located on or around the airway tube between the laryngeal cuff and the proximal end of the tube, said buccal cavity stabiliser being adapted to nest with the anterior aspect of the patient's tongue, the size, shape, softness and configuration of the buccal stabiliser being adapted to provide stability and to prevent rotational or side-to-side movement of the airway tube in use. This buccal cavity stabiliser may be formed from the same material as the cuff or from a different material and assists in locating and maintaining the position of the device in use.

Airway devices according to the present invention will be referred to in the following text by the shorthand abbreviation NLA (Nasir Laryngeal Airway Device), named after the inventor.

Preferably the cuff is non-inflatable and is pre-formed in a shape adapted to form an anatomical fit over the laryngeal framework of a patient. The aryepiglotlic fold, arytenoid & corniculate cartilages. Interarytenoid fold and piriform fossae make the laryngeal structure anatomically an irregular structure. The terms laryngeal inlet, laryngeal framework and laryngeal structure are used interchangeably in the following description. These terms relate to the larynx area of a patient and the surrounding tissue, folds and cartilages as illustrated in FIG. 1.

The device is a mirror image of the laryngopharyngeal framework thus providing an anatomical fit to the irregular structural framework of the laryngopharynx. Incorporation of an anatomically designed cup/cuff also offers advantages over the use of an inflatable cuff which will exert a significant extra luminal pressure not only well beyond the pressure (22-26 mm/Hg) at which the soft tissue surface is being supplied but will also distort, compress, dislocate, dislodge or fracture the structures in contact with the cuff. Extraluminal pressure is exerted onto the structure of laryngopharynx not only by the cuff's repeated inflation with air to create an adequate seal, which is achieved at the cost of distortion of the surrounding structures by undue pressure caused by a rounded, smooth-faced tensed cuff, and also increased in situ by absorption of nitrous oxide (anaesthetic gas) into the cuff's lumens. This can increase cuff pressure beyond 100 mmHg immediately, rising beyond 200 mmHg within an hour's use, which is well above the normal intracellular pressure or the pressure at which the blood capillaries supply the laryngopharyngeal structures.

Preferably the laryngeal cuff is pre-formed, pre-inflated with air or pre-filled with a suitable fluid.

Preferably the face of the laryngeal cuff adapted to form an anatomical fit over the laryngeal framework of a patient incorporates protuberances designed to form a good seal with the pyriform fossae and aryepiglottic folds of the laryngeal framework of the patient. It is also preferred that the face of the laryngeal cuff incorporates protuberances designed to form a good seal with the valleculae, epiglottis, aryepiglottic folds, pyriform fossae and around the anterior aspect of thyroid & cricoid cartilages. The seal around these features may also be reinforced or enhanced by one or more feather-like flanges located around part or all of the perimeter of the laryngeal cuff. This design enables increased seal pressure that will allow well in excess of 30 cm $H_2O$ to be obtained.

In a further preferred embodiment the face of the laryngeal cuff adapted to fit snugly over the laryngeal inlet of a patient incorporates grooves designed to allow passage of vital arteries, veins and nerves supplying the laryngeal structure.

In a particularly preferred embodiment the distal tip of the laryngeal cup is so sized and shaped as to remain above the upper oesophageal sphincter in use. Most preferably the distal tip of the laryngeal cup is substantially concave in shape.

In an alternative embodiment the laryngeal cup portion is pre-formed from a material which is adapted to absorb a liquid such as water/mucous/blood or similar matter to swell to conform to the anatomical mucocartilagenous framework of laryngeal inlet e.g. material like CRM (cotton rayon mix)—used to manufacture TAMPAX® (tampon) or Compressed Gel Foam5.

Preferably the buccal cavity stabiliser has a first, ventral face in substantially the same plane as the plane of the open face of the laryngeal cuff and the first face of the buccal cavity stabiliser is substantially concave in shape. This assists the operator with inserting the device into the patient and with bringing the buccal cavity stabiliser into contact with the patient's tongue.

Preferably the buccal cavity stabiliser extends from the proximal end of the laryngeal cuff towards the proximal end of the airway tube such that the cuff and the buccal cavity stabiliser are of integral construction. This provides a smooth, elegant device with an appealing and practical design.

Preferably the buccal cavity stabiliser is non-uniform in its width W, having a wide point located at a point intermediate the laryngeal cuff and the proximal end of the airway tube, and more preferably the wide point of the buccal cavity stabiliser is closer to the laryngeal cuff than to the proximal end of the airway tube. This arrangement places the widest or broadest region of the stabiliser in contact with the base of the patient's tongue when in use.

Preferably the ratio of the width W of the buccal cavity stabiliser at its widest point to the height H of the buccal cavity stabiliser at that same point is 2.7±10%.

Advantageously the face of the buccal cavity stabiliser which comes into contact with the patient's tongue may be roughened to increase friction of the stabiliser with the tongue in use.

In a further alternative embodiment the buccal cavity stabiliser is adjustable in size, for example wherein the buccal cavity stabiliser is formed from a unit, at least part of which is slidably mounted with respect to the airway tube.

In a particularly preferred embodiment the buccal cavity stabiliser is formed as an integral part of the airway tube, and further preferably the buccal cavity stabiliser, the airway tube and the laryngeal cuff are all formed as an integral unit.

The Shore hardness of the various, parts, portions or components is an important feature of the invention. For example, the laryngeal cuff is preferably formed from a material with a Shore hardness on the A scale of 40 or less and more preferably between 0 to 20, and most preferably between 4 to 12.

Preferably the laryngeal cuff and a front, ventral part of the buccal cavity stabiliser are formed from a material of substantially the same Shore hardness. This simplifies construction and ensures that all portions of the device that come into firm contact with the patient's soft tissue are relatively soft.

In a further preferred embodiment a back or dorsal part of the device and a front or ventral part of the device are formed from materials of different Shore hardness. This enables the dorsal portion to be made of a firmer material than the ventral portion.

Preferably the back or dorsal part of the device is formed from a material of Shore hardness less than 60 on the A scale, more preferably between 25 to 45, and most preferably between 30 to 40.

It should also be appreciated that the laryngeal cuff can be inflatable. Whilst this is not ideal, it still represents a significant improvement over and above prior art inflatable masks.

Preferably the device further incorporates a gastric tube passageway extending from the lip of the cuff to the proximal end of the device.

According to a second aspect of the present invention there is provided a method of manufacturing an airway device comprising the steps of:—
(a) forming mouldings of a first part of the device and a second part of the device;
(b) bonding the first part to the second part around a connector.

This represents a considerable simplification over the manufacture of prior art devices, which are typically multi-component in design.

Preferably the first part is a front, ventral part of the device incorporating the face of a laryngeal cuff and the second part is a back, dorsal part in which the first and second parts are formed from materials of the same or different Shore hardnesses.

According to a third aspect of the present invention there is provided a method of manufacturing an airway device comprising an airway tube, a laryngeal cuff and a buccal cavity stabiliser comprising forming the device as a one-piece plastics moulding, preferably wherein the device is formed by the technique of injection moulding.

It has also unexpectedly been discovered that a stabiliser, whilst still desirable, is not essential to achieve a good gas-tight seal between the cuff and the laryngeal inlet of the patient. Since a buccal cavity stabiliser adds both weight and cost there are positive advantages in eliminating this feature from the design. Weight and cost are both important features, particularly where the item is intended as a single use or disposable item.

Accordingly, according to a fourth embodiment there is provided an airway device for human or animal use comprising an airway tube having a distal end and a proximal end, the distal end of which is surrounded by a laryngeal cuff, wherein the cuff is non-inflatable and is pre-formed in a shape such that a face region of the cuff is adapted to fit snugly over the laryngeal inlet of a patient, and wherein the external profile of the tube is substantially uniform between the distal end of the tube where it starts to meet the cuff and the proximal end of the tube, and wherein the face region of the cuff is formed from a material with a Shore hardness on the A scale of between 0 to 30.

Such an airway device is both efficient in operation and cost-effective to manufacture.

Preferably the face region of the cuff is formed from a material of Shore hardness on the A scale of between 0 and 20 and more preferably 0 to 5. Preferably the profile of the airway tube is substantially circular.

In an alternative embodiment the profile of the airway tube is substantially elliptical.

Preferably the device further comprises a gastric tube passageway extending from the distal end of the airway tube to the proximal end of the cuff.

Preferably the gastric tube passageway is housed substantially within the body of the device.

Preferably the distal end exit of the gastric tube passageway exits the cuff centrally, that is along the line of the central longitudinal axis of the device.

Alternatively the distal end exit of the gastric tube passageway may be displaced to one side of the central longitudinal axis of the device.

If the end exit of the gastric tube passageway is displaced it is preferred that the distal end exit of the device is displaced to the right of the central longitudinal axis of the cuff, as viewed from the open face of the cuff, in other words to the right-hand side of the patient when the device is in use. This is for ease of manufacture.

In a particularly preferred embodiment the device further comprises one or more flexible flanges extending around the opening in the face region of the cuff.

Preferably the flexible flanges extend substantially around the entire circumference of the opening in the cuff.

Preferably a plurality of flanges are provided said flanges being spaced apart radially around the opening one from another such that the flanges are substantially concentric.

Advantageously said device further comprises a connector adapted to connect the proximal end of the airway tube to a gas supply.

Preferably said connector extends into said airway tube and at least part way along the length of said airway tube to act as a bite protector to prevent a patient from constricting the airway tube by biting on it.

Preferably said connector fits into an internal annular recess at the proximal end of the airway tube such that the diameter, or internal cross-section of the airway tube where the tube is non-circular internally, remains substantially constant along the length of the tube when the connector is in place.

Preferably the distal end of the connector abuts in use a shoulder in the airway tube to prevent the connector from passing into the airway tube beyond a certain point. This provides a positive fit for the connector which seats on a shoulder or recess within the tube, and results in lower resistance to airflow through the device.

Preferably the face of the laryngeal cuff is adapted to form an anatomical fit over the laryngeal inlet of a patient incorporates protuberances designed to form a good seal with the pyriform fossae and aryepiglottic folds of the laryngeal inlet of the patient.

Preferably the face of the laryngeal cuff adapted to form an anatomical fit over the laryngeal inlet of a patient incorporates protuberances designed to form a good seal with the valleculae, epiglottis, aryepiglottic folds, pyriform fossae and around the anterior aspect of thyroid & cricoid cartilages. The distal tip of the device positions itself into the recess created by the posterior aspect of the lower larynx below the posterior cartilages, above the opening of the oesophagus, not only to help create an airway seal but also to act as a physical wedge to prevent the possibility of regurgitation.

Preferably the face of the laryngeal cuff adapted to fit anatomically over the laryngeal framework of a patient incorporates grooves designed to allow passage of vital arteries, veins and nerves supplying the laryngeal framework.

Preferably the distal tip of the laryngeal cup is so sized and shaped as to remain above the upper oesophageal sphincter in use.

Preferably the distal tip of the laryngeal cup is substantially concave in shape.

Preferably the face of the laryngeal cuff and the airway tube are formed from materials of different Shore hardness.

In an alternative embodiment the face of the laryngeal cuff and the airway tube are formed from material of substantially the same Shore hardness.

Preferably the airway tube together with the back or dorsal part of the cuff are made from material of one Shore hardness and the face of the cuff is made from a material of a different Shore hardness, such that the face of the cuff is made of a softer material than the airway tube and the back or dorsal part of the cuff.

According to a further aspect of the invention there is provided a method of manufacturing an airway device suitable for human or animal use, said airway device comprising an airway tube having a distal end and a proximal end, the distal end of which is surrounded by a non-inflatable laryngeal cuff, said method comprising the steps of:
(i) providing a mould, the mould including interior walls defining an interior volume which defines the shape of the airway device;
(ii) introducing a liquid plastics material into the hollow interior volume of the mould;
(iii) optionally introducing a second liquid plastics material into said mould where it is required that the airway device is made from materials of different Shore hardness;
(iv) allowing the plastics material to solidify;
(v) removing the airway device from the mould.

Preferably said method also comprises the step of inserting into said mould a connector suitable for connecting to an anaesthetic gas supply, such that, after the moulding process is complete, the connector becomes attached to the airway device.

According to a further aspect of the invention there is provided a method of manufacturing an airway device suitable for human or animal use, said airway device comprising an airway tube having, a distal end and a proximal end, the distal end of which is surrounded by a non-inflatable laryngeal cuff, said method comprising the steps of:—
(i) providing an airway tube;
(ii) providing a mould, said mould including interior walls defining an interior volume which defines the shape of a laryngeal cuff;
(iii) inserting said airway tube into said mould;
(iv) introducing a liquid plastics material into the hollow interior volume of the mould;
(v) optionally introducing a second liquid plastics material into said mould where it is required that the cuff of the airway device is made from materials of different Shore hardness;
(vi) allowing the plastics material to solidify;
(vii) removing the airway device from the mould.

Preferably said airway tube is formed by an extrusion process.

In a still further aspect of the present invention there is provided method of manufacturing an airway device suitable for human or animal use, said airway device comprising an airway tube having a distal end and a proximal end, the distal end of which is surrounded by a non-inflatable laryngeal cuff, said method comprising the steps of:—
(i) providing a mould, the mould including interior walls defining an interior volume which defines the shape of a laryngeal cuff;
(ii) introducing a liquid plastics material into the hollow interior volume of the mould;
(iii) optionally introducing a second liquid plastics material where it is required that the airway device is made from materials of different Shore hardness;
(iv) allowing the plastics material to solidify;
(v) removing the airway device from the mould;
(vi) providing an airway tube;
(vii) bonded said airway tube to said laryngeal cuff.

In a still further aspect of the invention there is provided a method of manufacturing an airway device suitable for human or animal use, said airway device comprising an airway tube having a distal end and a proximal end, the distal end of which is surrounded by a non-inflatable laryngeal cuff, said method comprising the steps of:—
(i) providing an airway tube;
(ii) providing a mould, said mould including interior walls defining an interior volume which defines the shape of a laryngeal cuff and which substantially encapsulates the airway tube;
(iii) inserting said airway tube into said mould;
(iv) introducing a liquid plastics material into the hollow interior volume of the mould, to form the back of the cuff and substantially cover the rigid airway tube
(v) optionally introducing a second liquid plastics material into said mould where it is required that the cuff of the airway device is made from materials of different Shore hardness;
(vi) allowing the plastics material to solidify;
(vii) removing the airway device from the mould.

Preferably said airway tube is formed by an extrusion process.

BRIEF DESCRIPTION OF THE DRAWINGS

The invention will now be described, by way of example only, with reference to the accompanying drawings in which:—

FIGS. 1A to C illustrate various views of the laryngeal cartilages and ligaments. This illustration is derived from Tortora G. J., Grabowski G, Reynolds S. Principles of Anatomy and Physiology. John Wiley, 10th Ed, 2003. Pg 781, the text and illustrations of which are herein imported by reference;

FIGS. 10.1 to 10.6 show various plan, side and cross-sectional views of a further embodiment of the present invention.

FIGS. 15A, B, C and D illustrate a number of perspective, cross-section and exploded diagram views of an airway device, showing that the airway tube itself may stand proud of the main body of the device.

FIGS. 16A to F show front, back, side and end elevational views of a further preferred embodiment of the present invention;

FIGS. 18, 19 and 20 show various diagrammatic cross-sectional and isometric views of devices according to the present invention in situ in a human patient;

FIG. 21 illustrates a section along the line Y-Y shown in FIG. 20;

FIGS. 23A to D illustrate various perspective views of the embodiment shown in FIG. 23;

FIGS. 25A to D illustrate various perspective views of the embodiment shown in FIG. 25;

FIGS. 31A to D illustrate a connector which can also act as a bite protector;

FIG. 32 illustrates a front elevational view of a laryngeal cuff in which the gastric tube passageway exits on the midline or centrally from the tip of the cuff;

FIGS. 40 to 49 show front, back, side and end elevational views of another further embodiment of the present invention;

FIGS. 57 to 63 show front, back, side and end elevational views of another further embodiment of the present invention;

DESCRIPTION OF THE PREFERRED EMBODIMENTS

Embodiments of the present invention are described below by way of example only. These examples represent the best ways of putting the invention into practice that are currently known to the applicant although they are not the only ways in which this could be achieved.

Figure 2:
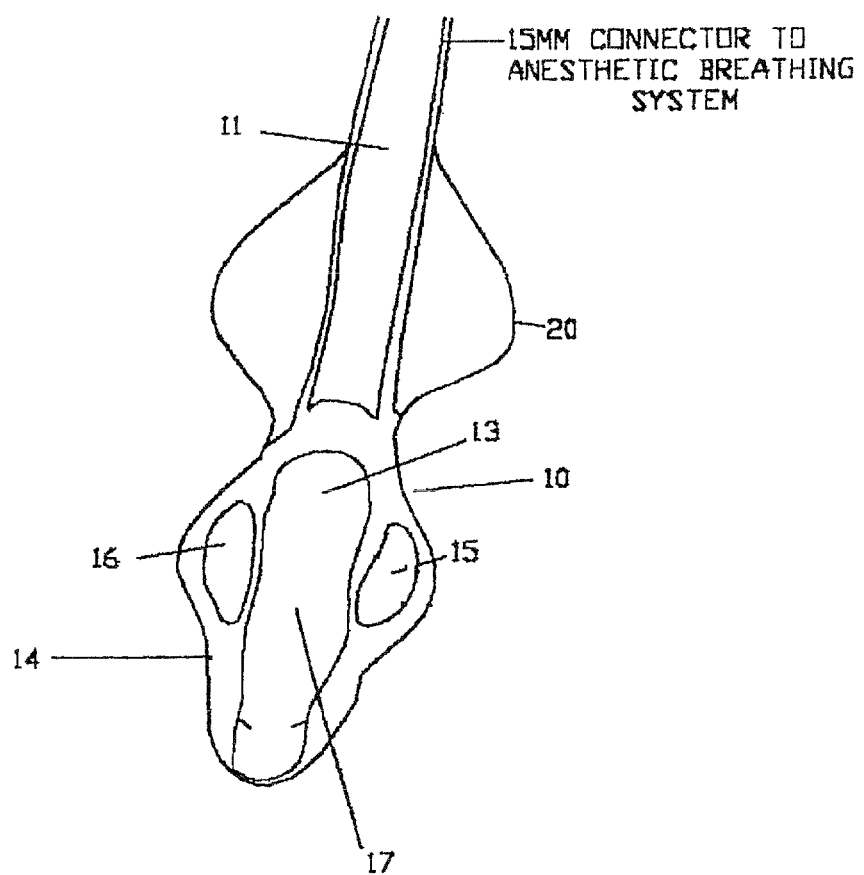
FIGS. 2 and 3 illustrate in plan view two embodiments of the present invention.

Referring to FIG. 2, this illustrates the distal end of a mask device according to a first embodiment of the present invention, generally shown as 10. This comprises an airway tube 11, which at its proximal end 12 (not shown) terminates in a 15 mm or other connector suitable for connection to an anaesthetic breathing system of conventional type. Formed around the distal end 13 of the airway tube is a laryngeal cuff or cup 14 adapted in its shape and contours to correspond with the larynx inlet region of a patient. In this context the terms cuff and cup have an equivalent meaning. They refer to the element of the device at the distal end of the airway tube that is adapted to cover and form a seal with the laryngeal inlet of the patient. In the context of this description, the term proximal means the end of the device, or portion thereof, closest to the connection to the anaesthetic breathing system. The term "distal" means the end of the device, or portion thereof, furthest from the anaesthetic breathing system.

Laryngeal cuffs, in general, are well known to the specialist and the anatomy of the laryngeal inlet region of a human are shown in some detail in FIGS. 1A, B and C. The particular cuff shown in FIG. 2 incorporates in the cuff face pronounced and discernable bulges or protruberances 15, 16 designed to form a good seal with the piriform fossae and aryepiglottic folds. It will be appreciated that the outbulgings in the cuff at 15 and 16 are positioned antero-laterally to give an anatomical seal by fitting into the piriform fossae and aryetriglottic folds. Thus, in side elevation, the face of the cuff is not a flat planar surface but includes regions that protrude above the general plane of the cuff face. Additionally, there may optionally be regions which lie below the general plane of the cuff face. These shapings and the general size, shape and configuration of the surface of the cuff face around opening 17 are an important feature of the invention. Alternative shapes for the face of the cuff are shown in FIGS. 3, 5, 10, 11, 12, 17 and 18 and are described in more detail below.

The device may be constructed from any suitable plastics material as selected by the materials specialist. Latex-free medical grade silicone rubber is one preferred material. The cuff should be soft in texture to avoid undue damage to the surrounding tissue. Other suitable materials for construction of this type of device include, but are not limited to, Poly Vinyl Chloride (PVC), Thermoplastic Elastomers such as the styrenic block copolymers (eg Styrene Butadiene Styrene (SBS), Styrene Ethylene Butylene Styrene (SEBS)), and Thermoplastic Olefin Blends (TPO), Thermoplastic Poly-Urethanes (TPU), Copolyester (COPE), Polyether Block Amides (PEBAX) and foamed versions thereof, where appropriate.

A further important factor involved in the choice of a suitable material is transparency. Ideally the material or materials of construction should be substantially clear or transparent. This enables the anaesthetist or operator to see the inner lumen of the airway to check for blockages or other problems. Such transparent materials are known to the materials specialist.

Figure 4:
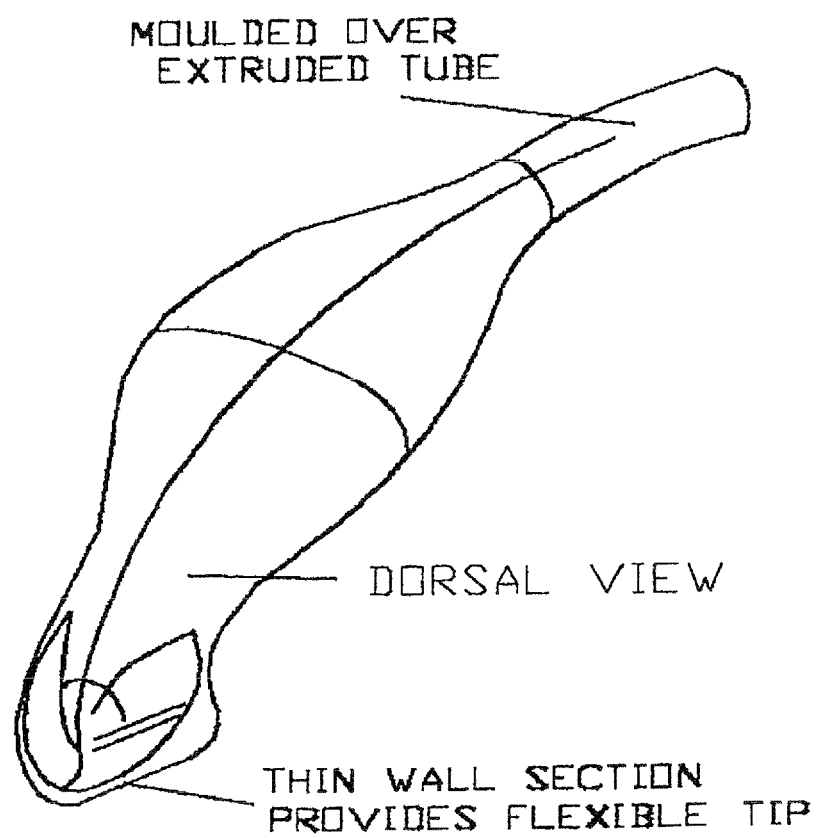
FIGS. 4 to 7 illustrate two further embodiments with exploded views showing each airway device in two halves with an airway tube sandwiched between the halves.

In one preferred embodiment the cuff is non-inflatable and is formed from any suitable soft plastics material. By way of a preferred softness (hardness) range, on the Shore A scale of Hardness, a hardness of less than 40 for the face of the cuff that contacts the laryngeal inlet is optimum. By way of a preferred range, a value on the same scale of between 0 to 20 is preferred, with a particularly preferred range of 4 to 12. The softness of the cuff can be further adapted by forming cavities or channels within the body of the cuff itself (shown in FIGS. 4 and 5).

In a further preferred embodiment the cuff may be pre-filled with a fluid such as air, or other non-toxic gas, or a non-toxic liquid. In this context the term fluid has a broad meaning and includes any suitable gas, liquid, vapour or combination thereof and will be determined and designed by an expert in this field of anatomy/anaesthesia in conjunction with the materials specialist. The cuff will be constructed of such a material which will not allow nitrous oxide (anaesthetic gas) to diffuse through the material to any significant amount so that the extra luminal pressure is kept constant. It follows therefore that the cuff should be substantially impermeable to the fluid with which is filled and to anaesthetic gases.

Alternatively, the cuff can be formed from a soft, foamed material or can be foam filled. In either case this provides a soft deformable but shaped surface around the face of the cuff to engage over the anatomy of the larynx inlet region. Such a foam filled device will minimise any potential damage to the structures in that region whilst still providing a substantially complete seal.

Directly adjacent to the laryngeal cuff/cup but positioned on the proximal side of the airway tube to the cuff itself is a buccal cavity stabiliser 20. In this example this stabiliser takes the form of an expanded region extending symmetrically on either side of the airway tube. This stabiliser is adapted to rest on the anterior aspect or front of the tongue and is configured to correspond with the anatomy of that part of the patient.

A wide variety of shapes, sizes, and positions for this stabiliser are possible. The one illustrated in FIG. 2 is curved in the plane of the cuff face such that the face visible in FIG. 2 is slightly concave, with the rear face being slightly convex. The face of the stabiliser may be roughened, scored or serrated to increase the friction with the tongue and thus stabilise it in use, to avoid or reduce forward or backwards movements when in use.

In this example the stabiliser is formed integrally with the cuff, such that one runs smoothly into the other. However, this is not essential and the stabiliser could be a separate unit on the airway tube. An essential feature of the stabiliser is that it is broader in cross-section than the diameter of the airway tube itself. That is to say it extends into a region either side of the airway tube and in the same generally plane as the laryngeal cuff. Preferred dimensions for the buccal cavity stabiliser will be discussed below.

Figure 11:
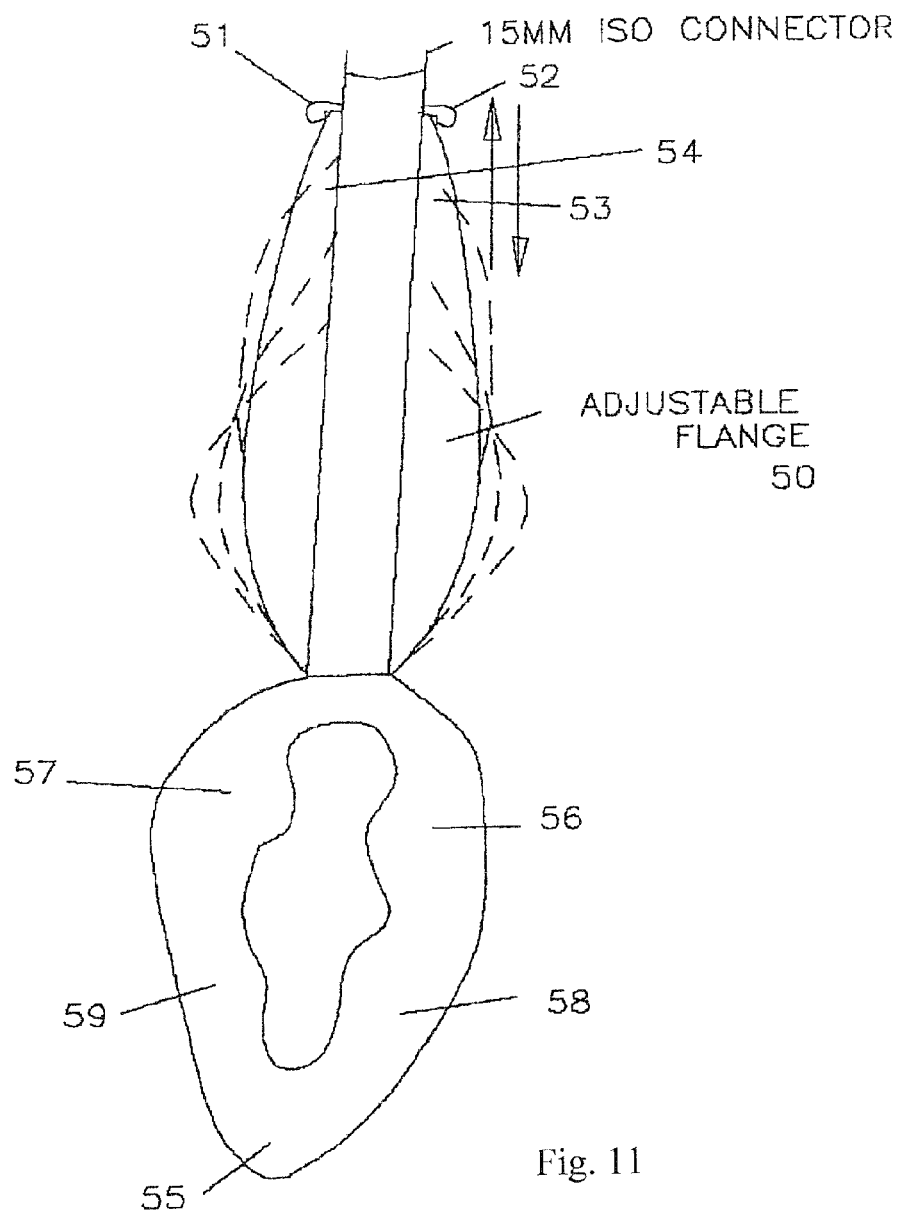
FIGS. 11, 12 and 13 show two frontal and one side or lateral view of a further embodiment according to the present invention in which the buccal cavity stabiliser is adjustable in size.
Figure 12:
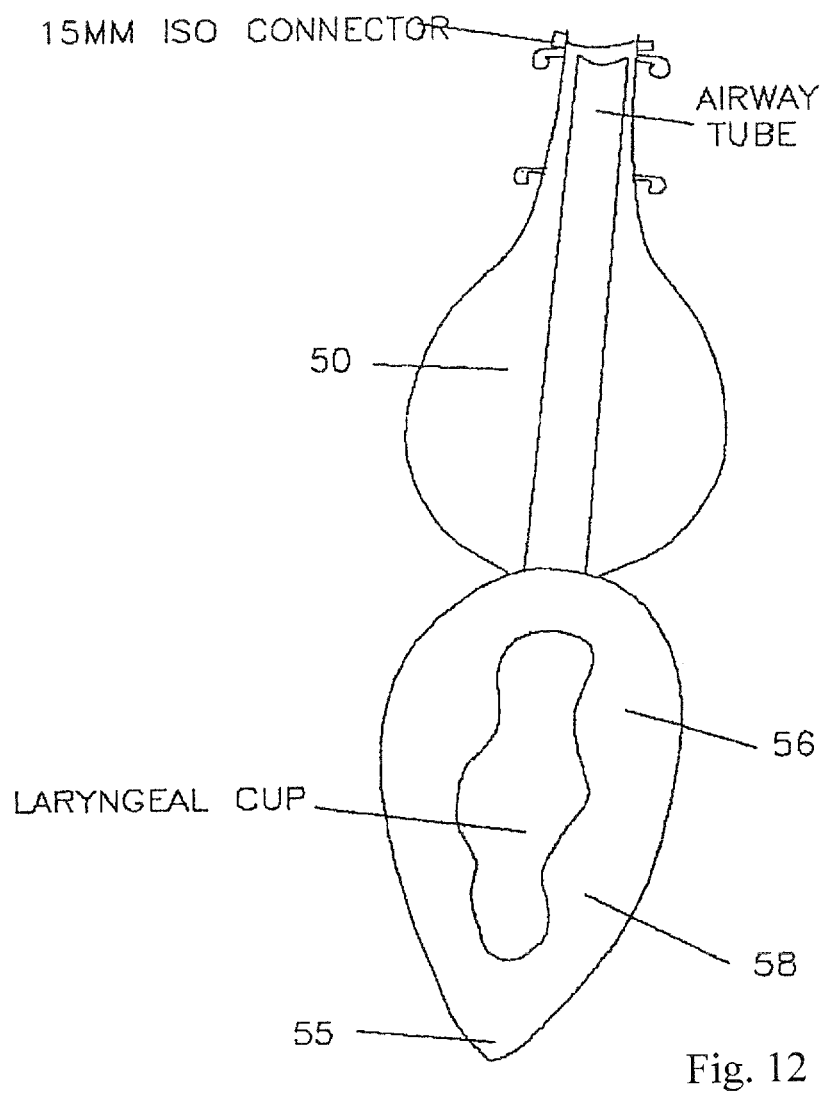
Figure 13:
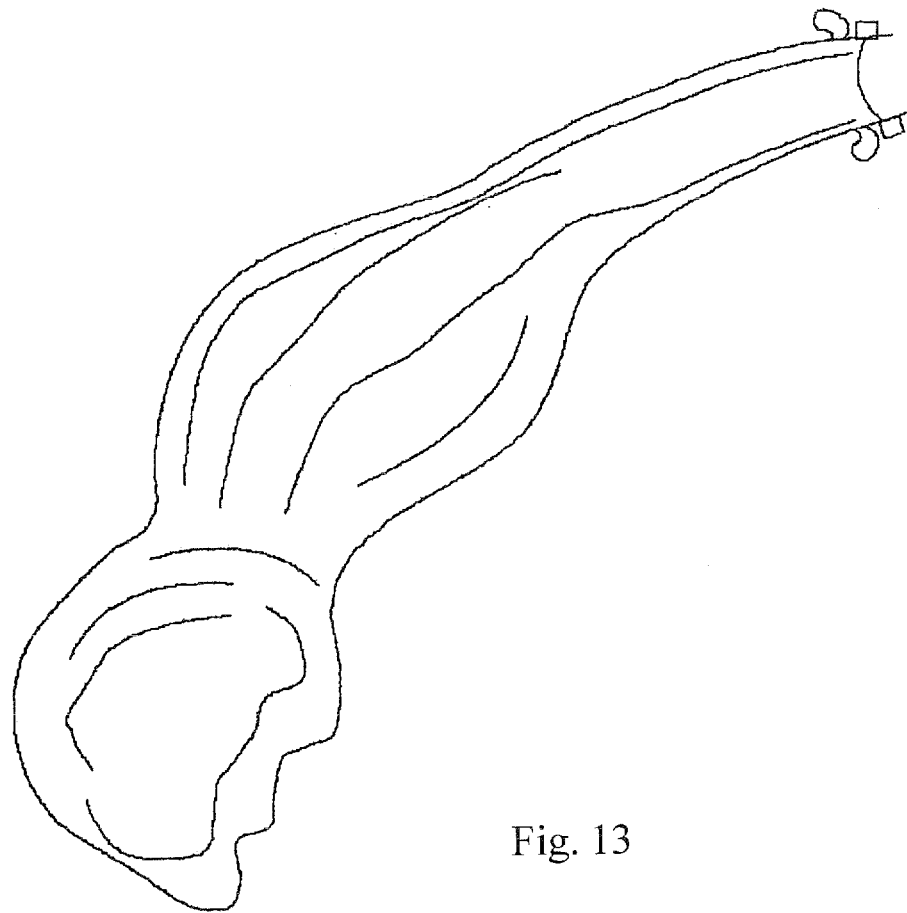
Figure 14:
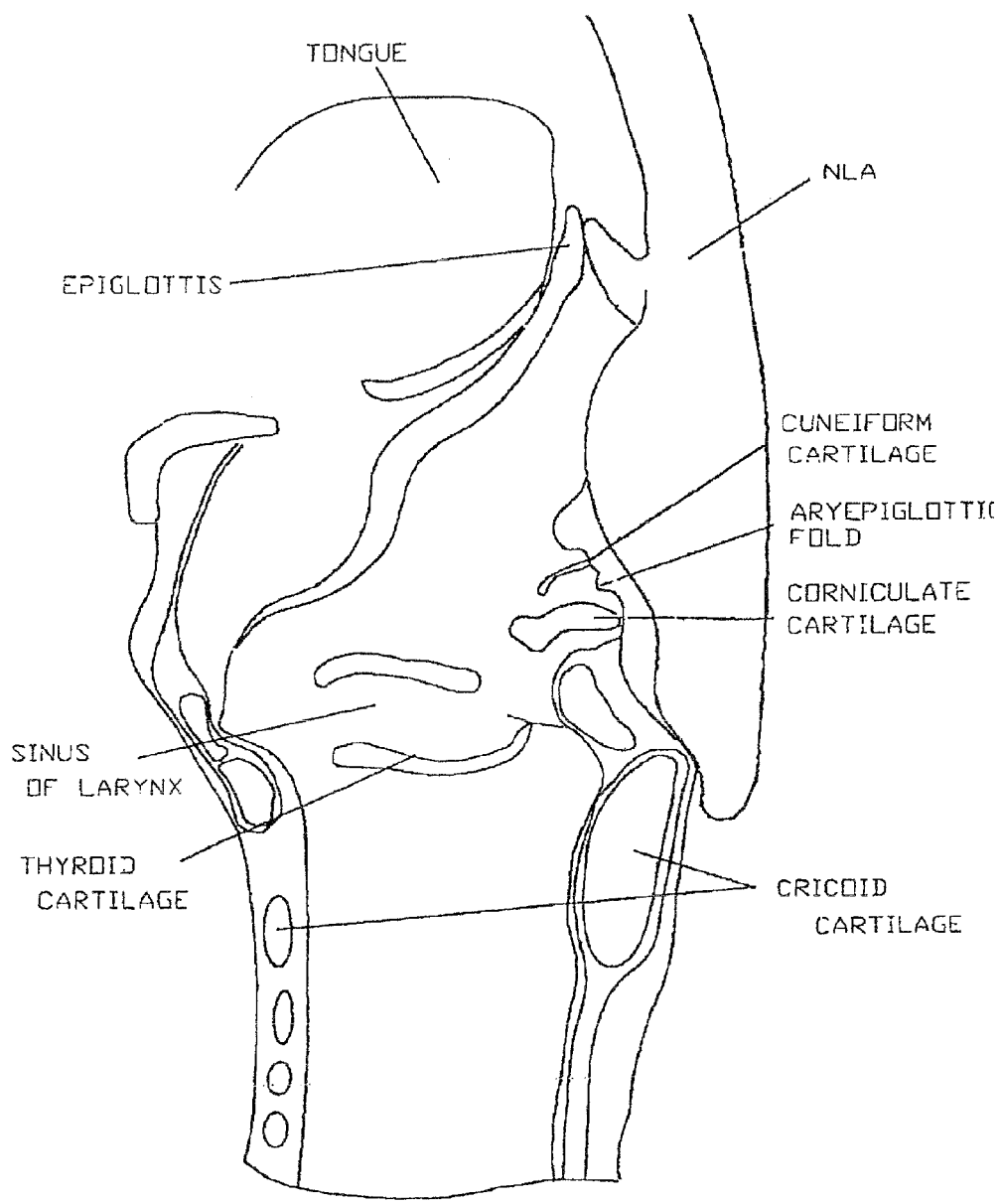
FIG. 14 shows diagrammatically an airway device according to the present invention engaged over a laryngeal inlet.

A further example of a different design of buccal cavity stabiliser is illustrated in FIG. 11, 12 and 13. In this example the stabiliser 50 is adjustable and has two side hooks 51, 52 at the lateral aspects, near the proximal end of the airway tube, which can be slid downwards and upwards to increase or decrease the size of the flanges for adequate stability, and for the ease of insertion and removal of the NLA. The hooks engage into ratchet strips 53, 54, formed in opposing sides of the airway tube. The stabiliser is formed from a resiliently deformable, flexible material such that as the hooks are forced from their position as shown in FIG. 11 to a position closer to the cuff at the distal end of the tube, as illustrated in FIG. 12, the spread of the stabiliser on either side of the airway tube increases the more the hooks are moved towards the cuff, and therefore the broader the stabiliser. Thus the stabiliser extends from the proximal end of the airway tube, just below the connector to the proximal end of laryngeal cuff. The stabiliser is substantially symmetrical in shape and can be slid down to give an expanded shape across the buccal cavity. FIG. 13 shows an oblique lateral view of this embodiment.

This is just one of the many methods which could be used to form a stabiliser. A stabiliser could be formed from any, preferably soft, extension around the airway tube wall that can lie on the anterior aspect of the tongue. Any suitably shaped laterally extending flange whose body lies mainly along the longitudinal axis of the airway tube would serve this purpose. The flange need not be solid, so a tubular, mesh or other perforated structure would be perfectly acceptable. The stabiliser preferably has a concave face or region when viewed from the direction shown in FIG. 11, ie from a direction normal to the face of the cuff, that conforms substantially to the anterior region of the tongue of the patient.

It is also possible to form such a "flange" by broadening the profile of the airway tube at the appropriate region, just above the cuff. That is to say, the buccal cavity stabiliser may be an integral part of the airway tube, rather than being a separate component formed on or around the airway tube itself. Thus, a suitable increase in the general profile of the airway tube, whether formed by the tube itself or by forming additional material around the tube, can act as a stabiliser.

The general profile of the buccal cavity stabiliser and the way that it merges smoothly into the cuff region can be seen in more detail from FIGS. 16 and 17A and B, which will be described in more detail below. However, it will be appreciated that both weight and plastics material would be saved if the internal diameter or profile of the airway tube increased and decreased correspondingly with the width of the buccal cavity stabiliser. The term "internal profile" is used because, as the airway tube broadens it becomes non-circular and instead assumes a substantially elliptical shape. It will therefore be appreciated that in this embodiment the cross-sectional area of the airway tube increases as the width of the buccal cavity stabiliser increase to its widest point and then decreases again. By maximising the width of the airway tube this has the potential to increase laminar flow within the device.

A further feature of the airway device shown in FIG. 11 are the two sets of protrusions or bulges 56, 57 and 58, 59 on the face of the cuff. The larger of the two sets 56, 57 are adapted to around the aryepiglottic folds and in the pyriform fossae. The smaller of the two 58, 59 are adapted to fit around the Thyroid and Cricoid cartilages. In addition, the tip of the cuff 55 is a soft, tapered lip but is preferably not inflated.

Figure 3:
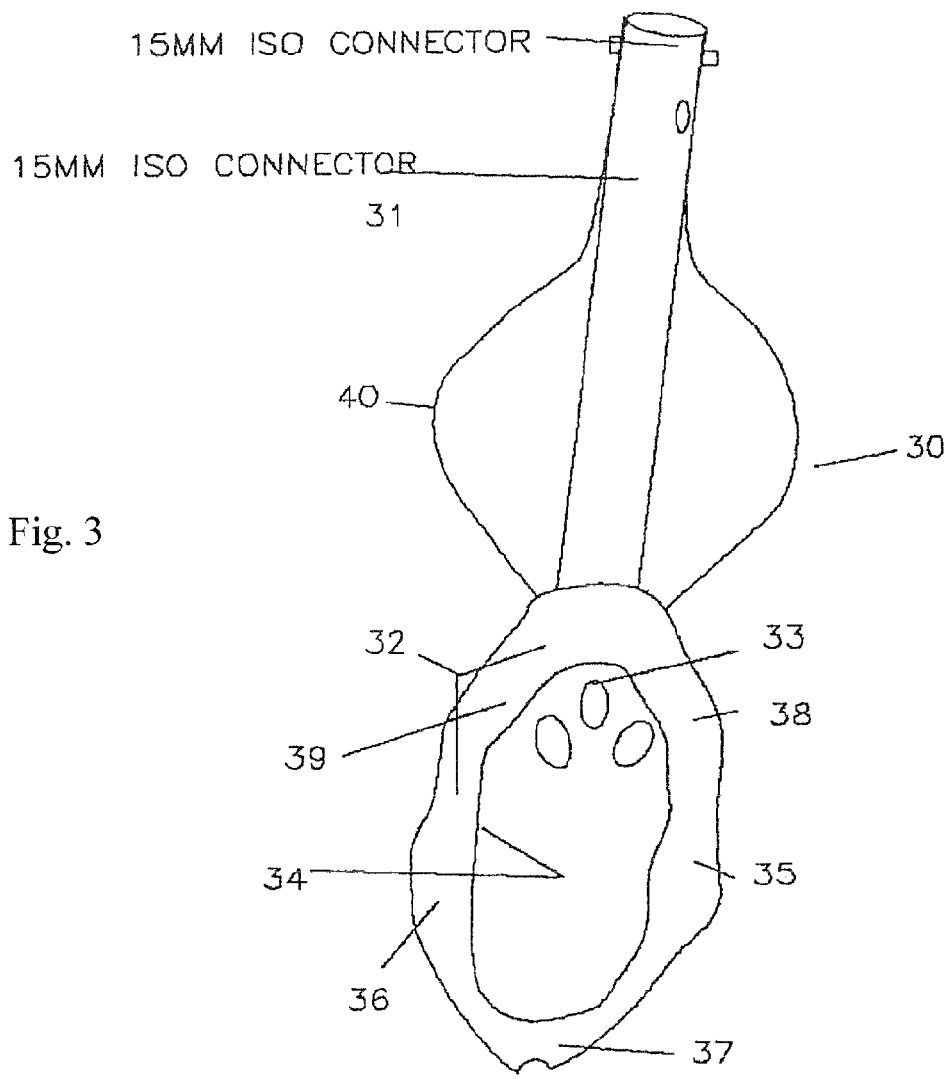

A further example is illustrated in FIG. 3. This illustrates an airway device 30 having a cuff 34 and a buccal cavity stabiliser 40. In this case there are two outbulgings or protrusions on either side of the cuff 35, 36, 38 and 39. An upper set, 38, 39 consisting of one protrusion on each side, is designed to lie around the aryepiglottic folds and in the pyriform fossae. The lower set 35, 36 are designed to lie around the thyroid and cricoid cartilages. The relative sizes of these bulges will be determined by the appropriate specialist. It is probable that the bulges 38 and 39, designed to fit around the aryepiglottic folds and in the pyriform fossae will be slightly larger than the two lower bulges. The distal/lower end of the cuff is soft but firm, and preferably not pre-inflated or pre-filled for the ease of the device's insertion, and adapted to lie in between the larynx and oesophagus. Further variations are shown in FIGS. 4 to 7, which show the flexibility possible within this general design concept. FIGS. 6 and 7 illustrate the possibility of including an additional moulding 60 on the proximal end of the unit.

Figure 5:
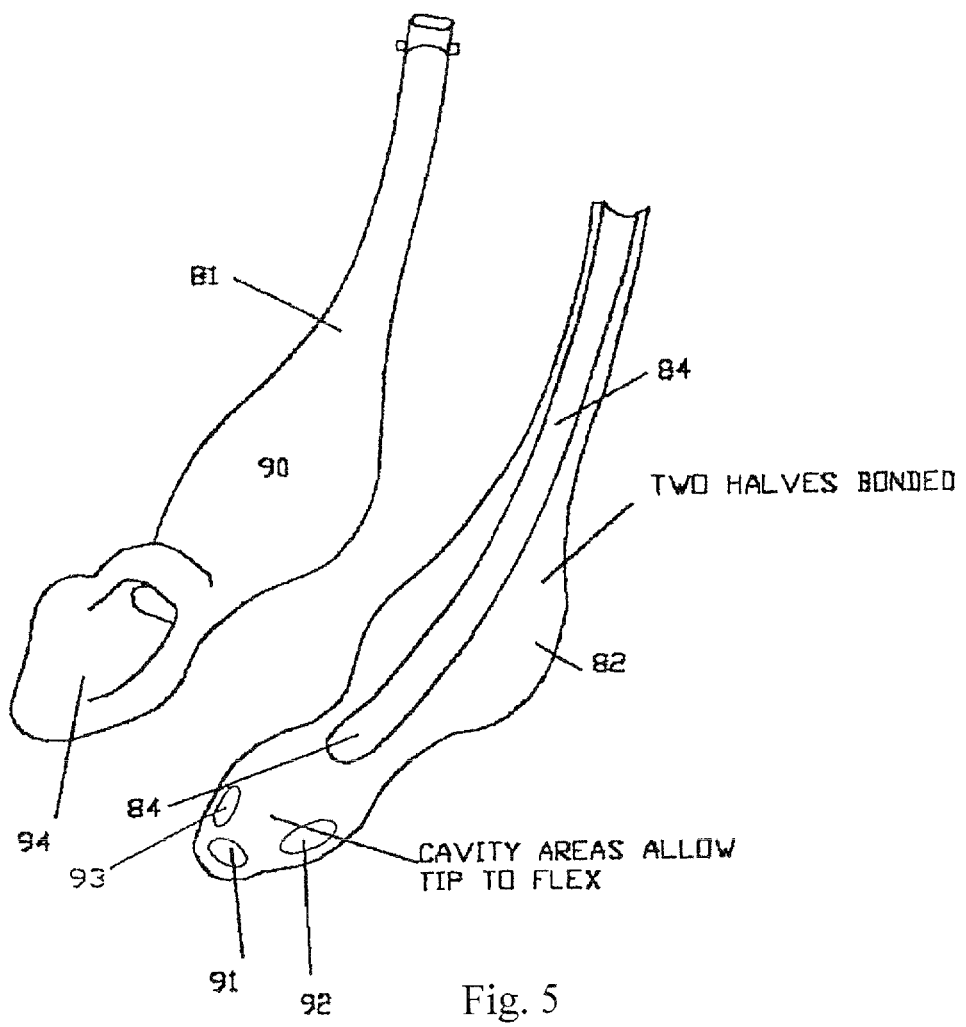
Figures 6, 7:
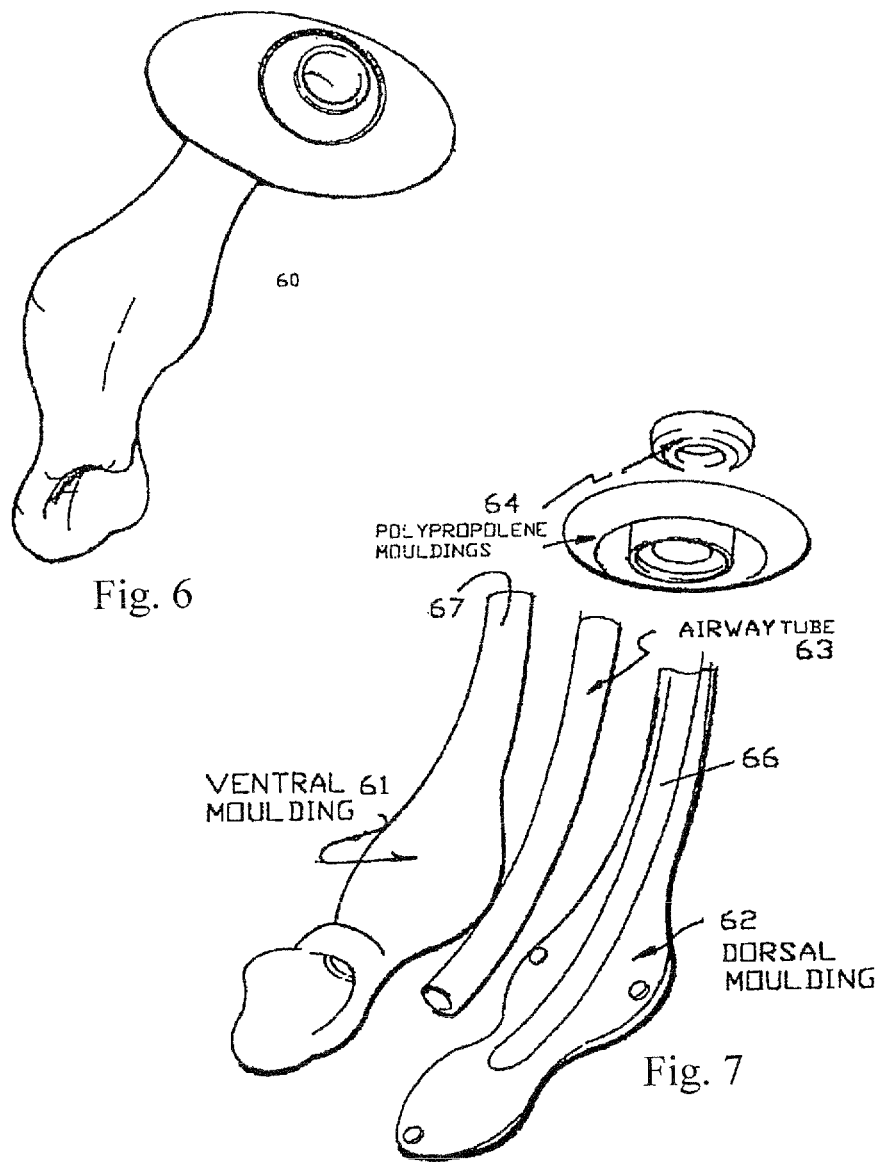

FIG. 5 illustrates one possible method of manufacture of a device according to the present invention. The device is manufactured from appropriate material as described previously in two halves 81 and 82. The two halves are bonded together around an airway tube 83 (not shown for clarity). The airway tube fits into a specially designed channel 84. In this example the buccal cavity stabiliser 90 is moulded integrally with the cuff 94. The tip of the device contains a series or plurality of cavities 91, 92 and 93. In this context plurality means one or more. These cavities increase the flexibility of the tip, which aids the insertion, and positioning of the device in use. These cavities also affect the softness and pliability of the tip, their presence making the tip softer than if it was formed from solid plastics material. Generally, the softer the material, the less potential there is to damage the tissue of the patient. The generally concave nature of the device is also apparent from FIGS. 4 and 5.

A further feature in these embodiments which is apparent from these figures is that the distal tip of the device tapers to a gentle point. This tapered end is intended to lie or wedge between the larynx and the oesophageal inlet.

An understanding of one method of constructing an airway device according to the present invention can be appreciated from FIGS. 4 to 7 inclusive. Basically, the device in FIG. 7 is formed in two parts 61 and 62 plus a moulding 64 which includes a 15 mm or other connector to connect the device to an anaesthetic breathing system. 61 is a ventral or front moulding, being that portion which comes into contact with the patient's laryngeal inlet and tongue. 62 is a dorsal or back moulding, being that side which faces away from the ventral portion. These definitions of ventral and dorsal are used throughout this specification.

Optionally the device may also include a separate airway tube 63 that nests within channels 66, 67 formed within the internal body of mouldings 62 and 61 respectively. However, in a particularly preferred embodiment this separate tube 63 is omitted. In this example the tube 63 and mouldings 62 and 61 are made of silicone rubber and the mouldings 64 and 68 from polypropylene. The larger of the two polypropylene mouldings 68 is designed to prevent the device passing into the patient's mouth beyond a certain point.

The airway tube may be of any appropriate diameter, or cross-section if the tube is not circular. Typically a 9 mm tube would be used in an adult version of the airway device.

The mouldings 61 and 62 are bonded, glued, welded (including but not limited to heat welding and laser welding) or otherwise fixed together during assembly. It follows from this simple, elegant and cost-effective form of manufacture that the two components 61 and 62 can be formed from materials with different hardnesses. Thus the front portion of 61 that contains the laryngeal cuff can be made out of a softer material than the back portion. Typical Shore hardnesses on the A scale for the front portion 61 are between 0 to 20, more preferably 0 to 15 and more preferably 4 to 12.

The rear portion 62 has typical Shore hardness values of 20 to 60 and more preferably 30 to 40.

Figure 8:
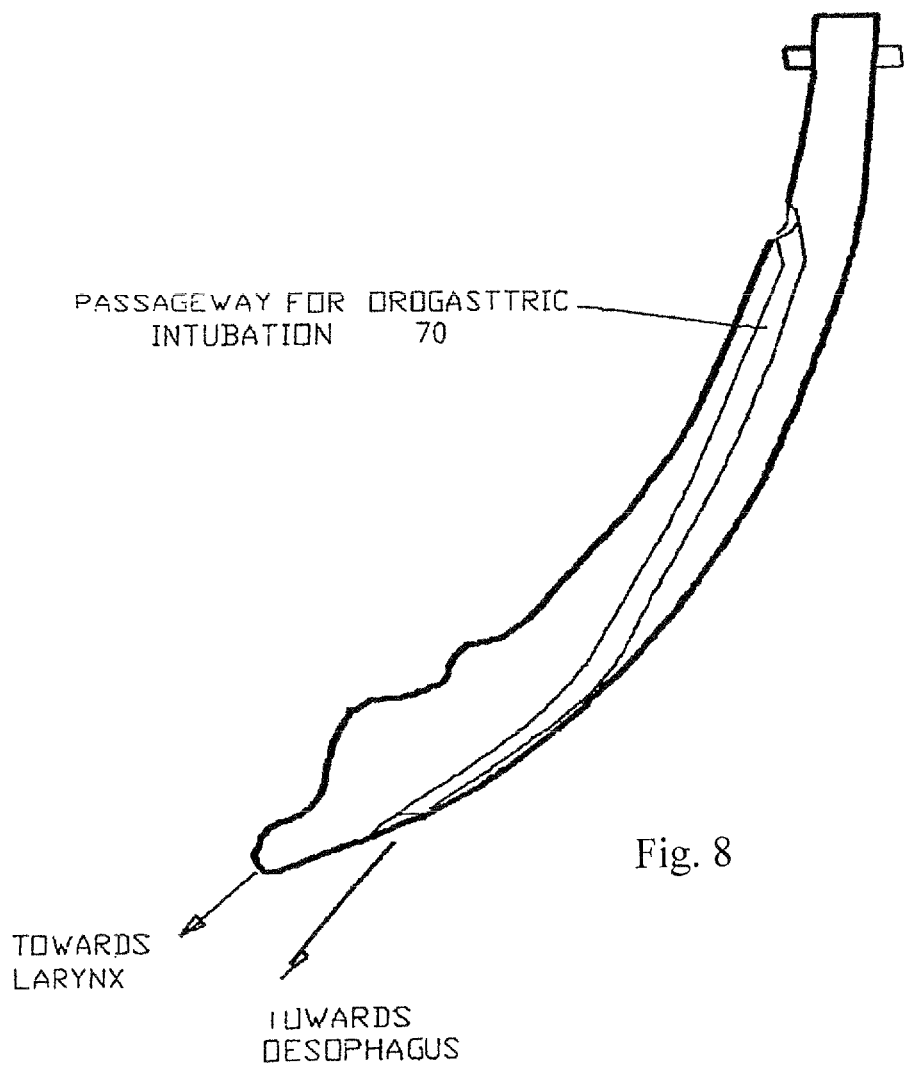
FIG. 8 shows an optional feature of a second passageway or tunnel starting at the lateral aspect of proximal end of NLA and curving towards the distal end to give its NLA tube/distal opening a posterior aspect of the NLA tube through the mask to allow passage of an orogastric tube.

It is possible to incorporate an additional passageway 70 or passageways within the body of the unit and alongside the airway tube. An example of this is illustrated in FIG. 8. This passageway allows other tube(s) or wire(s) to be passed down the oesophagus during use without the need to move or disturb the device. For example, orogastric intubation now becomes possible.

Figure 9:
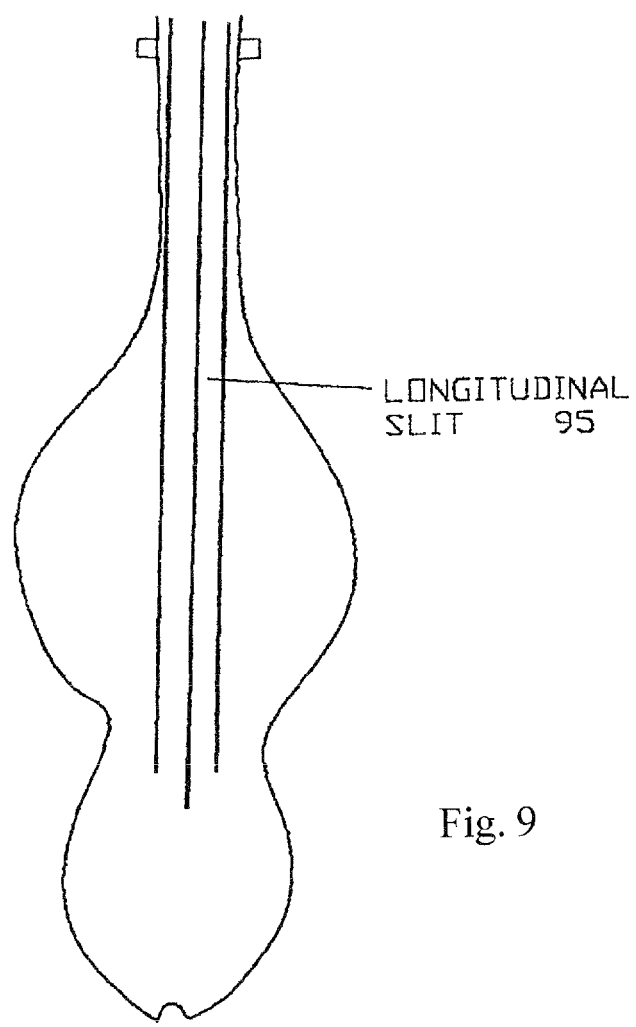
FIG. 9 shows a longitudinal slit running substantially the length of the mask to accommodate an endotracheal tube used in anticipated or unexpectedly difficult intubations; with or without the use of a bougie, Cook's airway or fibre-optic scope.

In another variant, shown in FIG. 9, the airway incorporates a longitudinal slit extending substantially the whole length of the passageway. This allows other tubes or wires (bougies, stylets etc) to be inserted or withdrawn during use without the need to disturb the mask, during planned or unexpected difficult intubations. Furthermore, this slit arrangement means that the airway device can be released from the tube or wire and removed from the patient leaving the tube or wire in place undisturbed.

FIG. 10 shows a further embodiment of the present invention and also shows the generally curvilinear shape of the device along its longitudinal axis. This shape is designed to correspond with the mouth/throat opening in an anaesthetised patient. The longitudinal axis is the axis line shown as the straight dotted line in FIG. 10.4 and runs from the proximal and of the airway tube to the distal tip of the cuff.

The general shape of one preferred embodiment of the buccal cavity stabiliser is shown in FIG. 10.3. The stabiliser, generally shown as 100, is formed around an airway tube 101. However, as described above, a separate tube is not necessary and a tubular passageway can be formed from channel(s) formed into the body of the stabiliser. The stabiliser portion extends 102, 103 on both sides of the tube 101 in a generally elliptical cross-section. It will be appreciated from FIG. 10.1 and 10.5 and FIGS. 17 and 18 that the width of the buccal cavity stabiliser is non-uniform and varies along its length. This is in contrast to the airway tubes of similar prior art devices, which are generally uniform in cross-section. The width in this context is the edge-to-edge dimension in a direction normal to the longitudinal axis of the device and in a plane substantially parallel to the plane of the open face of the cuff. The stabiliser is narrowest at the proximal end of the device, then increases in width to a widest point, and then decreases in width again until it merges into the proximal side of the laryngeal cuff. The widest point of the stabiliser is therefore between the proximal end of the airway tube and the proximal end of the laryngeal mask. Generally it is advantageous if the widest part is nearer to the laryngeal mask end than it is to the proximal end, as shown in FIGS. 17A and B. This locates the widest part nearest to the anterior region of the patient's tongue in use.

Importantly the height H of the stabiliser does not vary in a similar way. Rather the height remains substantially the same along the longitudinal axis of the stabiliser. This is quite different from conventional airway tubes.

It will be evident from the foregoing that the width of the ellipse W at its widest point is greater than the height H at the same point. By way of example, for an adult airway device according to the present invention the width W of the stabiliser, at its widest point, would be in the range 3.5 cm to 4.5 cm and the height H would be in the range 1.25 cm to 1.75 cm. A preferred ratio of W:H is 2.7±10%.

An important feature of the shape of this stabiliser is the profile of the upper 104 and lower 105 outer surfaces. These are both convex and gently curved in their broadest regions. This not only makes for ease of use but, more importantly, the lower surface 105 which comes into contact with the tongue in use, is profiled to follow the shape of the back of the patient's tongue and is soft enough to deform to conform to it.

Figure 16A:
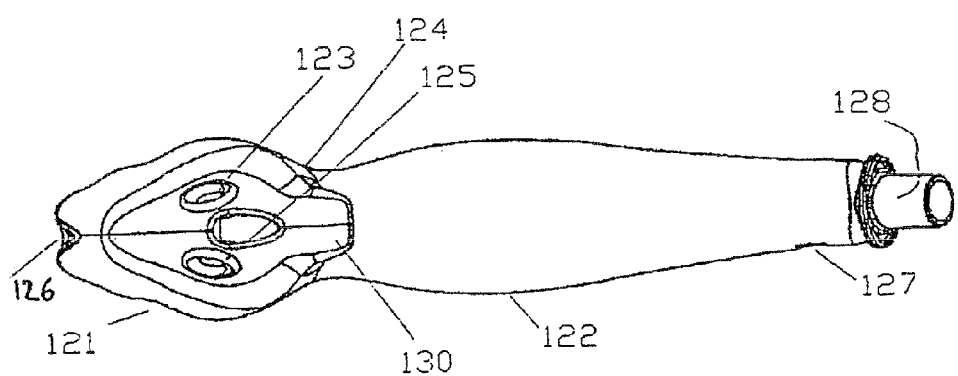
Figure 16B:
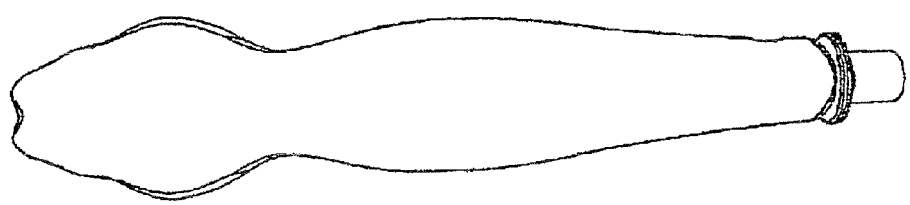
Figure 17A:
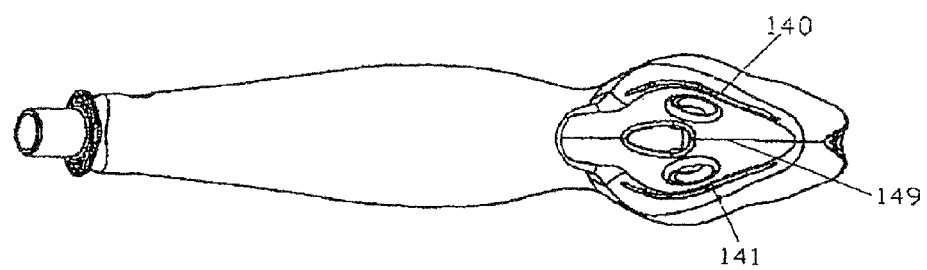
FIGS. 17A, B, C and D show front and side elevations of particularly preferred embodiments incorporating thin, flexible flanges around part of the circumference of the laryngeal cuff.
Figure 17B:
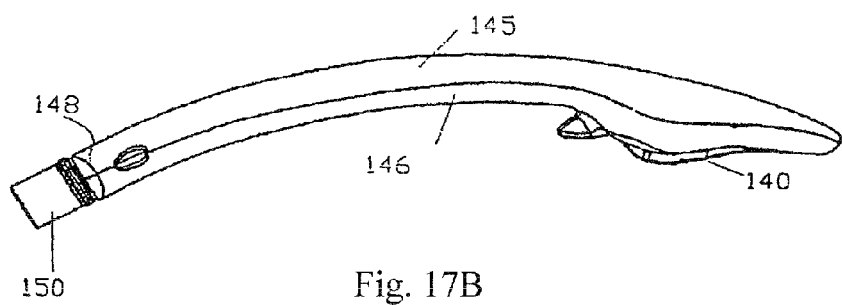

A further embodiment is illustrated in FIG. 16. In this embodiment the airway tubing 111 is only partly contained within the body of the airway device 110. The distal end of the tube passes into and completely through the body of the device to form an opening within the cuff 113. In this embodiment a different profile of stabiliser is illustrated. In this case the lower surface 115, which contacts the tongue in use, is gently concave in shape, with the upper surface being generally convex.

Once bonded together, the device becomes what is, in effect, a unitary construction. That is to say, the components become as one. This simplifies sterilization, if the devise is reusable, and increases reliability.

However, unitary construction is not essential. For example, it may be possible to form the buccal cavity stabiliser as a separate component (not shown) that is threaded over, around or on to the airway tube if required. This design would give the anaesthetist the option of using the device with or without a stabiliser as desired. It would be necessary to incorporate some form of securing means to secure the stabiliser to either the cuff or the tube. Means of fixing or securing plastic components are well know, such as snap-fit connectors.

This option increases the design options for the stabiliser. A form of leaf spring, secured at one or both ends to the airway tube could be employed. Alternatively an inflatable structure could be used. It will be recalled that inflatable cuffs have been used in this context. However, this type of technology has never been used before to incorporate a buccal cavity stabiliser into a device of this type.

Figure 17C:
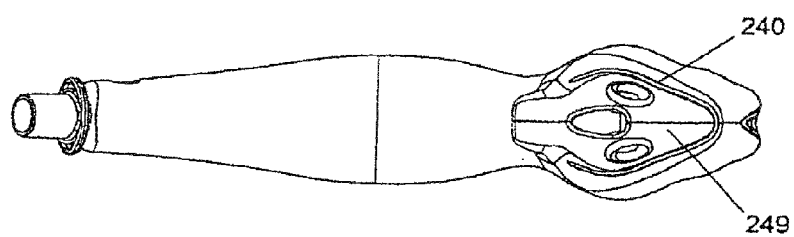
Figure 17D:
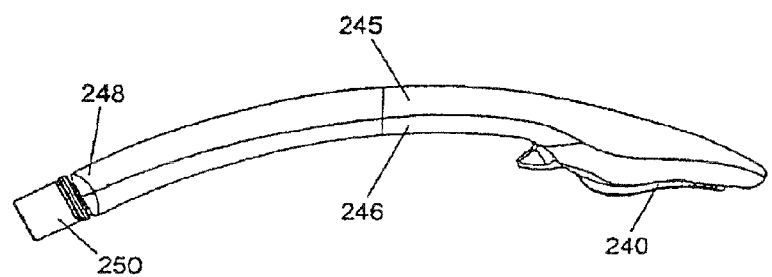
Figure 18:
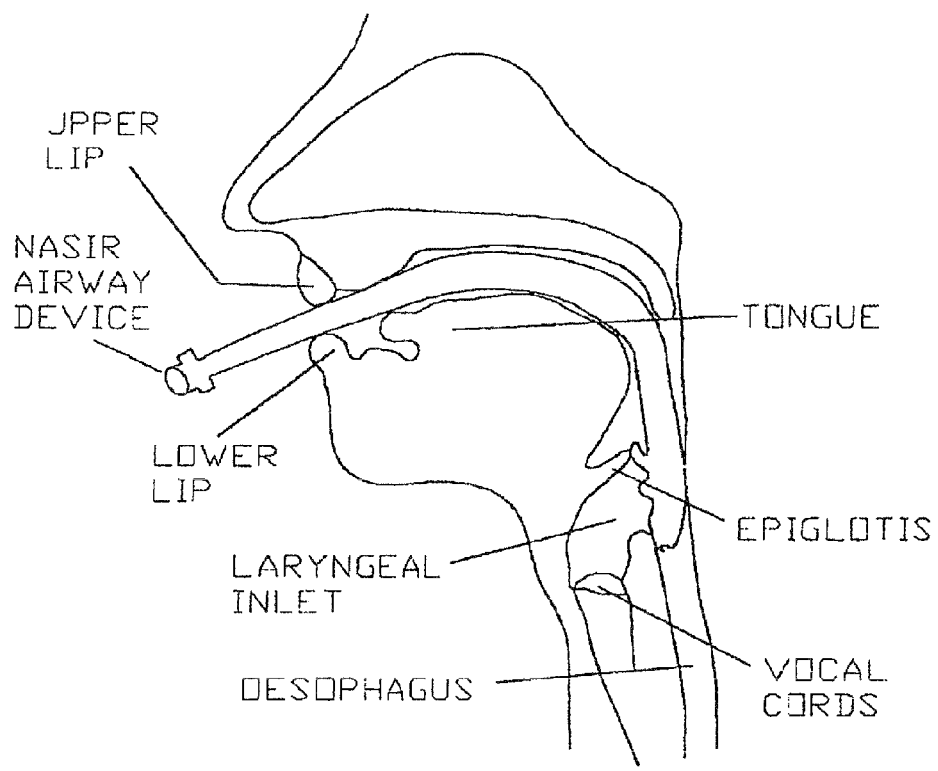
Figure 19:
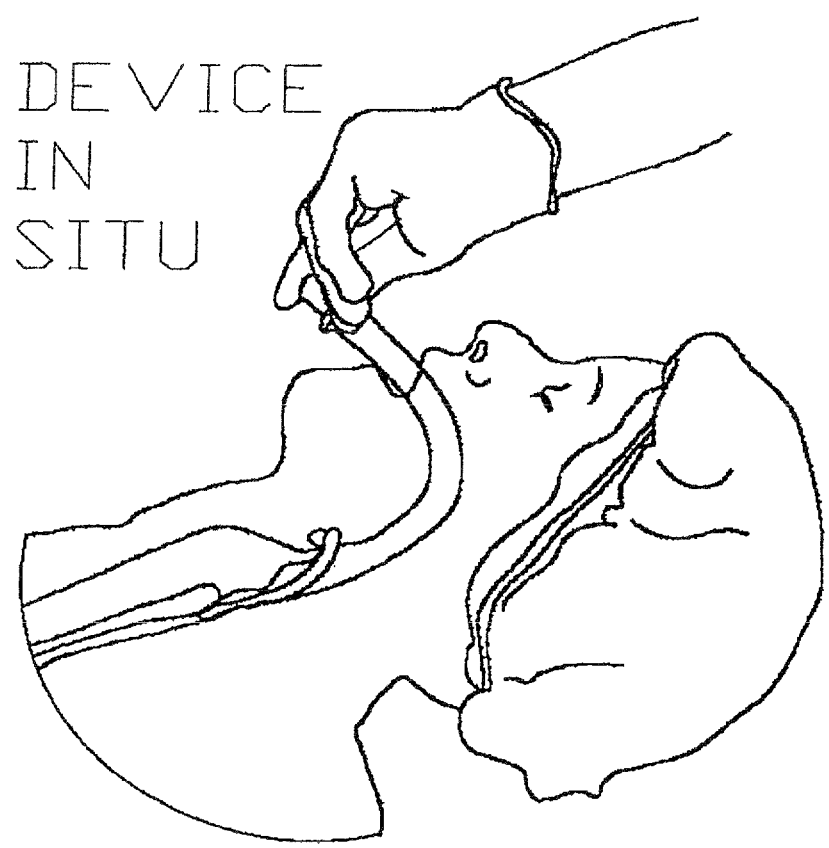
Figures 22A, 22B, 22C:
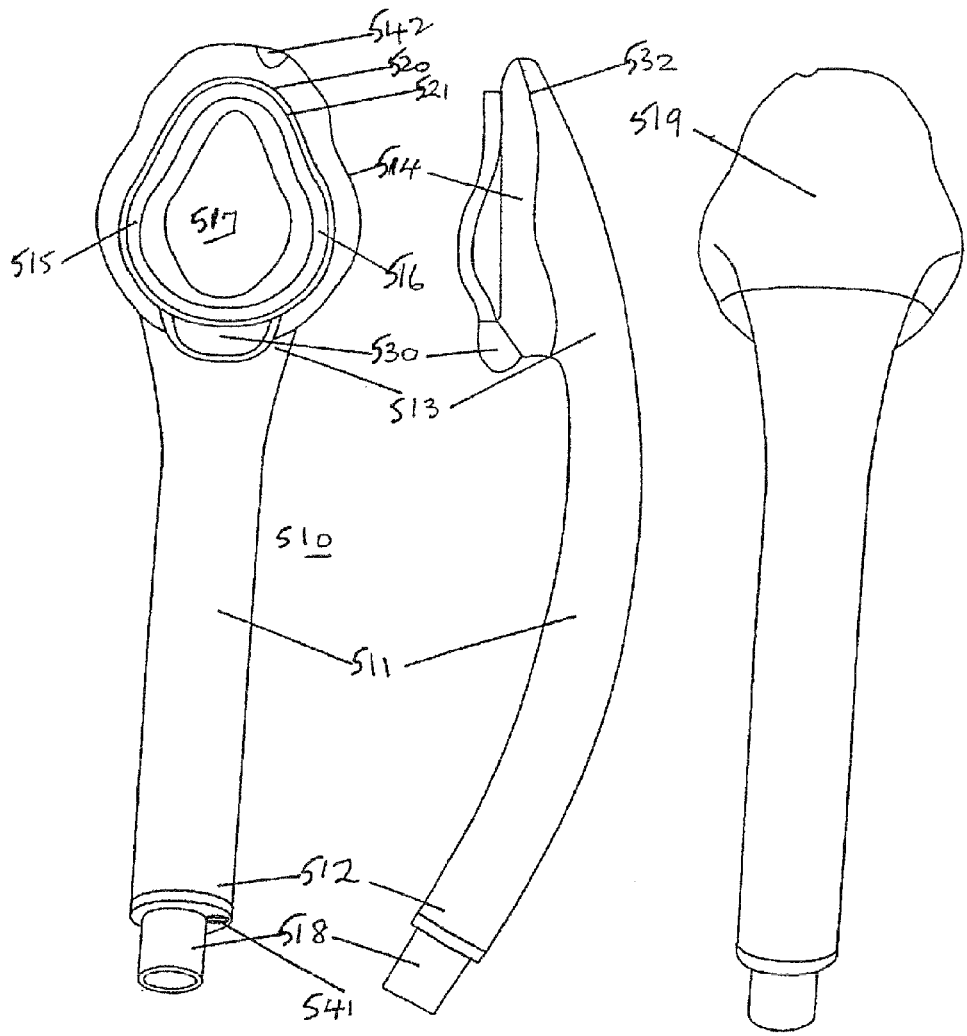
FIGS. 22A, B and C illustrate front, side and rear elevational views of an airway device according to a first embodiment of the present invention having a substantially circular profile airway tube.

Two further embodiments are illustrated in FIGS. 17 and 18. These illustrate the streamlined, unitary construction of these embodiments of the invention, with the cuff region 121 merging smoothly into the buccal cavity stabiliser region 122. There are certain other key features shown in these Figures. For example, where the airway tube enters the laryngeal cuff, it does so through three separate apertures 123, 124 and 125. This greatly decreases the chance of the airway tube being blocked. The shape of the distal end of the stabiliser joining the proximal end of the cuff/cup is designed in such a way that when the device is in situ, it fits anatomically correctly in and around the valecullae.

The distal tip of the cuff 126 has been truncated and in fact is now concave in shape. This results in less compressive pressures being exerted over the thyroid and cricoid cartilages, blood vessels and nerves supplying the laryngeal framework than is the case with prior art devices. This socalled concave tip can take a variety of different shapes and forms. The tip may be "squared off" such that the end of the tip is substantially planar. Or there may be a pronounced indentation in the tip, as shown in FIG. 17A. At the base of that indentation is an aperture forming the end of a gastric tube passageway described below. In summary, this truncation is intended to encompass any tip which results in less compressive pressure being exerted than by prior art devices.

A second, gastric tube passageway, separate to the airway tube is provided which runs from an opening 127 in the proximal end of the device near the connector 128 to an opening in the distal tip of the cuff 129, more clearly shown in FIG. 17E. The gastric tube allows for any gastric aspirate to be detected in the event of passive regurgitation during use. It also provides a route for the insertion of small-bore gastric tubes (eg Freka Tubes).

A further novel feature of this device is the lip or flange 130 located at the proximal end of the cuff region. This lip is sized and shaped so as to be anatomically positioned against the epiglottis, to ensure a proper seal and to hold the epiglottis back from folding towards the laryngeal inlet avoiding obstruction to airflow. This tip takes the form of a leaf like structure extending out of the laryngeal cuff and directed back towards the proximal end of the airway tube. Its relative size and shape can be seen from FIG. 17. The optimum size and shape will be determined by experimentation. The applicant is not aware of any prior art masks which contain this feature.

FIG. 18 also illustrates certain novel features of construction and of the laryngeal cuff. Turning first to the cuff, in this embodiment thin, flexible featherlike flanges 140 and 141 have been introduced on opposing sides of the cuff. These are preferably formed as an integral part of the moulding of the cuff and, because of the very soft nature of the material used to form the cuff, these flanges are particularly soft and pliable. Their purpose is to make allowance for any individual patient variation in the laryngeal inlet shape and to contribute to forming an efficient and effective seal between the cuff and the laryngeal structures. By this design, and by designing the cuff to be a close anatomical fit, the obtainable seal pressure from experimental trials is well in excess of 30 cm $H_2O$.

The feather-like flanges 140 and 141 are shown in FIG. 18 as discontinuous structures but these can in fact be connected to each other towards the distal end of the cuff (FIGS. 18C and D). In this arrangement flanges 140 and 141 become a single U-shaped flange extending around the majority of the laryngeal cuff perimeter.

Also shown in FIG. 18 is a two-part form of construction. The two parts are an upper, curved portion 145, whose outer surface is generally convex and a lower curved portion 146 whose outer surface is generally concave and which includes the face of the laryngeal cuff which contacts the patient's laryngeal inlet in use. Formed within these two portions is an airway tube channel that extends from the proximal end 147 to the distal or cuff end 149, and the second passageway described above.

The upper and lower parts are then bonded together around connector 150 by use of a suitable adhesive or welding technique as selected by the materials specialist.

The upper portion 145 and the lower portion can advantageously be formed from materials having different Shore hardnesses. Thus, the upper portion can be formed of a material having a Shore hardness on the A scale in the range of 30 to 40, whereas the lower portion can be formed from a softer material with a hardness in the range 4 to 12 on the same scale.

If required, the cuff region can be formed from a different material and of a different hardness, from other parts of the device. This arrangement is shown in FIG. 17C where the device is formed in three parts 135, 136 and 137 rather than two.

However, the elegant and simple design of this airway device does allow for an even simpler method of manufacture. It has been discovered that the device can be moulded as a one-piece unitary construction in one mould. By constructing the mould appropriately, and by careful consideration of how the mould parts separate, one-piece manufacture is possible. The moulding may be produced using a process commonly known as 2 shot injection moulding, in which the materials are injected separately to form the relevant parts of the component. Alternatively, the component could be formed from material of the same hardness throughout using a single injection process, and if desirable overlain, in all or part of the ventral or dorsal section, with a material of differing Shore hardness. The technology for forming such overlay or laminates is known to those skilled in art.

Turning now to the design of the laryngeal cuff, in the foregoing examples the cuff region has been pre-formed from a soft material, or pre-filled during manufacture with a fluid. In the latter case the lining of the cuff should be made from a material that does not absorb anaesthetic gases such as Nitrous Oxide, such that the pressure inside the cuff does not rise during use.

In any alternative embodiment the cuff may be formed from a material which is adapted to absorb a liquid, such as water, mucous or blood or similar liquid material and in doing so to swell in size so as to confirm to the anatomical muco-cartilagenous framework of the patient's laryngeal inlet. Such materials will be selected by the materials specialist but include CRM (cotton rayon mixes) as used in TAMPAX® tampons, or compressed Gel Foam 5.

In a further, alternative embodiment, the cuff could take the form of a conventional, inflatable cuff. Whilst this is not ideal, because of the inherent disadvantages of inflatable cuffs, the incorporation of a buccal cavity stabiliser of the type described above, made from soft materials as described above, into an inflatable laryngeal mask airway device represents a significant improvement over and above prior art inflatable masks. The technology to form an inflatable cuff is well known and need not be described here.

In summary, the aims and objectives of the present invention are to provide an anatomically oriented, versatile, reliable, simple and cost effective device intended to be used in spontaneously breathing anaestetized patients or patients recovering from anaesthetic, in certain group of intensive care patients during their weaning process and during resuscitation, to provide a secure, clear and hands-free airway for the delivery of oxygen and/or anaesthetic gases.

Main aims and objectives are as follows:—

To provide a simplified design which has all the advantages of existing airway devices and has an anatomically oriented working mechanics in order to establish a clear airway in spontaneously breathing anaesthetized patients, patients in post-anaesthetic recovery phase or certain group of intensive care patients undergoing weaning off their ventilatory support.

Avoids almost all the disadvantages and complications of currently used airway devices in anaesthetic practice.

No need of laryngoscopy, intubation, or extubation and minimally invasive to pharyngo-larynx.

User friendly, would require minimal training for anaesthetists, other doctors, nurses, paramedics and rest of the health care staff likely to use the device.

A useful tool in the management of an unexpected or/and anticipated difficult endotracheal intubation. Useful either with an endotracheal tube through the airway or with planned Fibre-optic intubation or bronchoscopy.

Self-retaining with hardly any need to tape or tie.

In summary the device has a Connector, expanded glossopharyngeal flanges and a pre-formed, pre-inflated or pre-filled anatomically designed laryngeal cup or cuff suited to the exact contour and shape of the laryngeal inlet. However, this should not be seen to prevent this invention being used with a conventional, inflatable cuff.

Connector:

15 mm ISO standard connector suitable to be connected with any of the gas delivery systems used in anaesthetic, during post-anaesthetic recovery, in intensive care and resuscitation practice.

Expanded Glosso-Pharyngeal/Buccal Flanges:

All the existing airways intubation devices have a varying degree of propensity to lateralize towards right or left angle of the mouth, rotation through 180 degrees about it's longitudinal axis and the movements of the airway inwards or outwards, which can lead to the displacement or misplacement of the distal end of the airway thus becoming ineffective for the purpose of it's use. A combination of the expanded flanges of the device, and constructing the device from a material of a Shore hardness less than 60 on the A scale, enables the buccal cavity stabiliser to act as an anchor for the airway device in the midline position by stretching over the anterior surface of the tongue across the buccal cavity and supported laterally by inner surface are aimed for better anchorage of the airway over the tongue. Thus, not only stabilizing the airway device positioned centrally but also stopping it to lateralize and/or rotate. Distally the expanded flange is incorporated into the flattened and angular part of the laryngeal cup with the postero-inferior surface of the tubular part of the device distally, in order to provide additional anchorage into the narrow hypopharynx.

Anatomically Oriented Laryngeal Cup:

A soft rubber or pre-formed, pre-inflated/pre-filled with a suitable liquid or soft material cup aimed not to exert an extra-luminal pressure of more than 22 mmHg onto the mucosa of Laryngeal inlet and adjacent structures thus avoiding any compression or shearing forces onto the pharyngo-laryngeal mucosa ensuring a continued, uninterrupted blood flow through the capillaries of the surrounding tissues, thus ensuring an uninterrupted blood supply of the structures in contact with it. Anatomically oriented laryngeal cup sealingly surrounds the laryngeal inlet without distorting the structures with which it is in contact.

Laterally the out-bulgings of the cup or cuff are designed to fit around the pits of the Aryepiglottic folds and infero-laterally piriform fossae. The tapered lower end is for the ease of its passage through the oro-pharynx which will provide a seal over and beyond the interarytenoid fold in the midline and cuneiform and corniculate cartilages laterally. An upper midline slit will help the cup's passage over the epiglottis without damaging or folding and twisting the epiglottis into the cavity or distal opening of the device into the cup. Above the slit, is the flatter part of the soft cup which is designed for the optimal placement in the hypo-pharynx in between the epiglottis and the base of the tongue thus separating the surrounding structures away from the glottis. Although the cup provides a near natural and anatomical seal over the glottic opening but still prevention from the aspiration of regurgitated gastric contents cannot be guaranteed. Such risk could be minimized by using a modified device with an oesophageal component in high risk patients.

Sizes:

Sizes from 0-7 are envisaged.

| 1 to 2 | for neonates and infants | (weight 3-20 kgs) |
| --- | --- | --- |
| 3 | for children | (weight 21-50 kgs) |
| 4 to 5 | for adolescents | (weight 51-90 kgs) |
| 6 to 7 | for adults | (weight more than 90 kgs) |

Re-usable or disposable devices may preferably be made of materials as described above such as latex-free SEBS or medically graded silicone rubber. A re-usable (sterilizable) device would be capable of at least 40 uses. The simplicity of the design also offers increased ease of sterilization for the purpose of its reuse. Disposable devices would be a preferred choice of production which will be not only more economical but also devoid of any risk of cross infection as may be the case in re-usable devices.

As a result of the above design features a device according to the present invention, is likely to cost much less than any comparable device.

NLA with Oseophageal Component

Addition of an oesophageal component is intended to be used in patients with a suspicion of gastric statis under anaesthetics, in Intensive Care Units and for the patients with highly irritable airways who pose a well recognized and wide spread problem of weaning from ventilatory support. Such patients almost certainly end up with Tracheostomy in order to bypass their upper irritable airway, to facilitate weaning. Patients with chronic obstructive/restrictive airway disease, asthmatics and heavy smokers are the ones who are more likely to pose the weaning problem.

Intubating NLA

Morbidity or mortality in patients with an anticipated or/and unexpected difficult intubation is a well-recognized aspect of anaesthetic practice and a challenging nightmare for any anaesthetist when faced with that situation. A modified version of the NLA with a preformed longitudinal slit to the anterior of NLA will help facilitate intubation through the NLA with an endotracheal tube with the help of bougie, Cook's airway or a fibre-optic scope.

Others

Some modifications to the shape, design and working mechanics of each of the Component of the NLA are envisaged, whether needed for NLA's improved Performance or aesthetic look.

The whole of the airway device could be manufactured as a single unit- or each component of it manufactured separately if it is deemed necessary for the sake of its improved function or cost effectiveness or due to any other issue of practicality.

It will be appreciated that, as used herein, the anatomical terms "anterior" and "posterior," with respect to the human body, refer to locations nearer to the front of and to the back of the body, respectively, relative to other locations. In the context of this description, the term "proximal" means the end of the device, or portion thereof, closest to the connection to the anaesthetic breathing system. The term "distal" means the end of the device, or portion thereof, furthest from the anaesthetic breathing system or alternatively, the cuff end of the device. The term "lateral" refers to a location to the right or left sides of the body, relative to other locations. "Bilateral" refers to locations both to the left and right of the body, relative to other locations. The anatomical term "medial" or "medially" refers to a location toward the centre or midline of the body, relative to locations both to the left and right of the body.

The airway devices described above have a soft laryngeal cuff adapted to fit anatomically over and form a seal with the laryngeal structure of a patient. An essential feature of these embodiments of this device is a so-called buccal cavity stabiliser, located around the airway tube, and which is designed to nest with the anterior aspect of the patient's tongue.

The laryngeal cuffs on these devices are generally non-inflatable, but rather are formed from a soft, deformable material that can adapt to the individual detail of the patient's laryngeal inlet to form a satisfactory seal. It was precisely because of the very soft, deformable nature of these cuffs that it was considered necessary to incorporate some form of stabiliser to locate the cuff during insertion and to maintain a good gas-tight contact with the laryngeal inlet at all times during use. It should be borne in mind that "use" can involve the patient in many hours on the operating table under anaesthesia and can also involve use in accident and emergency situations involving hostile conditions that are non-ideal for such treatments.

Referring to FIG. 23, this illustrates front, side and rear elevations of an airway device according to a first embodiment of a further aspect of the present invention, generally shown as 510. This comprises an airway tube 511, which at its proximal end 512 terminates in a 15 mm or other connector 518 suitable for connection to an anaesthetic breathing system of conventional type. Formed around the distal end 513 of the airway tube is a laryngeal cuff or cup 514 adapted in its shape and contours to correspond with the laryngeal inlet region of a patient. In this context the terms cuff and cup have an equivalent meaning. They refer to the element of the device at the distal end of the airway tube that is adapted to cover and form a seal with the laryngeal inlet of the patient in use. The anatomy of the laryngeal inlet region of a human is well known to the expert. It is illustrated in some detail in FIG. 1 and the key thereto.

The cuff 514 has an opening 517 in a face or front region of the cuff and the back or dorsal part of the cuff is closed. The opening 517 in the face of the cuff connects directly to the airway tube 511 such that gas is free to flow from the connector 518 through the airway tube and out of the open face of the cuff.

The particular cuff shown in FIG. 23 incorporates in the cuff face pronounced and discernable bulges or protuberances 515, 516 designed to form a good substantially gas-tight seal with the piriform fossae and aryepiglottic folds. It will be appreciated that the outbulgings in the cuff at 515 and 516 are positioned antero-laterally to the laryngeal framework and give an anatomical seal by fitting into the piriform fossae and aryepiglottic folds and space postero-inferior to the thyroid and cricoid cartilages, and the posterior cartilages (corniculate and cuneiform). Thus, in side elevation, the face of the cuff is not a flat planar surface but includes regions that protrude above the general plane of the cuff face. Additionally, there may optionally be regions which lie below the general plane of the cuff face. These shapings and the general size, shape and configuration of the surface of the cuff face around opening 517 are an important feature of the invention.

Thin, flexible, featherlike flanges 520 and 521 extend substantially around the circumference of the opening 517 in the face region of the cuff. These flanges are preferably formed as an integral part of the moulding of the cuff and, because of the very soft nature of the material used to form the cuff, these flanges are particularly soft and pliable. Their purpose is to make allowance for any individual patient variation in the laryngeal inlet shape and to contribute to forming an efficient and effective seal between the cuff and the laryngeal structures. By this design, and by designing the cuff to be a close anatomical fit, the obtainable seal pressure from experimental trials is well within the range of 12-40 cm $H_2O$, which is sufficient for ventilation.

These flanges need not completely encircle the opening 517 as shown in FIG. 1 but it is preferred that they completely surround the opening circumference, and in doing so they follow the general contours of the front face of the cuff. Flanges 520 and 521 are spaced apart slightly such that each flange is an integral item or unit. The flanges are spaced radially one from another around the opening such that one flange surrounds another. The term "radially" in this context has a broad meaning and refers to the spacing of each flange from an imaginary axis extending out of the opening in a plane substantially perpendicular to the general plane of the cuff face.

In this embodiment two feather flanges are shown. However, there may be no flanges, one flange or two or more than two flanges. In other words there may be none or a plurality of flanges, "plurality" having the meaning one or more in the context of this disclosure.

A further feature of the cuff is the epiglottic rest 530 located at the proximal end of the cuff region. This epiglottic rest is sized and shaped so as to be anatomically positioned against the epiglottis, to ensure a proper seal and to hold the epiglottis back from downfolding towards the laryngeal inlet avoiding obstruction to airflow. This epiglottic rest takes the form of a leaflike structure extending out of the laryngeal cuff and directed back towards the proximal end of the airway tube. Its relative size and shape can be seen from 530A in FIG. 31. The optimum size and shape for this epiglottic rest will be determined by experimentation.

Turning now to the airway tube, this is shown generally as 511 in FIG. 23. This tube, which is in the form of a hollow cylinder of substantially uniform cross-section open at each end, extends from the connector end 512 into the body of cuff 514 to connect with cuff opening 517. The inside diameter of the airway tube will depend on the size of the device, generally larger in adult sizes versus paediatric sizes, and designed in general to accommodate the appropriately sized endotracheal tube for endoscope guided intubation where necessary. The internal diameter of the tube may be substantially uniform along its length, although the internal diameter may vary.

In terms of intubation the airway device also has significant benefits over inflatable laryngeal cuffs during retrograde intubation procedures. This is because inflatable cuffs can potentially be punctured and deflated, which could result in lack of seal and problems with ventilation.

The tube is formed from a bendable plastics material that will be described in more detail below. With the exception of the region at the distal end of the tube where it starts to join the cuff, the external profile of the tube is substantially uniform between the distal end of the tube where it starts to meet the cuff and the proximal end of the tube. The term "substantially uniform" means that there is no region of the tube which could act as a buccal cavity stabiliser ie an expanded region extending on either side of the airway tube. Put another way, there is no section of the tube that extends on either side of the tube and which is generally broader in profile than the airway tube itself. The internal diameter of the airway tube will preferably be substantially uniform and circular, whether the tube has a circular or oval exterior profile, and the distal opening of the airway tube into the cuff is a single opening to help reduce the resistance to flow through the device.

Figures 24A, 24B, 24C:
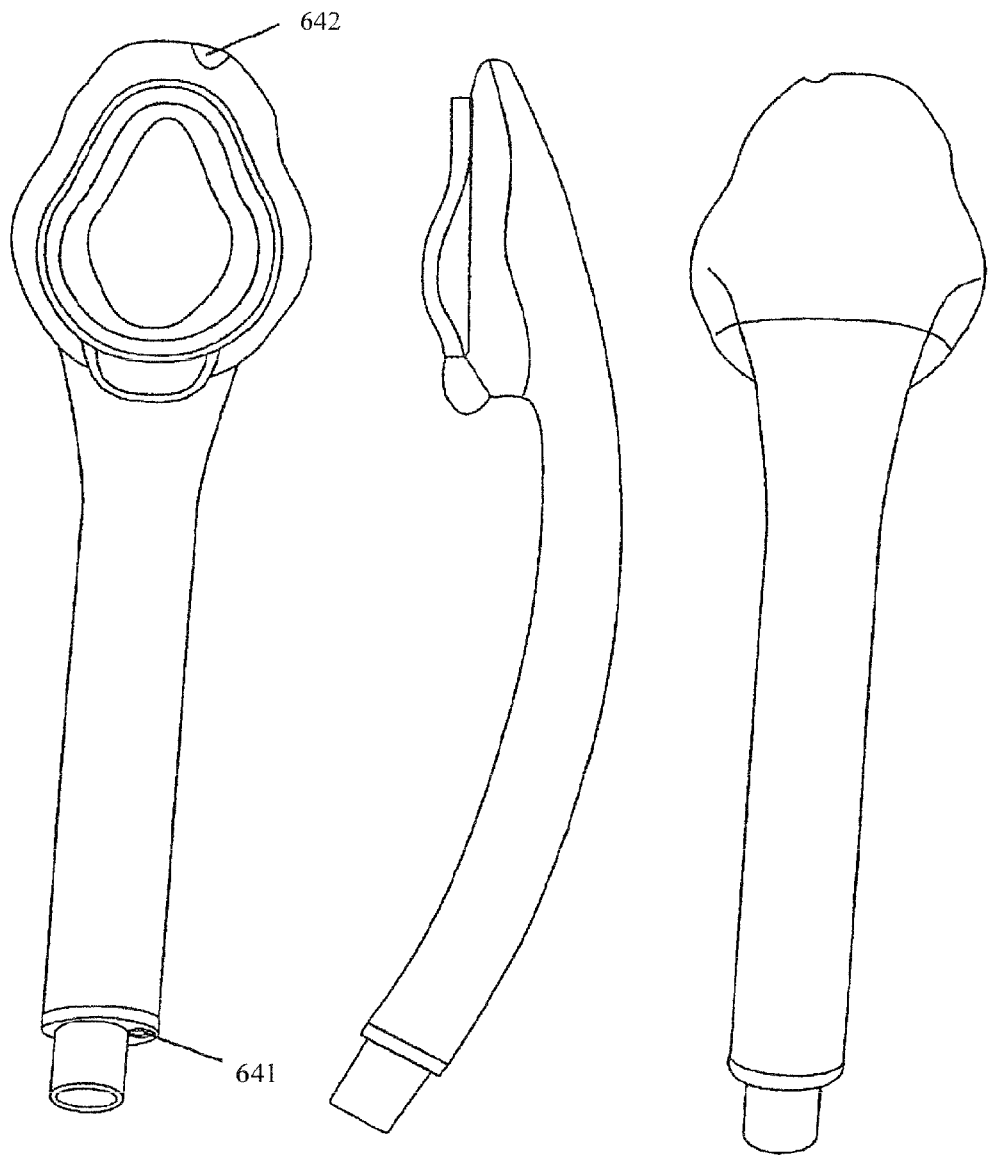
FIGS. 24 A, B and C show front, side and rear elevational views of an airway device according to a second embodiment of the present invention having a substantially elliptical profile airway tube.
Figure 26A:
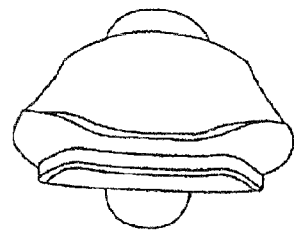
FIGS. 26A to D illustrate various perspective views of an embodiment without a gastric tube passageway.
Figure 26B:
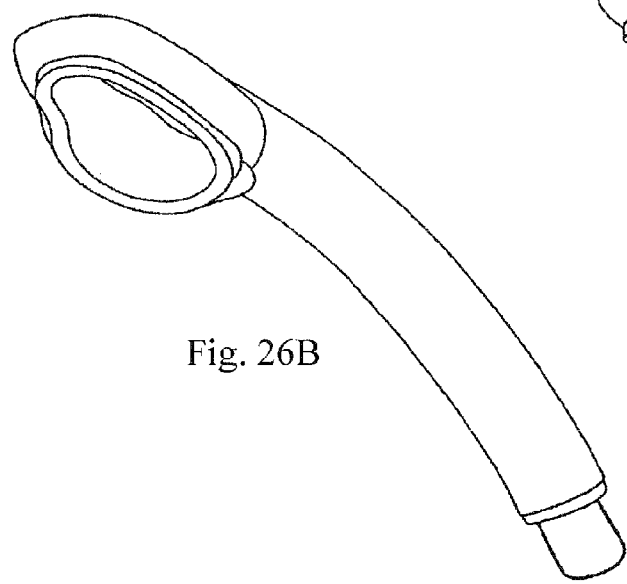
Figure 26C:
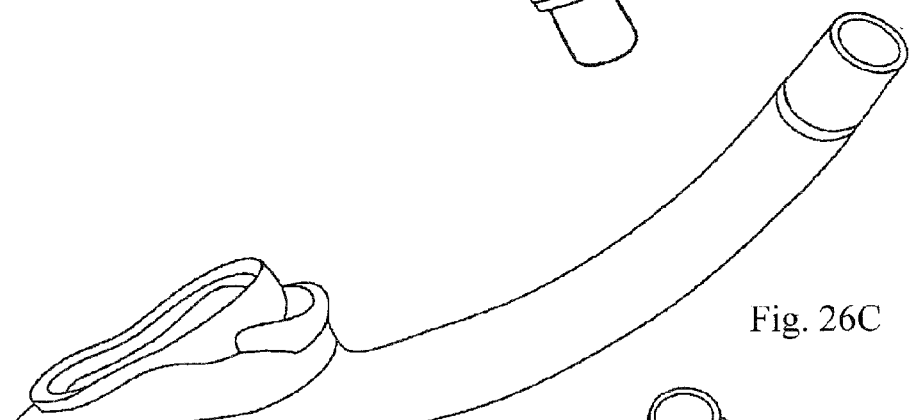
Figure 26D:
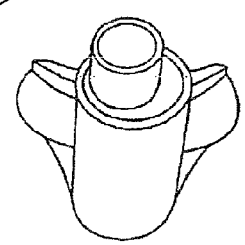
Figures 27A, 27B, 27C:
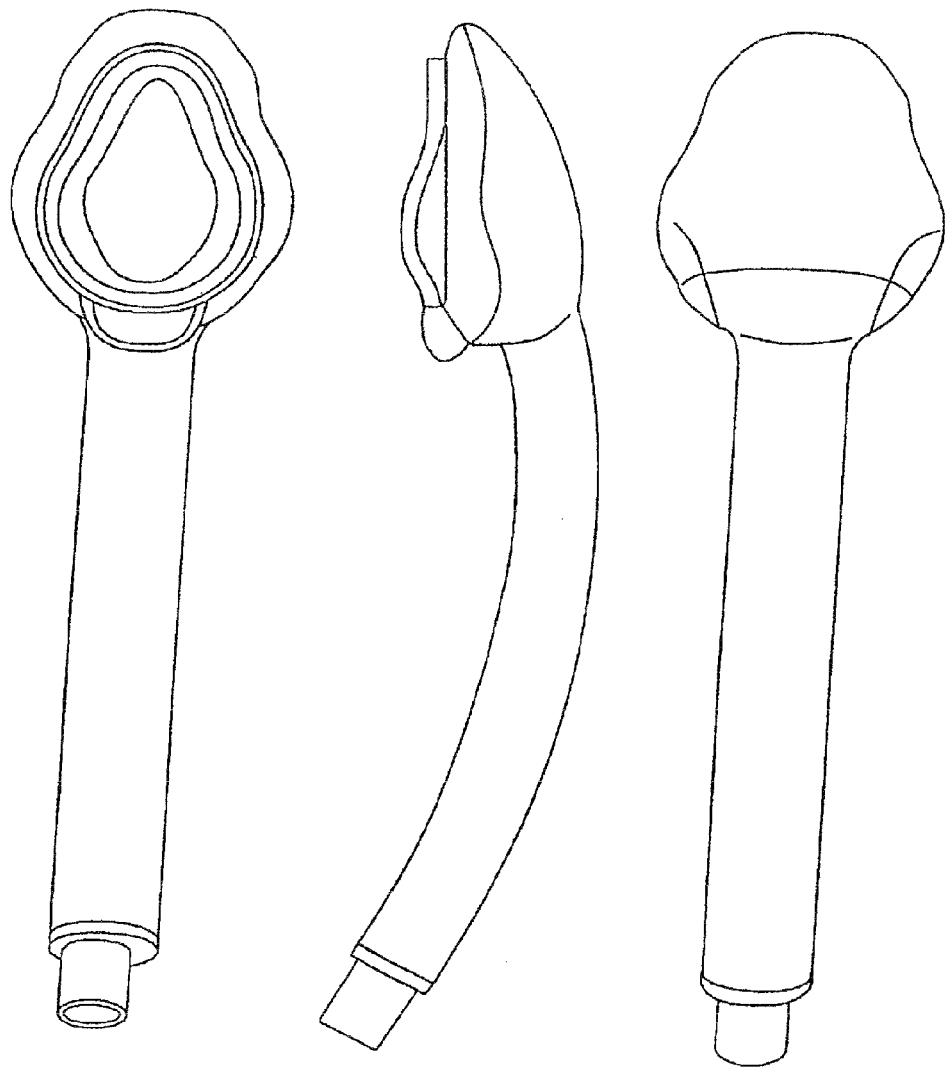
FIGS. 27A, B and C illustrate front, side and rear elevational views of an airway device according to a further embodiment of the present invention.

The airway tube can be formed with a variety of profiles. In the embodiment illustrated in FIGS. 23 and 24 the general external profile of the airway tube is substantially circular. This can be seen most clearly in FIG. 24D. In contrast, in the embodiment illustrated in FIGS. 25 and 26, the airway tube has a generally elliptical external profile, although the bore passing through the airway tube is substantially circular in cross-section. These are just two of many profiles that might be selected by the designer.

A connector 618 which fits into the end of the airway tube is shown in more detail in FIG. 32. There are two important features to note from this embodiment. Firstly, the length of the connector is significantly greater than a conventional connector and is such that it extends, in use, into the patient's mouth and beyond his/her teeth. In that way it acts as a bite protector and prevents the patient from inadvertently biting through the relatively soft material of the airway tube. The patient biting down onto the airway device and particularly or completely occluding airflow is a problem in certain procedures and with certain patients. Secondly, the connector fits into a recess formed within the airway tube by the moulding process. In this way, the internal surface of the airway tube 609 is substantially smooth and uniform. The internal diameter of the tube from the proximal opening in the connector to the distal end where it opens out into the cuff is substantially uniform. There is therefore no significant step change in internal diameter at the inner end of the connector, which leads to improved airflow and lower resistance to flow. This arrangement is shown particularly in FIG. 32C being a section along line E-E in FIG. 32B.

In addition to the airway tube, the embodiments shown in FIGS. 23 to 26 inclusive include a second passageway 540 that extends from an opening 542 in the distal end of the device to an opening 541 in the proximal end of the device. This second, gastric tube passageway, is designed to allow an operator to pass a gastric tube down into the stomach of a patient without interrupting anaesthesia, during EMS or during pre-hospital airway management. This second passageway also allows for detection of any gastric aspirate in the event of passive regurgitation during use. This second passageway must be large enough to allow a small bore gastric tube to pass easily through the device. Typically a gastric tube passageway would be between 6 to 14 French gauge diameter.

The gastric tube passageway 540 and 640 shown in FIGS. 23 and 25 is shown housed substantially within the body of the airway device. However, it is also possible that this passageway could run externally of the new main body, for example laterally or along the dorsal face of the device body.

Figures 33, 34, 35:
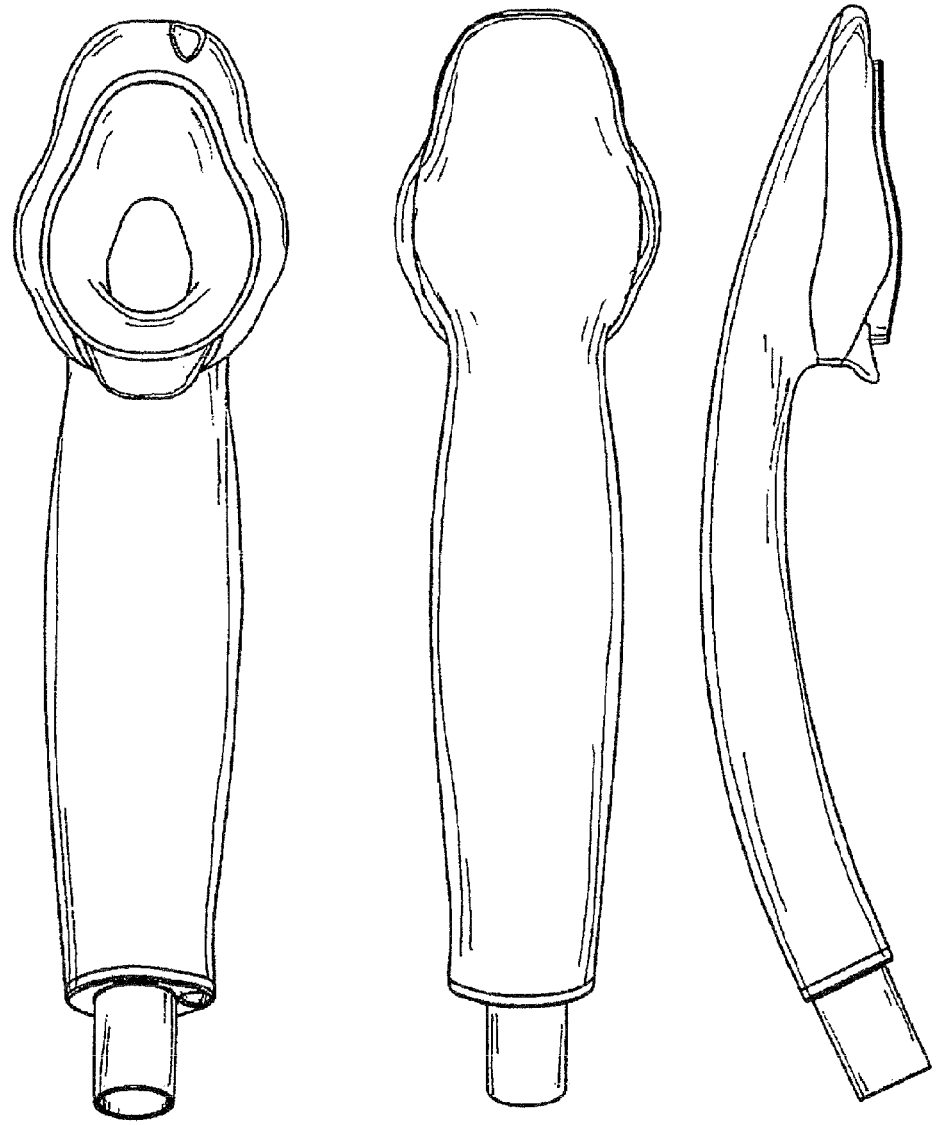
FIGS. 33 to 39 show front, back, side and end elevational views of a further embodiment of the present invention.
Figure 36:
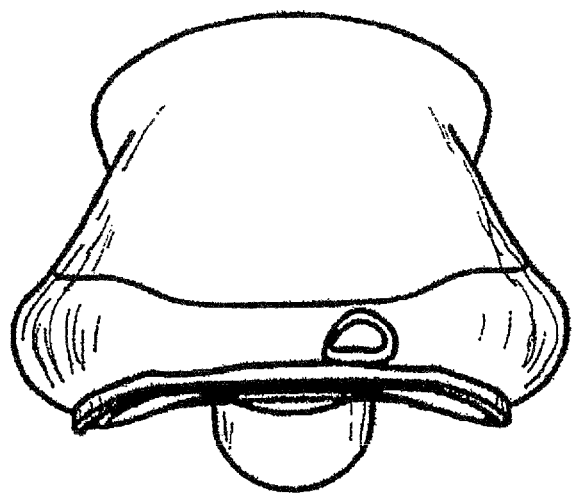
Figure 37:
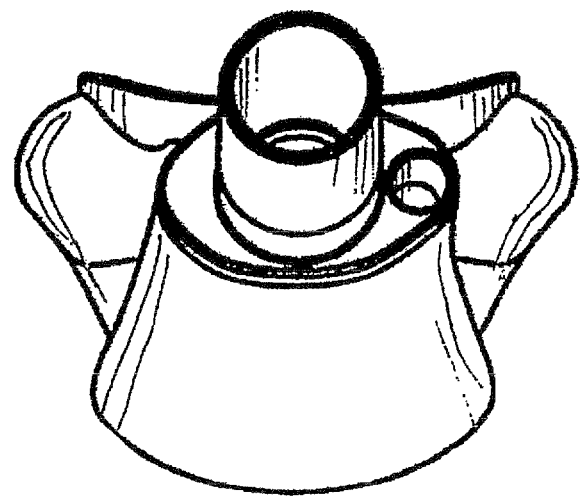
Figure 38:
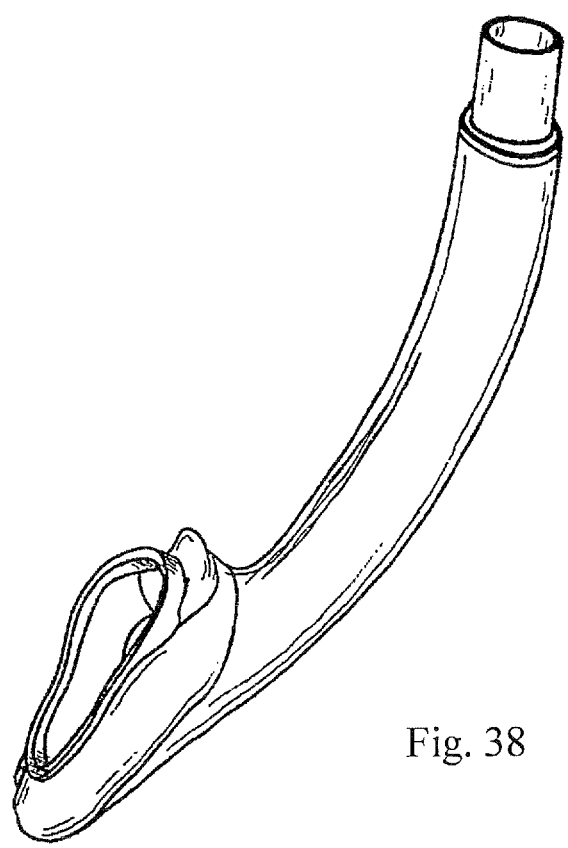
Figure 39:
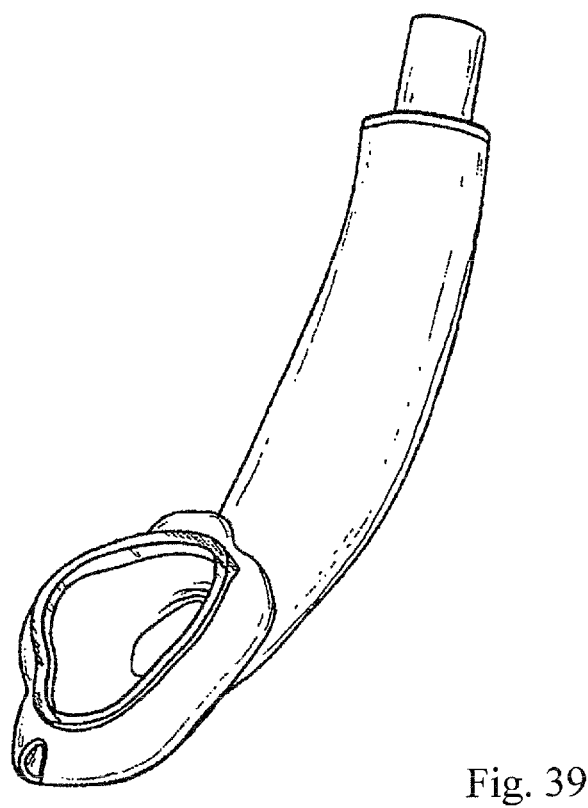
Figure 40:
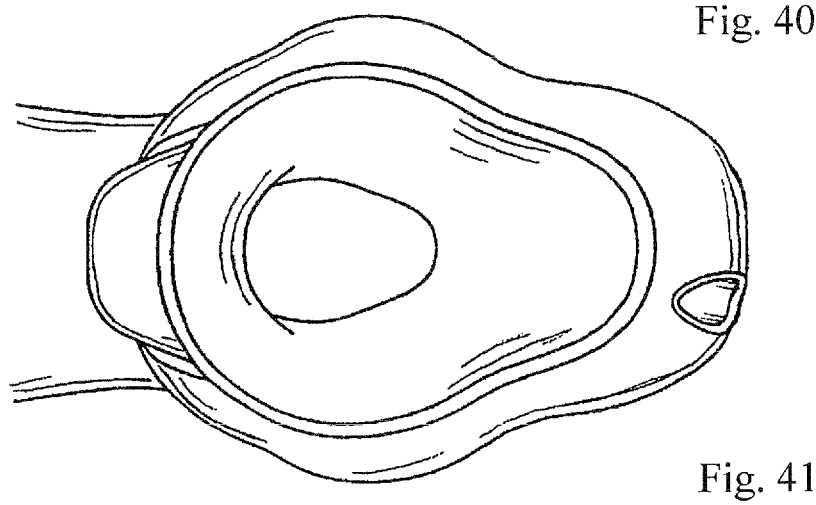
Figure 41:
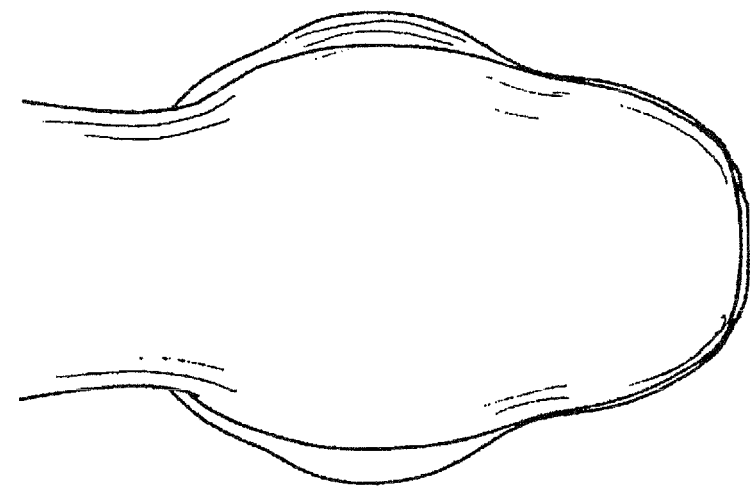
Figure 42:
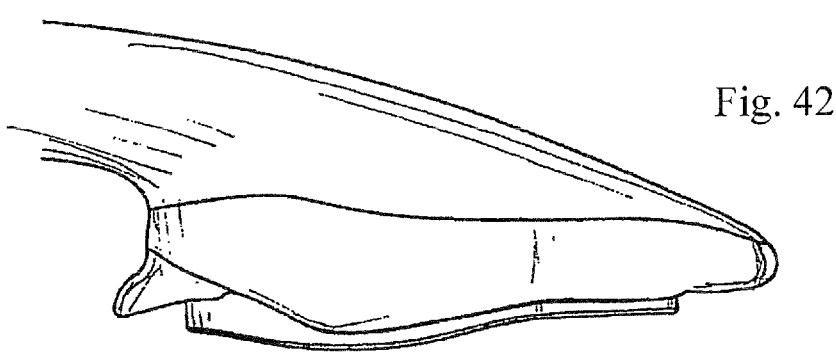
Figures 43, 44, 45:
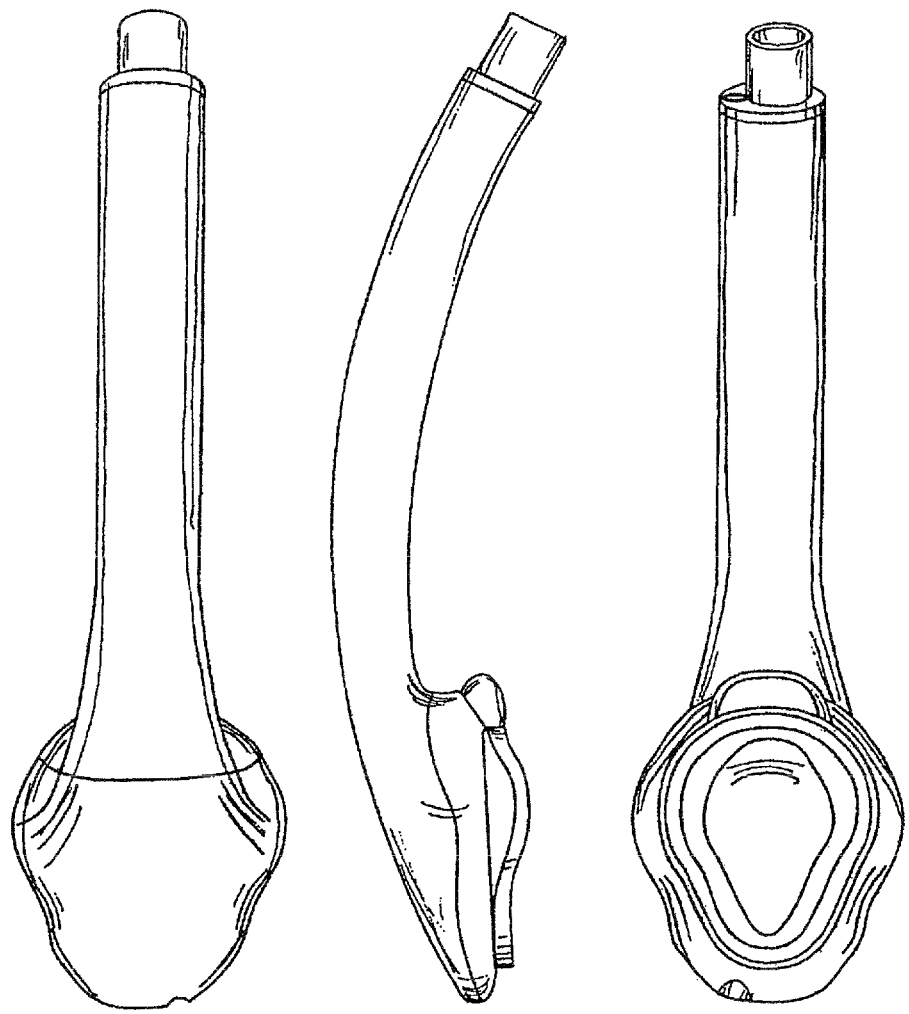
Figure 50:
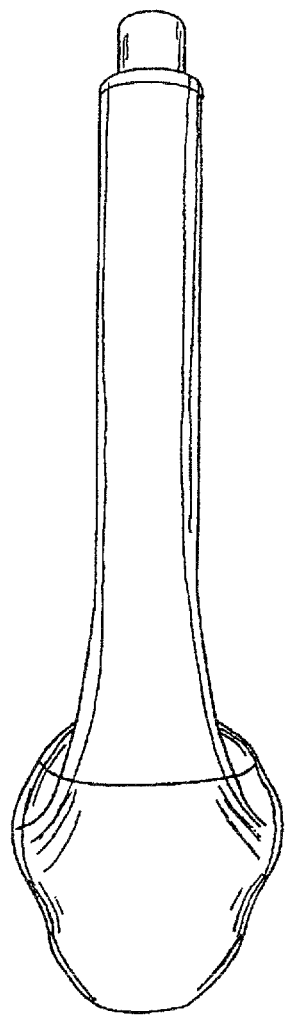
FIGS. 50 to 56 show front, back, side and end elevational views of another further embodiment of the present invention.
Figure 51:
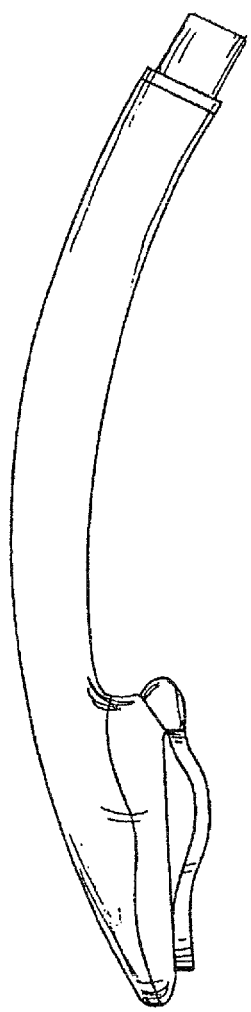
Figure 52:
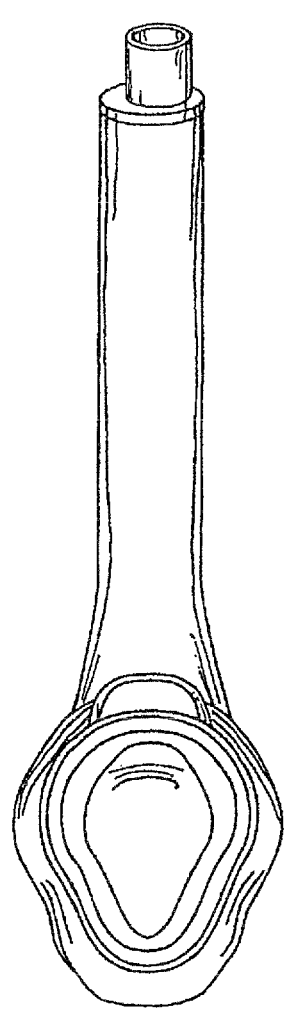
Figure 53:
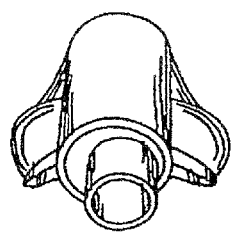
Figure 54:
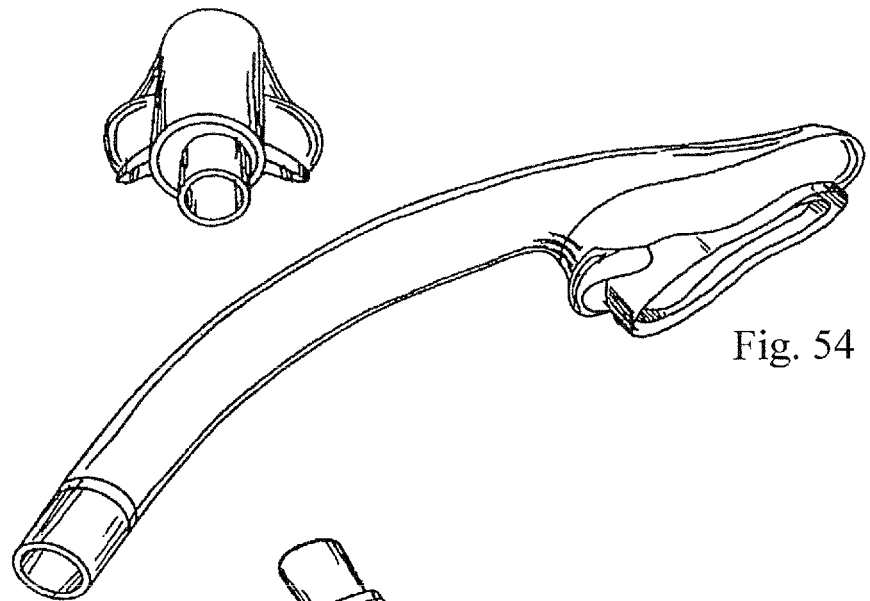
Figure 55:
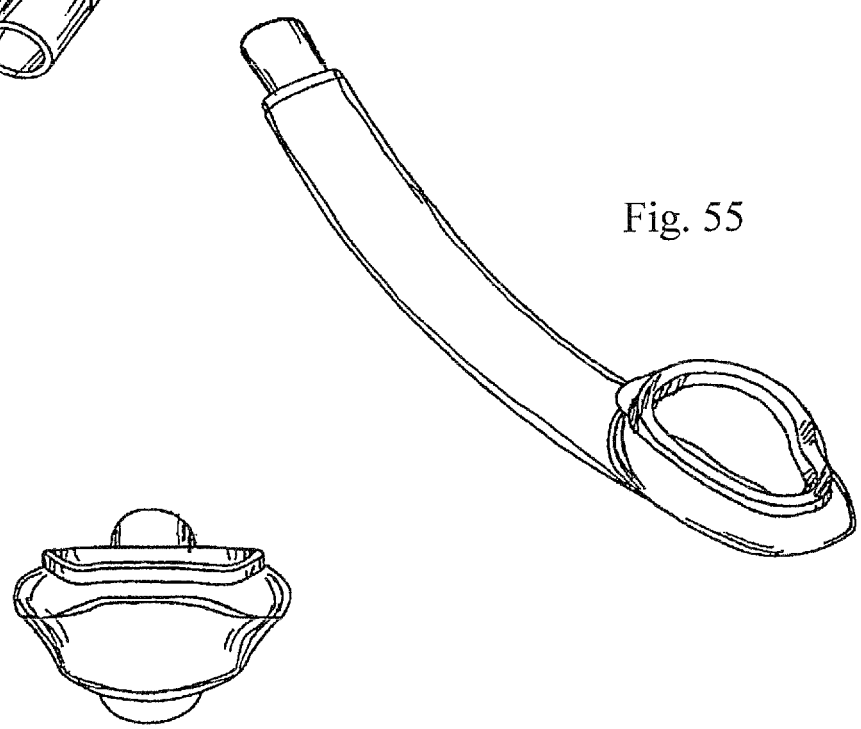
Figure 56:
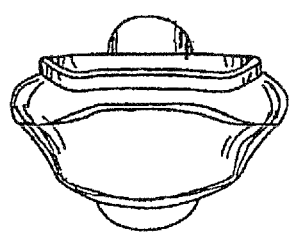
Figures 57, 58, 59:
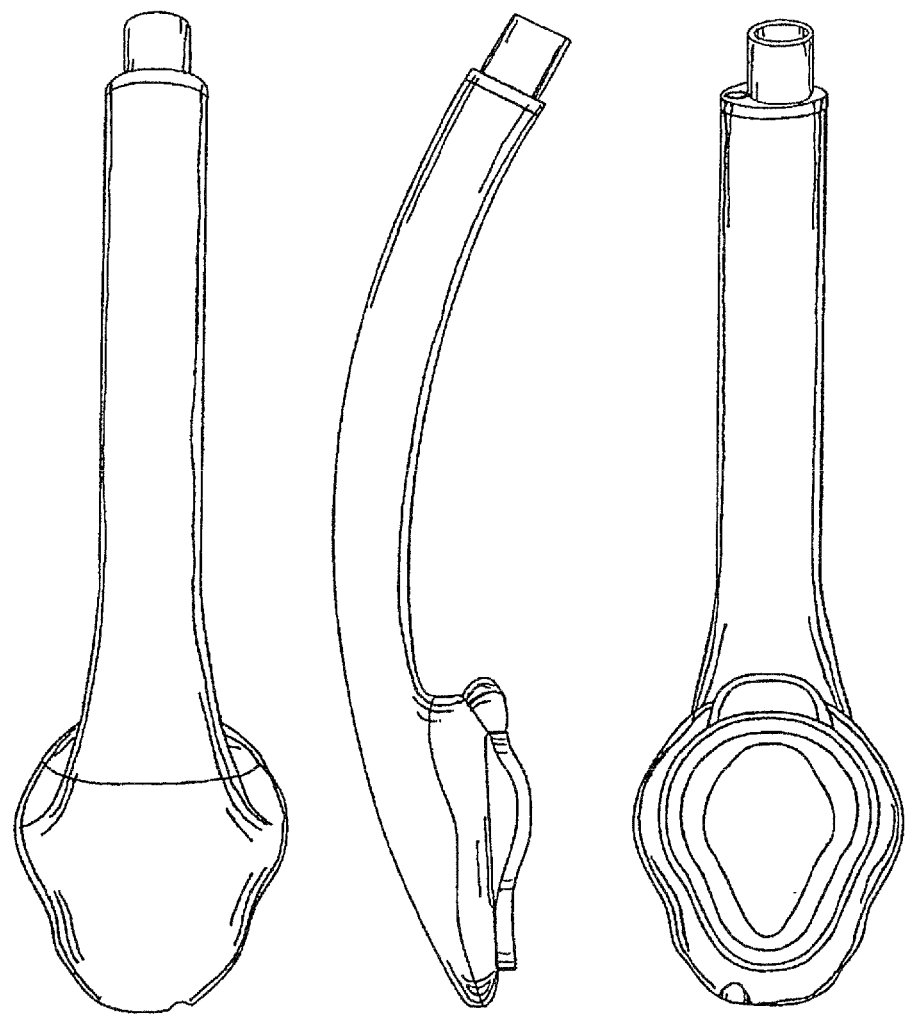
Figures 64, 65, 66:
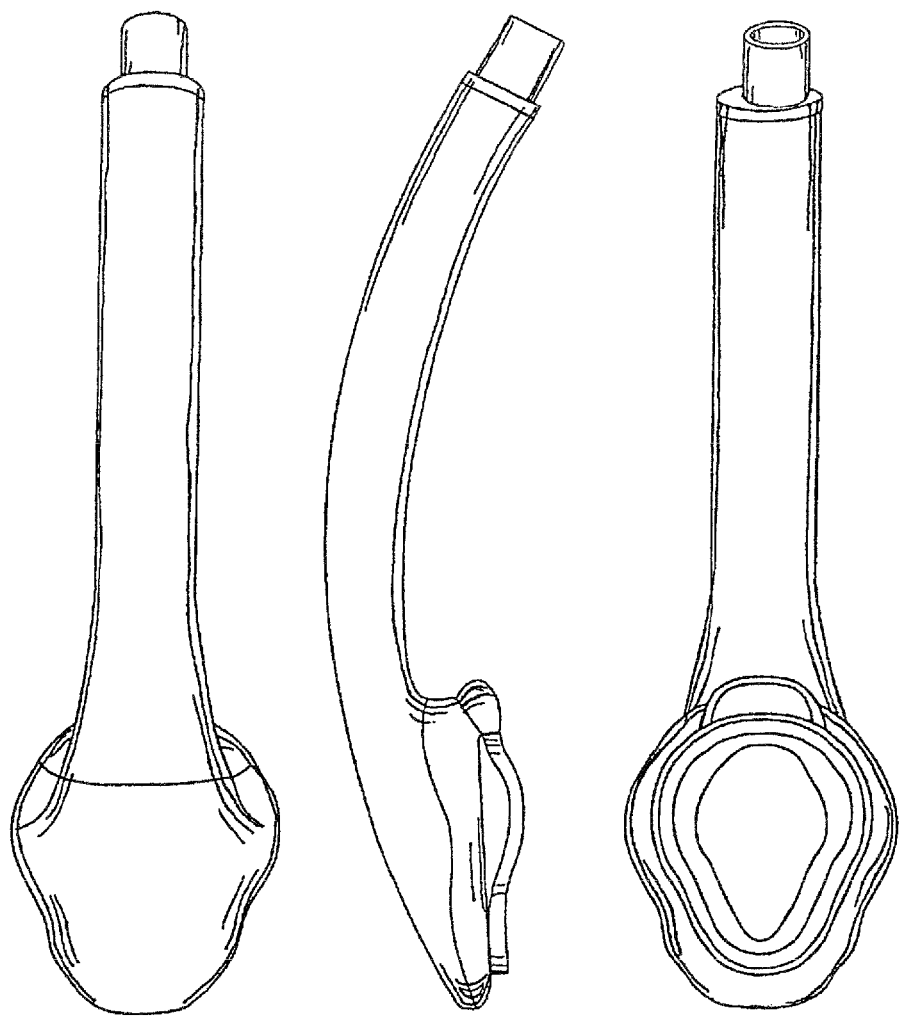
FIGS. 64 to 70 show front, back, side and end elevational views of another further embodiment of the present invention.
Figure 67:
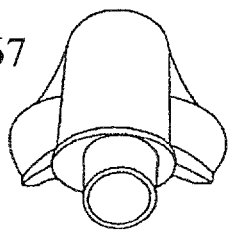
Figure 68:
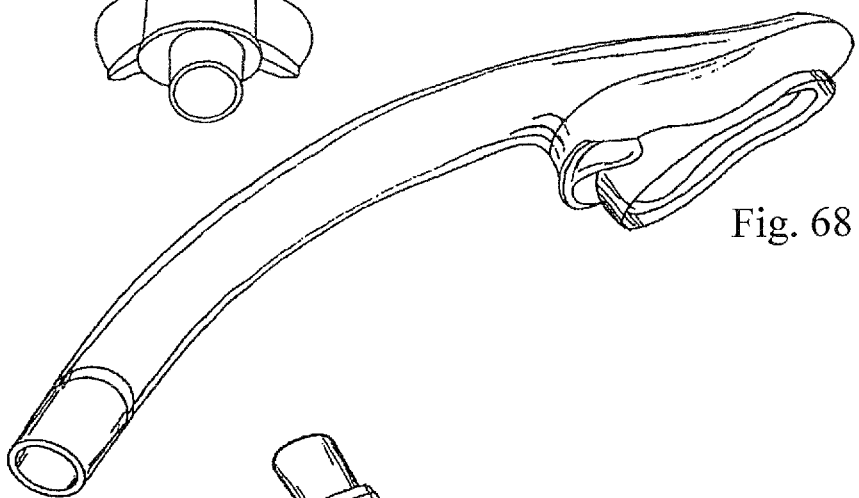
Figure 69:
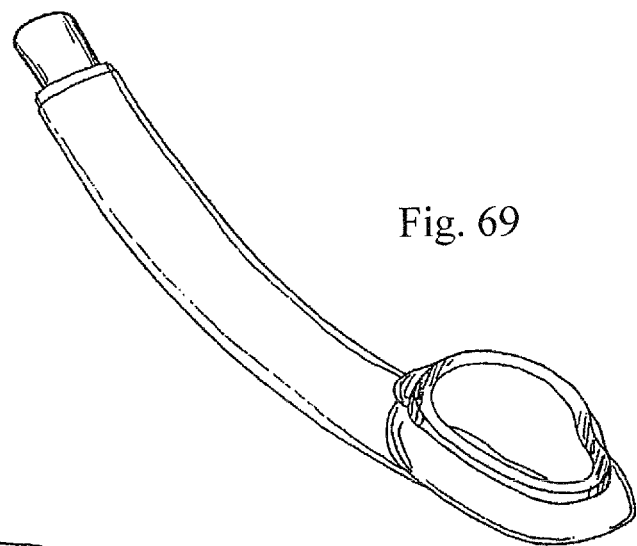
Figure 70:
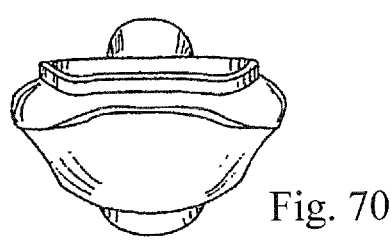
Figure 71:
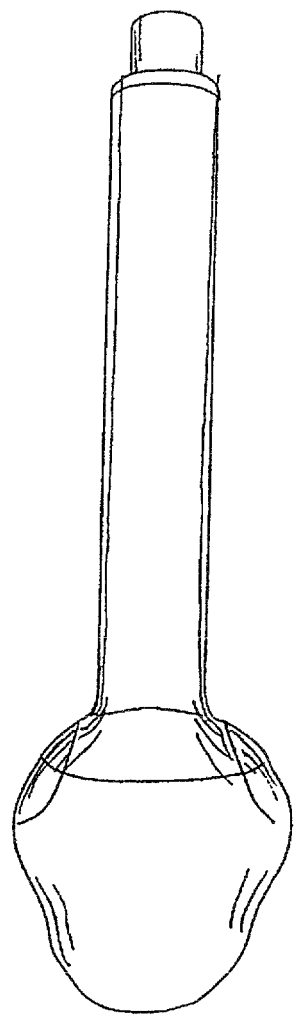
FIGS. 71 to 77 show front, back, side and end elevational views of another further embodiment of the present invention.
Figure 72:
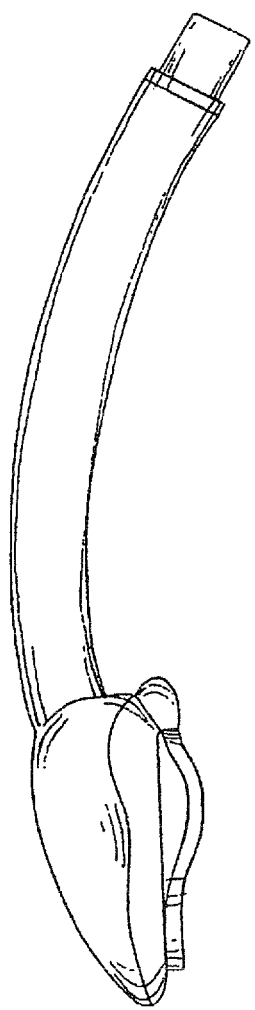
Figure 73:
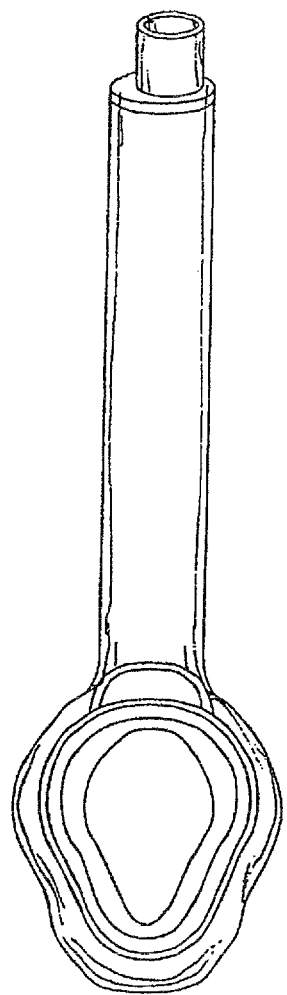
Figure 74:
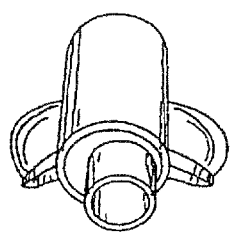
Figure 75:
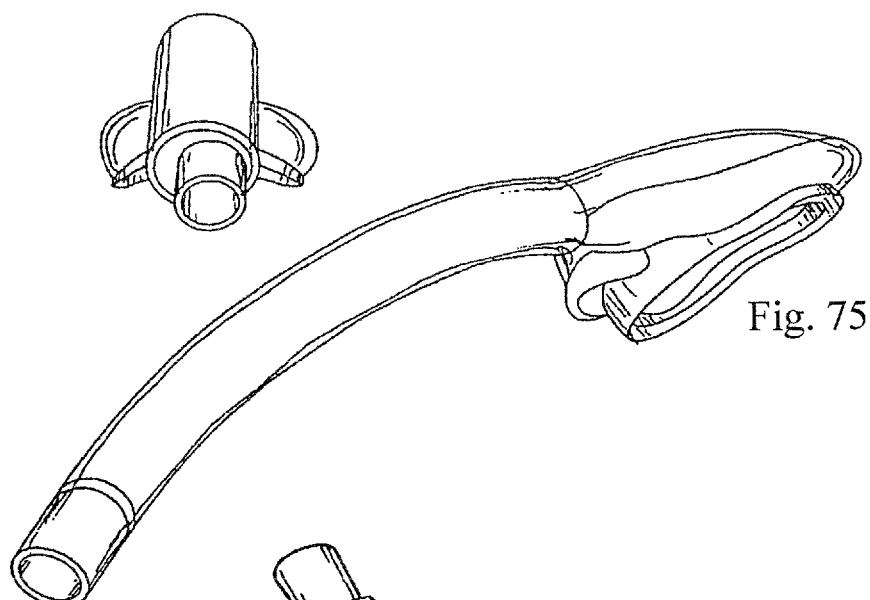
Figure 76:
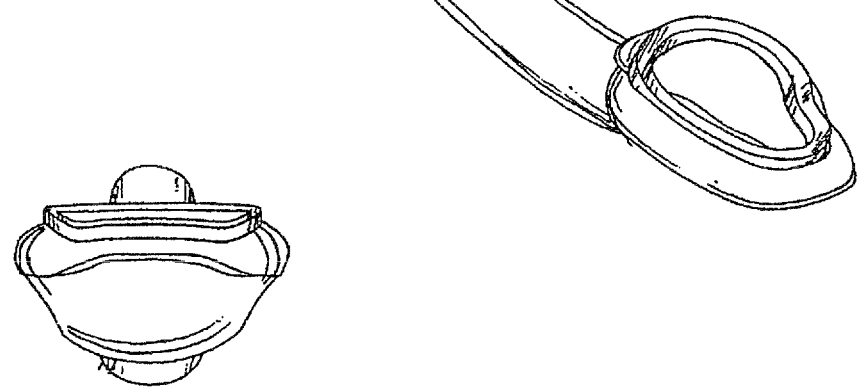
Figure 77:
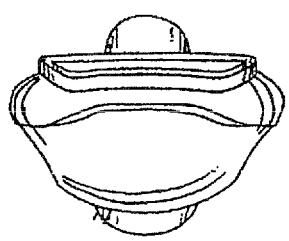

Another feature of the passageways in these embodiments is that they are displaced to one side of the central longitudinal axis of the device, in this case to the right-hand side of the central longitudinal axis, as viewed from the open face of the cuff. However, the passageway, which is optional, could just as well exit along the mid-line or on the central longitudinal axis of the device as illustrated by 742 in FIG. 33.

Figure 29A:
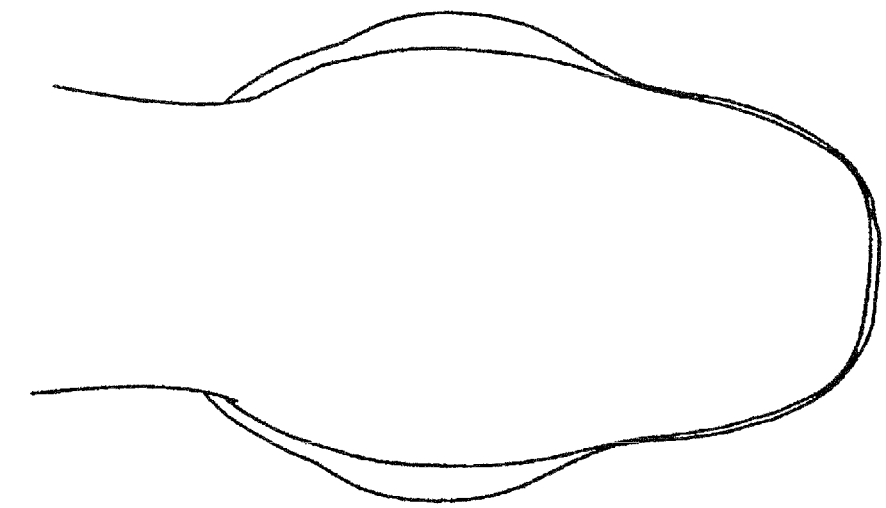
FIGS. 29A, B and C show enlarged rear, side and front elevational views of a laryngeal cuff.
Figure 29B:
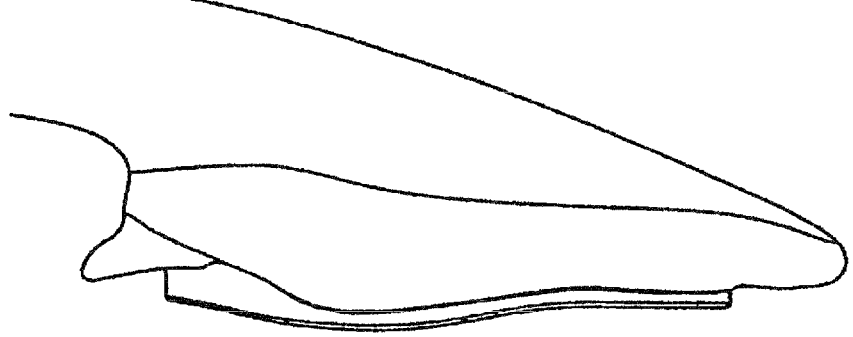
Figure 29C:
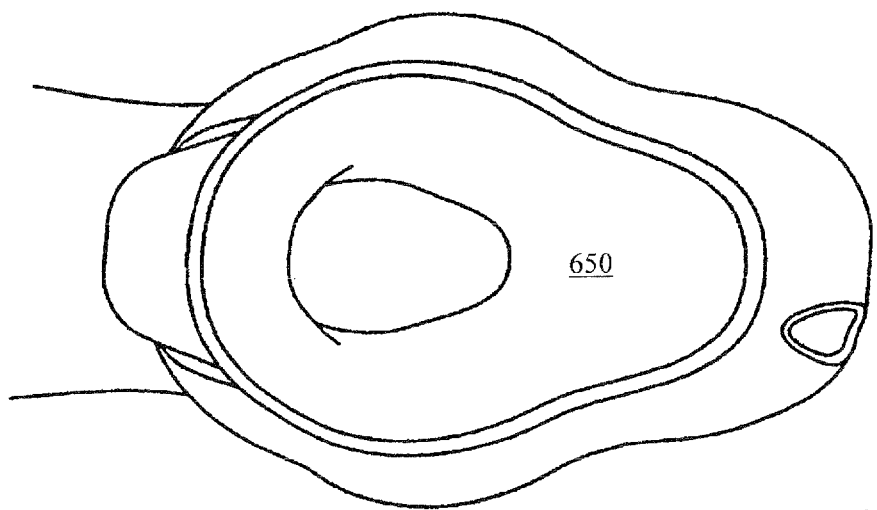

A further embodiment is illustrated in FIG. 29. In this example a laryngeal cuff is formed around a pre-formed or pre-cut piece of airway tube. This has the cost advantage that the airway tube may be formed from relatively inexpensive PVC tube or the like with a connector in one end and the cuff moulded over the other end. Once again the airway tube may be circular in profile or elliptical or any other profile as selected by the designer.

Figure 28A:
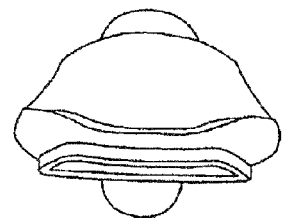
FIGS. 28A to D illustrate perspective views of the embodiment shown in FIG. 27.
Figure 28B:
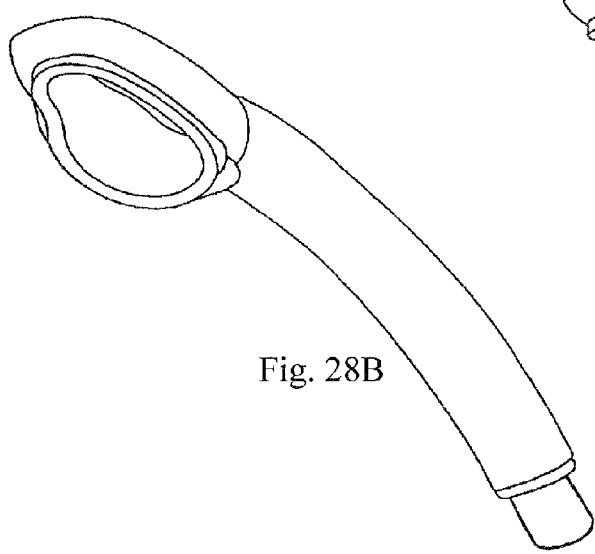
Figure 28C:
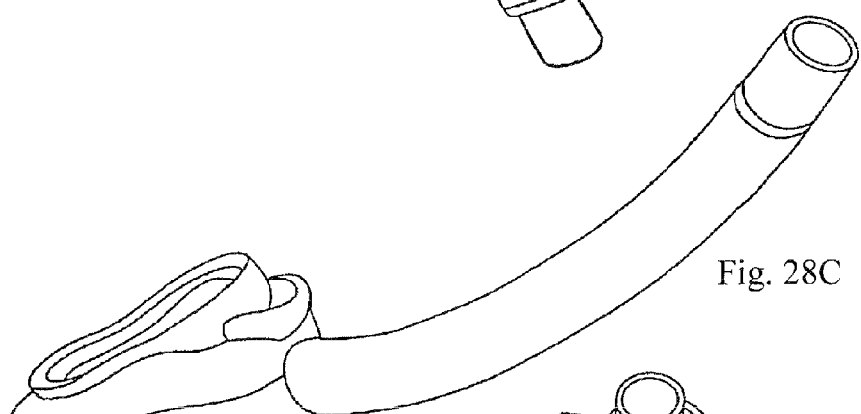
Figure 28D:
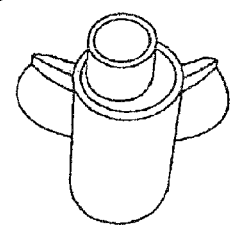

FIGS. 23B and 25B and 28B amongst others show the generally curvilinear shape of the device along its longitudinal axis. This shape is designed to correspond with the mouth/throat opening in an anaesthetised patient. Whilst the device is flexible it is resiliently deformable and tends to return to this concave/convex shape in its unstressed state.

Figure 30:
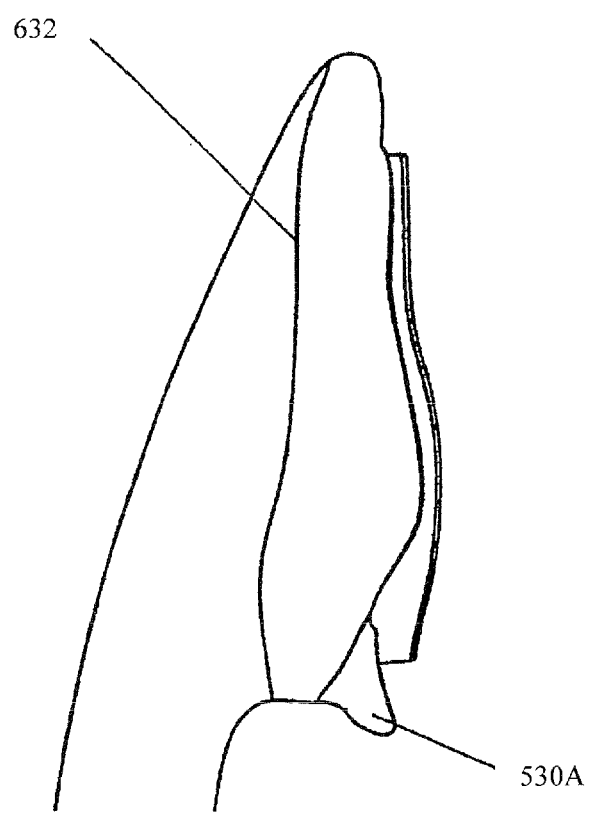
FIG. 30 shows an enlargement of a cuff, detailing the split line between different plastics which would be present if the cuff is to be formed by materials of two different shore hardnesses.

In addition to passing tubes or other items through the gastric tube passageway, it is possible to pass items such as a guide wire directly into the trachea through the airway tube. To facilitate this the interior surface 650 of the cuff within the opening is ramped so as to direct a probe into the trachea (see FIG. 30C).

The device may be constructed from any suitable plastics material as selected by the materials specialist. Latex-free medical grade silicone rubber is one preferred material. The cuff should be soft in texture to avoid undue damage to the surrounding tissue. Other suitable materials for construction of this type of device include, but are not limited to, Poly Vinyl Chloride (PVC), Thermoplastic Elastomers such as the styrenic block copolymers (eg Styrene Butadiene Styrene (SBS), Styrene Ethylene Butylene Styrene (SEBS)), and Thermoplastic Olefin Blends (TPO), Thermoplastic Poly-Urethanes (TPU), Thermoplastic Vulcanisates (TPV), Copolyester (COPE), Polyether Block Amides (PEBAX), Melt Processable Rubbers, Flexible Co-polymers such as EVA, and foamed versions thereof, where appropriate.

A further important factor involved in the choice of a suitable material is transparency. Ideally the material or materials of construction should be substantially clear or transparent. This enables the anaesthetist or operator to see the inner lumen of the airway to check for blockages or other problems. Such transparent materials are known to the materials specialist.

By way of a preferred softness (hardness) range, on the Shore A scale of Hardness, a hardness of less than 30 for the face of the cuff that contacts the laryngeal inlet is optimum. By way of a preferred range, a value on the same scale of between 0 to 20 is preferred, with a particularly preferred range of 0 to 5. The apparent softness of the cuff can be further adapted by forming cavities or channels within the body of the cuff itself.

In a further embodiment the cuff may be pre-filled with a fluid such as air, or other non-toxic gas, or a non-toxic liquid. In this context the term fluid has a broad meaning and includes any suitable gas, liquid, vapour or mixtures or combination thereof and will be determined and designed by an expert in this field of anatomy/anaesthesia in conjunction with the materials specialist. The cuff will be constructed of such a material which will not allow nitrous oxide (anaesthetic gas) to diffuse through the material to any significant amount so that the extra luminal pressure is kept constant. It follows therefore that the cuff should be substantially impermeable to the fluid with which is filled and to anaesthetic gases.

Alternatively, the cuff can be formed from a soft, foamed material or can be foam filled. In either case this provides a soft deformable but shaped surface around the face of the cuff to engage over the anatomy of the laryngeal inlet region. Such a foam filled device will minimise any potential damage to the structures in that region whilst still providing a substantially complete seal.

In the case of embodiments with a substantially circular airway tube and a gastric tube passageway which runs internally along the length of the device (as shown for example in FIGS. 23 and 24), the centre of the bore of the airway tube can be displaced to one side of the central or mid-line axis of the airway tube itself. This displacement provides space for the gastric tube passageway to run alongside the bore of the airway tube. This arrangement is shown most clearly in FIG. 24D. The gastric tube passageway is, in effect, housed within the outer body of the airway tube. This arrangement makes for a neat, streamlined appearance in comparison to the arrangement in which the gastric tube passageway is external to or mounted on the back of the device.

In terms of materials of manufacture and construction of an airway device according to the present invention, it is advantageous to form the front or open face of the cuff from a softer material than the remainder of the device. FIG. 23B shows a so-called "split line" 532 between the softer plastics material on the face of the cuff and slightly firmer material on the dorsal or back part of the cuff 519. The exact position of this split line may vary as determined by the designer. This line is shown in a slightly different position in FIG. 31, where it is shown as feature 632.

By moving this split line towards the dorsal face of the cuff, this ensures that the sides of the cuff 533, 534 are also made of the softer material. The sides are therefore more easily deformed which contributes significantly to the ease of insertion, and removal, of the cuff during use. The cuff squeezes and seals into the space above the laryngeal inlet, cupping the laryngeal inlet to create a good seal for ventilation. As the cuff reduces in width and squeezes into position, the airway opening increases in depth. This increase in depth reduces the likelihood of the epiglottis occluding the airway during ventilation, a problem with prior art devices.

Turning now to methods of manufacturing airway devices generally, and in particular airway devices according to the present invention, several new and cost-effective methods have been devised. These include injection moulding the device as single unit using a one-shot or a two-shot process. Such methods also include extruding an airway tube and injection moulding a cuff around the tube in a one-shot or two-shot process.

It follows therefore that the airway tube may be manufactured by extrusion or injection moulding and the cuff portion may be formed by one-shot or two-shot injection moulding.

Accordingly, one method of making an airway device according to the present invention is to provide a mould, the mould including interior walls which define the shape of the airway device, and injecting into said mould a molten thermoplastic compound. Once cooled the item is ejected from the mould. In a further embodiment a two-shot process is used in which molten thermoplastic compound of a first hardness is first injected into the mould, which is retained in a pre-determined position such that only a pre-determined portion of the mould is filled with polymeric material. A second molten thermoplastic compound is then injected into the remaining space in the mould to complete the injection moulding process. In this manner the relatively firmer airway tube and dorsal portion of the cuff can be formed first and the relatively softer face of the cuff can be formed in the second part of the operation. Alternatively the face of the cuff can be formed first and the remainder of the device is formed in the second part of the operation.

In an alternative method an airway tube is formed in a first step, either by extrusion or cutting a pre-determined length from a longer length of tubing. A mould defining a hollow space which will become the cuff region in the finished product is then placed around the airway tube and thermosetting plastic is injected into the mould in a one-step or a two-step process.

In a third manufacturing embodiment a mould defining the cuff region is used to produce a cuff by either a one-step or a two-step injection moulding process. The cuff produced from this mould includes a recess adapted to accept an airway tube. In a separate operation or operations an airway tube is formed by extrusion or in some other manner. The airway tube is then inserted into and bonded to the recess provided in the cuff for that purpose.

According to a further method of manufacture, the moulding process may be used to mould not only the laryngeal cuff on to the end of a pre-formed airway tube, but also a soft coating over the airway tube itself. Whilst this requires a larger mould, and more plastics material, it has the advantage that the finished device has a uniform finish over substantially the whole of its outer surface. It is softer for the patient and more aesthetically appealing for the operator. Having a pre-formed airway tube running most of the length of the device gives a degree of resilience and rigidity which is particularly helpful when using very soft plastics material.

In terms of plastics materials used in these methods of manufacture, these will be determined by the materials specialist and are generally only limited by the ability to bond the chosen materials together. By way of example only typically PVC can be used to mould the airway tube, the whole of the cuff region, the dorsal portion of the cuff region or any seals between these components. Polyolefins such as polyethylene and polypropylene or a polyurethane can be used to form the airway tube and/or the dorsal portion of the cuff region. A thermoplastic elastomer or a silicone rubber can be used to form the airway tube, the face of the cuff, the dorsal portion of the cuff, the whole of the cuff and any secondary seals therebetween.

In this context the term "bond" has a particularly broad meaning. It encompasses any method or process in which two or more parts are permanently joined together. It includes, but is in no way limited to, molecular bonding, glueing using chemical adhesives, welding, including ultrasonic welding. The preferred method or methods of bonding will be selected by the materials specialist in this area.

The invention claimed is:

1. A method of manufacturing an airway device suitable for human or animal use, said airway device comprising an airway tube having a distal end and a proximal end, the distal end of which is surrounded by a non-inflatable laryngeal cuff, said method comprising the steps of:—
   (i) providing a mould, the mould including interior walls defining an interior volume which defines the shape of the airway device;
   (ii) introducing a liquid plastics material into the hollow interior volume of the mould;
   (iii) optionally introducing a second liquid plastics material into said mould where it is required that the airway device is made from materials of different Shore hardness;
   (iv) allowing the plastics material to solidify;
   (v) removing the airway device from the mould.

2. A method according to claim 1 wherein said method also comprises the step of inserting into said mould a connector suitable for connecting to an anaesthetic gas supply, such that, after the moulding process is complete, the connector becomes attached to the airway device.

* * * * *

UNITED STATES PATENT AND TRADEMARK OFFICE
CERTIFICATE OF CORRECTION

| | |
|---|---|
| PATENT NO. | : 8,778,248 B2 |
| APPLICATION NO. | : 13/403806 |
| DATED | : July 15, 2014 |
| INVENTOR(S) | : Muhammed Aslam Nasir |

It is certified that error appears in the above-identified patent and that said Letters Patent is hereby corrected as shown below:

On the Title Page
Page 2, second column, under "FOREIGN PATENT DOCUMENTS," line 38, "000482195-0006" should be --000482195-0001--.

Signed and Sealed this
Fourth Day of November, 2014

Michelle K. Lee
*Deputy Director of the United States Patent and Trademark Office*